US007112341B1

(12) United States Patent
Nagarajan et al.

(10) Patent No.: US 7,112,341 B1
(45) Date of Patent: Sep. 26, 2006

(54) PULMONARY ADMINISTRATION OF DRY POWDER FORMULATIONS FOR TREATING INFERTILITY

(75) Inventors: Sudha Nagarajan, Palo Alto, CA (US); John S. Patton, Portola Valley, CA (US); David B. Bennett, San Jose, CA (US); Joanne Greene, Redwood City, CA (US); Hi-Shi Chiang, San Jose, CA (US); Cheryl L. M. Stults, San Mateo, CA (US); Geraldine Venthoye, Foster City, CA (US); Darrel LaVern Allen, Indianapolis, IN (US); Benjamin Lee Hughes, Indianapolis, IN (US); Mary Stiff-Torvik, Greenfield, IN (US); Ronald Keith Wolff, Carmel, IN (US); William David Roeder, Zionsville, IN (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 09/958,722

(22) PCT Filed: Apr. 13, 2000

(86) PCT No.: PCT/US00/09869

§ 371 (c)(1),
(2), (4) Date: Oct. 11, 2001

(87) PCT Pub. No.: WO00/61178

PCT Pub. Date: Oct. 19, 2000

Related U.S. Application Data

(60) Provisional application No. 60/130,099, filed on Apr. 20, 1999, provisional application No. 60/129,121, filed on Apr. 13, 1999.

(51) Int. Cl.
*A61K 9/00* (2006.01)
*A61K 9/12* (2006.01)
*A61K 9/14* (2006.01)
*A61K 38/24* (2006.01)

(52) U.S. Cl. .......................... 424/499; 424/489; 514/2; 514/12; 530/399

(58) Field of Classification Search ................ 424/489; 514/2; 530/398
See application file for complete search history.

(56) References Cited

U.S. PATENT DOCUMENTS 3,906,950 A 9/1975 Cocozza
4,013,075 A 3/1977 Cocozza
4,234,571 A 11/1980 Nestor et al.
4,458,066 A 7/1984 Caruthers et al.
4,552,864 A 11/1985 Antoni et al.
4,667,668 A 5/1987 Wetterlin
4,668,218 A 5/1987 Virtanen
4,805,811 A 2/1989 Wetterlin
4,891,319 A 1/1990 Roser
5,089,423 A * 2/1992 Diamandis et al. ......... 436/518
5,128,453 A 7/1992 Arpaia et al.
5,156,957 A 10/1992 Reddy et al.
5,270,057 A 12/1993 de Meere et al.
5,320,094 A 6/1994 Laube et al.
5,384,132 A 1/1995 de Meere et al.
5,388,572 A 2/1995 Mulhauser et al.
5,405,945 A 4/1995 Boime et al.
5,458,135 A 10/1995 Patton et al.
5,522,385 A 6/1996 Lloyd et al.
5,580,734 A 12/1996 Treco et al.
5,639,640 A 6/1997 Reddy et al.
5,641,670 A 6/1997 Treco et al.
5,650,390 A 7/1997 Samaritani et al.
5,654,007 A 8/1997 Johnson et al.
5,672,581 A 9/1997 Rubsamen et al.
5,733,761 A 3/1998 Treco et al.
5,740,794 A 4/1998 Smith et al.
5,767,067 A 6/1998 Arpaia et al.
5,767,251 A 6/1998 Reddy et al.
5,785,049 A 7/1998 Smith et al.
5,952,008 A 9/1999 Bäckström et al.
5,960,792 A 10/1999 Lloyd et al.
5,990,288 A * 11/1999 Musick et al. .............. 530/398
6,004,574 A 12/1999 Bäckström et al.
6,030,604 A * 2/2000 Trofast ........................ 424/46
6,238,890 B1 * 5/2001 Boime et al. .............. 435/69.7
6,797,258 B1 * 9/2004 Platz et al. ................... 424/45

FOREIGN PATENT DOCUMENTS

EP 129985 B1 1/1985
EP 160699 B1 11/1985
EP 170502 A2 2/1986
EP 211894 B1 3/1987

(Continued)

OTHER PUBLICATIONS

Pettit et al. The development of site-specific drug-delivery systems for protein and peptide biopharmaceuticals. TIBTECH Aug. vol. 16, 343-349, 1998.*

(Continued)

*Primary Examiner*—Marianne P. Allen
*Assistant Examiner*—Regina M. DeBerry
(74) *Attorney, Agent, or Firm*—Steven J. Helmer

(57) ABSTRACT

Provided are stabilized follicle stimulating protein (FSP) dry powder compositions for aerosolized delivery to the deep lung, methods of preparing and administering such compositions, and methods for treating infertility involving administering the dry powders by pulmonary delivery to the deep lung.

68 Claims, 4 Drawing Sheets

FOREIGN PATENT DOCUMENTS

| | | | |
|---|---|---|---|
| EP | 322438 | B1 | 7/1989 |
| EP | 448146 | B1 | 9/1991 |
| EP | 472598 | B1 | 1/1992 |
| EP | 467172 | B1 | 4/1994 |
| WO | WO 85/01959 | A1 | 5/1985 |
| WO | WO 85/01958 | A1 | 3/1992 |
| WO | WO 95/00128 | A1 | 1/1995 |
| WO | WO 95/09616 | A1 | 4/1995 |
| WO | WO 96/19207 | A1 | 6/1996 |
| WO | WO 96/19197 | A1 | 7/1996 |
| WO | WO 96/32096 | A1 | 10/1996 |
| WO | WO 96/32116 | A1 | 10/1996 |
| WO | WO 97/41031 | A1 | 11/1997 |
| WO | WO 97/41833 | A1 | 11/1997 |
| WO | WO 98/16205 | A2 | 4/1998 |
| WO | WO 98/16207 | A1 | 4/1998 |
| WO | WO 99/24061 | A1 | 5/1999 |
| WO | WO 00/04913 | A1 | 2/2000 |

OTHER PUBLICATIONS

Allen et al., *J. Appl. Toxicol.*, 15(1):13-17 (1995).
Baenziger and Green, *Biochem. Biophys. Acta*, 947, 287-306 (1988).
Beaucage and Caruthers, *Tetra. Letts.*, 22(20):1859-1862 (1981).
Beck et al., *DNA*, 4:76 (1985).
Beitens and Padmanabhan, *Trends Endocrinol. Metab.*, 2, 145-151 (1991).
Bishop et al., *Mol. Endocrinol.*, 8:722-731 (1994).
Bishop et al., *Endocrine*. 136:2635-2640 (1995).
Boime et al., *Seminars in Reproductive Endocrinology*, 10:45-50 (1992).
Brown et al., *Meth. Enzymol.*, 68:109-151 (1979).
Chappel et al., *Proceedings of the 3rd World Congress on Gynocological Endocrinology*, 179-184 (1992).
Combarnous, Y., *Endocrine Reviews*, 13(4):670-691 (1992).
Coy et al., *Biochem. Biophys. Res. Commun.*, 67:576-582 (1975).
Cunningham and Wells, *Science*, 244:1081-1085 (1989).
Dahl et al., *Meth. Enzymol. 169*: 414-422 (1989).
Dahl et al., *Science*, 239, 72-74 (1988).
Dahl et al., *Journal of Andrology*, 13:11-22 (1992).
de Vos et al., *Science*, 255:306-312 (1992).
Eastman et al., *Hum. Gene Ther.*, 8(6):765-773 (1997).
Fares et al., *PNAS*, 89:4304-4308 (1992).
Fujino et al., *J. Med. Chem.*, 16:1144-1147 (1973).
Hakola et al., *Mol. Cell. Endocrinol.*, 127, 59-69 (1997).
Hard et al. *Eur. J. Biochem.*, 193, 1064-1069 (1990).
Harris et al., *Mol. Hum. Reprod.*, 2, 807-811 (1996).
Jockenhövel et al., *Clin. Endocrinol. Metab.*, 33, 573-584 (1990).
Jones et al., *Fertil. Steril*, 38:14-21 (1982).
Keene et al., *J. Biol. Chem.*, 264:4769-4775 (1989).
Kelton et al., *Molec. Cell. Endocrinol. 89*:141-151 (1992).
Kesner et al., Reproductive Toxocology, 9(3):239-244 (1995).
Komada et al., *J Pharm Sciences*, 83, (6):863-867 (1994).
LaPolt et al., *Endocrinol. 131*:2514-2520 (1992).
le Contonnec et al., *Pharm. Res.*, 12(6):844-850 (1995).
Loumaye et al., *Fertil. Steril.*, 63:77-86 (1995).
Lu et al., *Pharm. Res.*, 15(8):1202-1206 (1998).
McDonald et al., *Pharm. Res.*, 15(5):671-679 (1998).
Monahan et al., *Biochemistry*, 12:4616-4620 (1973).
Mulders et al., *Biologicals*, 25:269-281 (1997).
Narang et al., *Meth. Enzymol.*, 68:90-99 (1979).
Needham-VanDevanter et al., *Nucleic Acids Res.*, 12:6159-6168 (1984).
Roth and Dias, *Biochem. 35*:7928-7935 (1996).
Saxena, B.B. and Rathnam, P., *J.Biol. Chem.*, 251:993-1005 (1976).
Schneider, J., *Embryol. Exp. Morphol.*, 27:353-365 (1972).
Shome, B. and Parlow, A.F., *J. Clin. Endocrinol. Metab.*, 39(1):203-205 (1974).
Shome et al., *J. Prot. Chem.*, 7:325-339 (1988).
Smith et al., *J. Mol. Biol.*, 224:899-904 (1992).
Speroff et al., *Clinical Gynecologic Endocrinology and Infertibility*, 583-609 (1989).
Sprengel et al., *Mol. Endocrinol. 4*:525-530 (1990).
Stanton et al., *Endocrinology*, 130, 2820-2832 (1992).
Steelman and Pohley, *Endocrinol. 53*:604 -616 (1953).
Thotakura and Blithe, *Glycobiology*, 5, 3-10 (1995).
Tilly et al., *Endocrinol. 131*:799-806 (1992).
Ulloa-Aguirre et al., *Endocr. Rev.*, 16, 765-787 (1995).
Valove et al., *Endocrinol 135*:2657-2661 (1994).
Wagner, J., *Pharmacokinetics for the Pharmaceutical Scientist*, 188-197 (1993).
Watkins et al., *DNA*, 6:205-212 (1987).
Wei et al., *J. of Molecular Biology*, 4(1):76 (1985).
Witcomb et al., *J. Clin. Endocrinol Metab*, 70:3-7 (1990).
Zlokamik et al., *Science*, 279, 84-88 (1998).
US 5,733,746, 03/1998, Treco et al. (withdrawn)

* cited by examiner

PULMONARY ADMINISTRATION OF DRY POWDER FORMULATIONS FOR TREATING INFERTILITY

This application claims the benefit of priority of U.S. Provisional Patent Application Ser. No. 60/129,121 filed Apr. 13, 1999 and Ser. No. 60/130,099, filed Apr. 20, 1999, both of which are incorporated in their entirety by reference.

FIELD OF THE INVENTION

The present invention is directed to pulmonary administration of stable, dry powder compositions comprising a follicle stimulating protein (FSP) and suitable for delivery to the deep lung, to methods for preparing and administering such compositions, and to methods for treating infertility.

BACKGROUND OF THE INVENTION

Follicle stimulating hormone (FSH) is a heterodimeric gonadotropic hormone secreted by the pituitary gland, and is one of three anterior pituitary glycoprotein hormones including, in addition to FSH, thyroid-stimulating hormone (TSH) and luteinizing hormone (LH). FSH consists of two non-covalently bound subunits referred to as the alpha ($\alpha$) and beta ($\beta$) subunits. The alpha subunit is the same amongst the three hormones, while the beta subunit is unique to each hormone and confers specificity. In humans, the mature alpha subunit consists of 92 amino acid residues and possesses two carbohydrate chains. The corresponding FSH mature beta subunit is composed of 111 amino acids and also possesses two carbohydrate chains. Together, the two subunits have a molecular weight of about 31 kD measured by mass spectroscopy and about 35–45 kD measured by PAGE or gel chromatography depending upon the state of glycosylation. FSH directly regulates the metabolic activity of granulosa cells of the ovary and Sertoli cells of the testis.

Pharmaceutical preparations of follicle stimulating hormone (FSH) play an important role in the treatment of human infertility, and administration of FSH, either alone or in combination with other biologically active compounds and proteins, has been employed for treating infertility problems since the early 1960s. In females, FSH promotes ovarian follicular development and pharmaceutical preparations of FSH are used primarily for ovulation induction and in in vitro fertilization procedures. [Speroff, L. Glass R. H., et al., *Clinical Gynecologic Endocrinology and Infertility.* 583–609 (1989); Jones, H. W., et al., *Fertil. Steril,* 38:14–21 (1982)]. In males, such compositions are used to initiate and maintain spermatogenesis in hypogonadotropic hypogonadism [Witcomb, R. W., et al., *J. Clin Enzdocrinol Metab,* 70:3–7 (1990)].

In early infertility treatment methods, FSH-containing formulations were administered via injection into deep muscle. Such injections were typically given with the aid of the patient's partner or healthcare provider and required the use of a needle up to five times the size of a typical subcutaneous needle and were very painful. More recently, formulations have been developed in which purified or recombinant FSH is administered subcutaneously, often by patient self-administration. Although subcutaneously administered FSH offers an advantage over intrasmuscularly delivered drug by allowing the patient greater independence through self-administered treatment, many patients are reluctant or unwilling to undergo infertility treatments requiring the subcutaneous administration of FSH, due to the inconvenience, discomfort, or even inherent dislike associated with needle-based delivery methods.

Pulmonary delivery has received much attention as an attractive alternative to subcutaneous injection, because this approach eliminates the necessity for needles, limits irritation to the skin and body mucosa (common side effects of transdermally, iontophoretically, and intranasally delivered drugs), and eliminates the need for nasal and skin penetration enhancers (typical components of intranasal and transdermal systems that often cause skin irritations/dermatitis). Pulmonary administration is also economically attractive, amenable to patient self-administration, and is often preferred by patients over other alternative modes of administration. However, due to their high molecular weight and low lipophilicity, peptide or protein based drugs have not traditionally been among those drugs that are administered by inhalation for deposition in and absorption from the lung, although various aerosol formulations have been suggested. Moreover, a previous attempt to administer FSH in dry powder form via intratracheal delivery resulted in apparently low bioavailability—0.6 percent relative to intravenous administration—suggesting the undesirability of the pulmonary route for delivering gonadotropin hormones such as FSH [Komada, F., et al., *J Pharm Sciences,* 83, (6):863–867 (1994)].

Another often-encountered problem in formulating proteins for administration is their tendency towards inactivation. With the recent advent of more effective purification and recombinant techniques, highly purified forms of both urinary-derived [Arpaia, G., et. al., U.S. Pat. No. 5,128,453, Jul. 7, 1992] and recombinant [Loumaye, E., et al., *Fertil. Steril.,* 63:77–86 (1995)] FSH have become available, making this problem even more pronounced. Although these highly purified forms of FSH offer many potential advantages over less purified forms, including improved batch-to-batch consistency, high specific activity due to the absence of luteinizing hormone and other competing proteins, improved efficacy, good local tolerance to injections, and low immunogenicity, preparations containing very pure FSH are often highly unstable. These compositions often degrade in a relatively short time, with a partial or even complete loss of bioactivity. Moreover, although excipients have been described which are capable of stabilizing FSH-containing solid formulations [e.g., Samaritani, et al., U.S. Pat. No. 5,650,390, Jul. 22, 1997] for reconstitution to injectable forms, such solid formulations typically lack the features necessary for pulmonary delivery.

Thus, even with the amount of work that has been done to optimize pulmonary delivery of proteins, there still does not exist an effective system and method of pulmonary delivery of FSH that (i) provides a sufficiently stabilized, respirable, dry powder form of FSH, (ii) eliminates the need for cold storage, (iii) provides powders having superior aerosol properties, (iv) requires neither propellants to aid in dispersion nor enhancer compounds to enhance absorption in the lower respiratory tract, and (v) exhibits good pulmonary bioavailability.

SUMMARY OF THE INVENTION

The present invention provides a stabilized FSH dry powder composition for delivery to the systemic circulation via the deep lung. The dry powder of the invention, when aerosolized and administered via inhalation, is useful in therapies and/or treatments for infertility.

The respirable, dry powder composition of the invention includes a pharmacologically effective amount of a follicle stimulating protein (FSP) and a pharmaceutically acceptable excipient. More specifically, the dry powder of the invention includes a mammalian urinary-derived or recombinant FSP.

The powders of the invention exhibit good bioavailabilities when aerosolized and administered by inhalation to the deep lung. A dry powder of the invention is characterized by a relative pulmonary bioavailability of at least about 1%, with relative pulmonary bioavailability values typically ranging from about 1% to 60%.

In another aspect, the invention is directed to a method of preparing a stabilized dry powder FSP composition as described above. The method includes the steps of mixing FSP and an excipient with a solvent to form a solution or suspension, and drying the solution or suspension to form a bioactive powder comprising dry particles containing FSP and the excipient material. Particular solvents for use in the method include water and alcohols. In a preferred embodiment of the method, the FSP composition is produced by spray drying.

In yet another aspect, the invention provides a method for delivering FSP to a mammalian subject in need thereof, where the method includes administering by inhalation a FSP dry powder composition as previously described in aerosolized form.

The invention also encompasses, in yet another aspect, a method for treating infertility in a mammalian subject, where a therapeutically effective amount of a FSP dry powder composition in accordance with the invention is administered to the subject by inhalation for deposition in and absorption from the lung. In a specific embodiment, the subject is an infertile female, and the FSP dry powder composition is administered periodically by inhalation into the subject's lungs for one or more cycles of treatment extending over a time course of at least 3–20 days, where, as a result of said administering, the subject exhibits a level of follicular growth that is increased relative to such level measured prior to said administering. In one particular embodiment, the therapeutically effective amount of FSP is from about 10 to 1000 IU of FSP per day. In another embodiment, the therapeutically effective amount of FSP is from about 50 to about 3000 IU of FSP per day. In yet another embodiment, in particular relating to super ovulation therapies (i.e., in vitro ferilization), the therapeutically effective amount of FSP is from about 200 to 12,000 IU of FSP per day.

These and other objects and features of the invention will become more fully apparent when the following detailed description is read in conjunction with the accompanying figures and examples.

BRIEF DESCRIPTION OF THE FIGURES

FIG. 2A demonstrates bioactivities of powders L2013 and L2010; FIG. 2B demonstrates bioactivities of powders L2006 and L2008.

DETAILED DESCRIPTION OF THE INVENTION

I. Definitions

Figure 1:
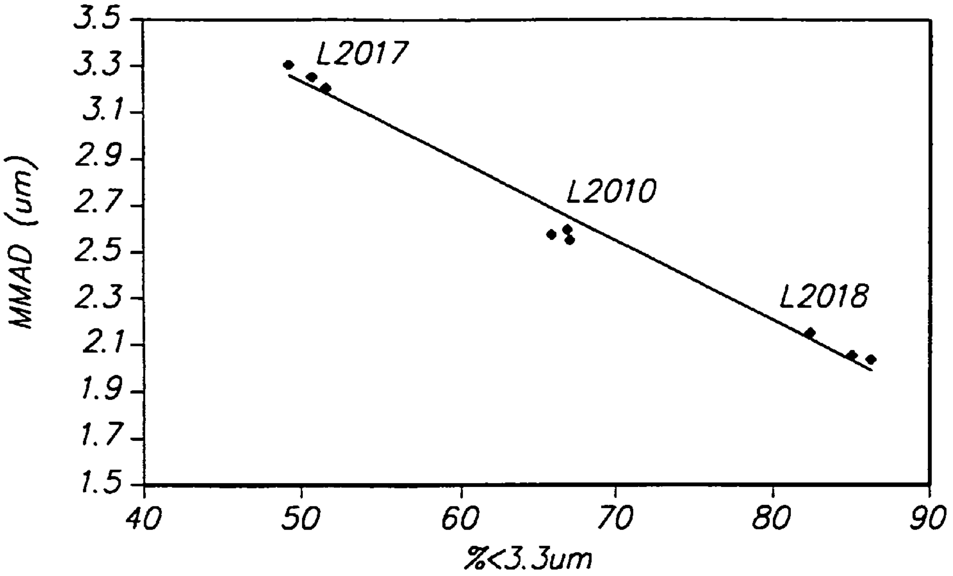
FIG. 1 is a graph showing the relationship between fine particle fraction (FPF, % less than 3.3 microns) and aerosol particle size (MMAD) for three exemplary FSP powder formulations (L2017, L2010, L2018) utilized in a one-month stability study, as described in detail in Example 7C.

"Bioactive powder" refers to a powder having either in vitro or in vivo activity, and typically refers to a powder containing one or more bioactive or pharmaceutical agents, such as FSP. "Bioactivity" of the powders of the invention can be generally measured using FSH assays known in the art, such as signal transduction assays, FSH receptor binding assay, or a version of the Steelman/Pohley in vivo rat ovarian weight assay, FSH half-life measurement and/or FSH bioactivity assay [Zlokarnik et al., *Science,* 279, 84–88 (1998); Dahl, K. et al., *Journal of Andrology,* 13:11–22 (1992); Roth and Dias, *Biochem.* 35:7928 (1996); Valvore, et al., *Endocrinol* 135:2657 (1994); Sprengel, et al., *Mol. Endocrinol.* 4:525 (1990); Tilly, et al., *Endocrinol.* 131: 799–806 (1992); Steelman and Pohley, *Endocrinol.* 53:604 (1953); Bishop et al., *Endocrine.* 136:2635 (1995); Mulders, et al., *Biologicals,* 25:269 (1997); Fares, *PNAS,* 89:4304 (1992); LaPolt, et al., *Endocrinol.* 131:2514 (1992)]. Further examples of such assays for in vitro biological activities, include, but are not limited to, measurement of estradiol production by granulosa cells using a rat granulosa cell aromatase assay [Dahl, et al., *Meth. Enzymol.* 169:414 (1989)]; and a FSH receptor activation assay, such as that described in Kelton, et al., *Molec. Cell. Endocrinol.* 89:141 (1992).

"Relative pulmonary bioavailability" is the percentage of the FSP dry powder dose deposited in the lungs that is absorbed and enters the blood of a mammal relative to the percent that is absorbed into the blood from an intramuscular or subcutaneous injection site. Representative model systems for determining relative pulmonary bioavailabilities include rat, rabbit, and monkey. The FSP dry powder composition of the invention is characterized by a relative pulmonary bioavailability of at least about 1% in plasma or blood, with relative pulmonary bioavailabilities generally ranging from about 1 to 20%, and preferably from about 1% to about 60%. Relative pulmonary bioavailability may be estimated by measuring absorption from direct intratracheal administration or by inhalation of an FSP-dry powder composition.

"Distribution phase", in reference to the half-life of FSP, refers to the initial rapid phase during which the hormone disappears from the plasma. The terminal slow or elimination phase half-life refers to the terminal slow phase during which hormone is eliminated from the body.

"Pharmaceutically acceptable salt" includes, but is not limited to, salts prepared with inorganic acids, such as chloride, sulfate, phosphate, diphosphate, hydrobromide, and nitrate salts, or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Citrate salt" refers to any pharmaceutically acceptable salt of citric acid with cations such as sodium, potassium, ammonium (including alkyl ammonium salts), calcium, and the like.

"Amino acid" refers to any compound containing both an amino group and a carboxylic acid group. Although the amino group most commonly occurs at the position adjacent to the carboxy function, the amino group may be positioned at any location within the molecule. The amino acid may also contain additional functional groups, such as amino, thio, carboxyl, carboxamide, imidazole, etc. The amino acids may be synthetic or naturally occurring, and may be used in either their racemic or optically active (D-, or L-) forms.

"Enhancer" refers to a compound that enhances the absorption of FSP through the epithelium of the lower respiratory tract and into the systemic circulation. In the presence of an enhancer, the amount of FSP absorbed into the systemic circulation is greater than the amount absorbed for a dry powder lacking such enhancer, and preferably is increased by at least about 150% of the amount absorbed in the absence of enhancer.

"Delivered dose efficiency" or "DDE" provides an indication of the delivery of a dry powder from the mouthpiece of a suitable inhaler device after a firing or dispersion event. DDE is synonymous with the term "emitted dose" or "ED." More specifically, the DDE (ED) is a measure of the percentage of powder which is drawn out of a unit dose package and which exits the mouthpiece of an inhaler device. DDE (ED) is defined as the ratio of the dose delivered by an inhaler device to the nominal dose (i.e., the mass of powder per unit dose placed into a suitable inhaler device prior to firing). DDE (ED) is an experimentally determined parameter, and is typically determined using a device that mimics patient dosing. To determine a DDE value, a nominal dose of dry powder, typically in unit dose form, is placed into a suitable dry powder inhaler (such as that described in U.S. Pat. No. 5,785,049, assigned to Inhale Therapeutic Systems) which is then actuated, dispersing the powder. The resulting aerosol cloud is then drawn by vacuum from the device, where it is captured on a tared filter attached to the device mouthpiece. The amount of powder that reaches the filter constitutes the delivered dose. For example, for a 5 mg, dry powder-containing dosage form placed into an inhalation device, if dispersion of the powder results in the recovery of 4 mg of powder on a tared filter as described above, then the DDE for the dry powder composition is: 4 mg (delivered dose)/5 mg (nominal dose)$\times$100=80%. For non-homogenous powders, DDE values provide an indication of the delivery of drug from an inhaler device after firing rather than of dry powder, and are based on amount of drug rather than on total powder weight.

"Fine particle fraction" or "FPF" is defined as the mass percent of aerosolized powder particles having an aerodynamic diameter less than 3.3 μm, typically determined by measurement in an Andersen cascade impactor. This parameter provides an indication of the percent of particles having the greatest potential to reach the deep lung of a patient for systemic uptake of a drug substance.

"Aerosol performance coefficient" or "APC" is an estimate of the total powder delivery efficiency from a unit dosage form (e.g., a blister pack) to the deep lung, and is determined experimentally using a short stack Anderson cascade impactor operated at a vacuum of 28.3 liters per minute. APC is synonymous with the term, "fine particle dose" or "FPD". The APC is defined as the total mass, in milligrams, of aerosolized powder having a particle size less than 3.3 micrometers, relative to the mass of powder contained in a unit dosage form (e.g., blister or capsule), in milligrams, and expressed as a percentage: APC (%)=total aerosolized powder mass less than 3.3 μm (mg)÷unit dosage form fill mass$\times$100.

"Dry powder" refers to a composition that contains finely dispersed solid particles that are free flowing and capable of (i) being readily dispersed in an inhalation device and (ii) inhaled by a subject so that a portion of the particles reach the lungs to permit penetration into the alveoli. Such a powder is considered to be "respirable" or suitable for pulmonary delivery. A dry powder contains from about 0.1% to 10% moisture, and typically contains less than about 10 percent moisture, preferably less than 5% moisture, and more preferably contains less than about 3 percent moisture. Unless otherwise stated, a "dry powder composition for delivery to the deep lung" is one that, when aerosolized, is administered as dry powder particles.

"Follicle stimulating protein" or "FSP" means a protein or a mixture of proteins having structure and function similar to that of human follicle stimulating hormone ("hFSH"). FSP includes hFSH, amino acid analogs of hFSH ("hFSH analogs"), glycoforms of hFSH, glycoforms of hFSH analogs, and mixtures of proteins selected from hFSH, hFSH analogs, glycoforms of hFSH, and glycoforms of hFSH analogs.

FSH purified to various extents from human urine ("uFSH") is a mixture of proteins having structure and function similar to that of hFSH, and therefore is within the definition of FSP. UFSH is a mixture of hFSH and hFSH analogs, each also having heterogeneity of glycosylation.

So-called recombinant FSP ("rFSP") is a mixture of proteins having structure and function similar to that of hFSH and is biosynthesized in a host cell modified using recombinant or related techniques to express the hFSH amino acid sequence or the amino acid sequence of a hFSH analog [Keene, et al., *J. Biol. Chem.,* 264:4769–4775 (1989); Chappel, S., et al., *Proceedings of the 3rd World Congress on Gynocological Endocrinology,* 179–184 (1992); or Reddy, V. B., et al., U.S. Pat. No. 5,156,957, Oct. 20, 1992]. The heterogeneity of rFSH is caused by infidelity in transcription and heterogeneity of post-translational modifications characteristic of the host cell or resulting from culture conditions, purification, formulation, and storage, among other causes.

Structurally, hFSH is a heterodimeric glycoprotein consisting of two non-covalently bound subunits referred to as the alpha (α) and beta (β) subunits. The human FSH alpha subunit consists of a chain of 92 amino acids, five intrasubunit disulfide bonds, and two N-linked glycosyl side chains. The amino acid sequence of human FSH alpha subunit is given as SEQ ID NO:5 herein. The human FSH beta subunit consists of a chain of 111 amino acids, six intrasubunit disulfide bonds, and two N-linked glycosyl side chains. Its amino acid sequence is given as SEQ ID NO:6 herein. Disulfide bonds link residues 7 and 31, 10 and 60, 28 and 82, 32 and 84, and 59 and 87 in the hFSH alpha subunit, and they link residues 3 and 51, 17 and 66, 20 and 104, 28 and 82, 32 and 84, and 87 and 94 in the hFSH beta subunit.

The sites of N-glycosylation are at positions 52 and 78 in the α subunit (SEQ ID NO:5) and at residues 7 and 24 in the β subunit (SEQ ID NO:6). Together, the two subunits have a molecular weight of about 31 kD measured by mass spectroscopy and about 35–45 kD measured by PAGE or gel chromatography depending upon the state of glycosylation. Pertinent sequence information (along with references) can be found in the Entrez Protein Database, which is provided and maintained by the National Center for Biotechnology Information (NCBI). An illustrative protein sequence for the precursor α-subunit corresponds to, e.g., Entrez Accession No. 69160 (116 amino acids, of which the C-terminal 92 amino acids constitute the mature α-subunit sequence); representative sequences for the precursor β-subunit are identified by the following Entrez Accession Nos.: 120552, 476441, 182767, 182762, and 511854 (129 amino acids, of which the C-terminal 111 amino acids constitute the mature β-subunit sequence).

Functionally, the activity of FSP is determined as described herein for bioactive powders. “FSP activity,” “FSP bioactivity,” “FSH activity,” “FSH bioactivity,” and like concepts of functionality can be measured by heterodimer stability; activity in an FSH-related signal transduction assay; FSH receptor binding; a version of the Steelman/Pohley in vivo rat ovarian weight assay; in vivo pharmacokinetic measures, such as in vivo half-life; in vivo pharmacodynamic testing, as known in the art and as described herein, such as increased follicular growth. The specific activity of FSP contained in the dry powders of the invention may range from about 100–175 IU/mg protein (typical activity ranges for uFSH, which generally contains LH or other co-purified proteins) to about 1000 to 13,500 IU/mg protein for ultra-pure urinary FSH (Arpaia, et al., 1992) or recombinant material, and will depend upon the source and degree of purification of the hormone.

FSP is meant to include deglycosylated, unglycosylated, modified glycosylated, and other glycoforms. Glycosylated forms are preferred. Glycosylated FSP usually is heterogeneous to some extent in its glycosylation, having within any sample a multiplicity of glycosylated species. Glycosyl heterogeneity can be extensive depending on the type of cell in which the FSP was biosynthesized and on the conditions to which FSP was exposed post-translation, post-secretion, during purification and storage, as described by Baenziger and Green, *Biochem. Biophys. Acta,* 947, 287–306 (1998); Bishop, et al., *Mol. Endocrinol.,* 8, 722–731 (1994); Thotakura and Blithe, *Glycobiology,* 5, 3–10 (1995); Dahl, et al., *Science,* 239, 72–74 (1988); Ulloa-Aguirre, et al., *Endocr. Rev.,* 16, 765–787 (1995); Stanton, et al., *Endocrinology,* 130, 2820–2832 (1992); Beitens and Padmanabhan, *Trends Endocrinol. Metab.,* 2, 145–151 (1991); Hard, et al. *Eur. J. Biochem.,* 193, 1064–1069 (1990); Harris, et al., *Mol. Hum. Reprod.,* 2, 807–811 (1996); Hakola, et al., *Mol. Cell. Endocrinol.,* 127, 59–69 (1997). A glycoform is a form of glycoprotein having variation in the type or pattern of glycosylation compared with the type or pattern of glycosylation of hFSH. A glycoform can be thought of as a carbohydrate analog (as opposed to an amino acid analog).

FSP includes amino acid analogs of hFSH (i.e., hFSH analogs) such as those described in Monahan, M., et al., *Biochemistry,* 12:4616–4620 (1973); Nestor, J. J., et al., U.S. Pat. No. 4,234,571, Nov. 18, 1980; Fujino, M., et al., *J. Med. Chem.,* 16:1144–1147 (1973); Coy, D. H., et al., *Biochem. Biophys. Res. Commun.,* 67:576–582 (1975); Combarnous, Y., Endocrine Reviews, 13(4):670–691 (1992), and Antoni, F., et al., U.S. Pat. No. 4,552,864, Nov. 12, 1985. A hFSH analog is a compound structurally and functionally similar to hFSH, but differing structurally from hFSH in that one or more amino acids have been substituted, deleted, added, or otherwise modified compared with hFSH. A hFSH analog herein must exhibit at least 10% bioactivity by some measure compared with hFSH. Examples of hFSH analog subunits include, but are not limited to, those in SEQ ID NOS: 1–4 and 7–31. Amino acids in a FSH analog that are essential for function can be identified by methods known in the art, such as site-directed mutagenesis or alanine-scanning mutagenesis [Cunningham and Wells, *Science,* 244: 1081–1085 (1989)]. The latter procedure introduces single alanine mutations at every residue in the molecule. The resulting mutant molecules are then tested for biological activity. Sites that are critical for ligand-protein binding can also be identified by structural analysis such as crystallography, nuclear magnetic resonance spectroscopy, or photoaffinity labeling [Smith, et al., *J. Mol. Biol.,* 7224:899–904 (1992); de Vos, et al., *Science,* 255:306–312 (1992)].

Particularly preferred hFSH analogs for use in the present invention are “hFSH variants.” A hFSH variant is a FSP differing structurally from hFSH in that one or more amino acids are deleted from one or more of the four termini of hFSH (the alpha and beta subunits each have two termini, an N-terminus and a C-terminus). In hFSH variants, one or more amino acid additions, substitutions, or deletions may also be present internally, i.e., not at the termini, in the alpha subunit, the beta subunit, or both, compared with hFSH. Examples of amino acid sequences of hFSH variant α subunits include, but are not limited to, those in SEQ ID NOS:29–31, optionally comprising at least one further substitution, addition, or deletion. Examples of amino acid sequences of hFSH variant β subunits include, but are not limited to, those in SEQ ID NOS: 11–28, optionally comprising at least one further substitution, addition, or deletion. Certain variants are well known in the art as described in Hoffmann, J. A., et al., International Patent Publication WO 00/04913, Feb. 3, 2000.

Preferred hFSH variants are: 1) those wherein one or both subunits have terminal deletions, but wherein any deletions are limited to one, two, three, four, five, or six amino acids from the N-terminus of the alpha subunit, one, two, three, four, or five amino acids from the C-terminus of the alpha subunit, one or two amino acids from the N-terminus of the beta subunit, and one, two, three, four, five, six, or seven amino acids from the C-terminus of the beta subunit; 2) those wherein one or both subunits have one or more deletions described in 1) above except that the C-terminus of the alpha subunit does not have deletions; 3) those having deletions at the C-terminus of the beta subunit, and in that case more preferably those having at least three amino acids deleted from the C-terminus of the beta subunit; 4) those whose subunits have no deletions at the N-termini, or at most one or two amino acids deleted at the N-termini, and in that case more preferably at the N-terminus of the beta subunit; 5) those having an alpha subunit of full length (92 amino acids) combined with a variant beta subunit, preferably having one to seven amino acids deleted from the C-terminus and either no amino acids deleted from the N-terminus or one or two amino acids deleted from the N-terminus; all optionally having one or more deletions, substitutions, or additions of amino acids internally (i.e., not at the termini) as compared with hFSH. The most preferred hFSH variants are those comprised of an alpha subunit having the amino acid sequence of any one of SEQ ID NOS:5, 29–31 and a beta subunit having an amino acid sequence of any one of SEQ ID NOS:11–28, and those comprised of an alpha subunit having the amino acid sequence of any one of SEQ ID NOS:29–31 and a beta subunit having an amino acid sequence of SEQ ID NO:6.

For hFSH variant nomenclature herein, reference will be made to SEQ ID NO. or to the amino acids deleted, using either "des" followed by the position number(s) or by the three letter code(s) and position(s) of the deleted amino acid(s) (e.g., desAsn1) or by simply indicating the removed amino acid(s) in one or three letter code(s) and the affected position(s) (e.g., 1N or $Asn^1$). The SEQ ID NOS are identified in below.

| FSP SEQ ID NO: | DNA SEQ ID NO: | Subunit |
|---|---|---|
| 1 | — | Bovine α |
| 2 | — | Bovine β |
| 3 | — | Equine α |
| 4 | — | Equine β |
| 5 | 32, 37 | Human α |
| 6 | 36 | Human β |
| 7 | — | Porcine α |
| 8 | — | Porcine β |
| 9 | — | Ovine α |
| 10 | — | Ovine β |
| 11 | 33, 38 | Human β variant Des 109, 110, 111 |
| 12 | 34 | Human β variant Des 110, 111 |
| 13 | 35 | Human β variant Des 111 |
| 14 | 39 | Human β variant Des 108–111 |
| 15 | 40 | Human β variant Des 107–111 |
| 16 | 41 | Human β variant Des 106–111 |
| 17 | 42 | Human β variant Des 1, 111 |
| 18 | 43 | Human β variant Des 1, 2, 111 |
| 19 | 44 | Human β variant Des 1, 110, 111 |
| 20 | 45 | Human β variant Des 1, 2, 110, 111 |
| 21 | 46 | Human β variant Des 1, 109–111 |
| 22 | 47 | Human β variant Des 1, 2, 109–111 |
| 23 | 48 | Human β variant Des 1, 108–111 |
| 24 | 49 | Human β variant Des 1, 2, 108–111 |
| 25 | 50 | Human β variant Des 1, 107–111 |
| 26 | 51 | Human β variant Des 1, 2, 107–111 |
| 27 | 52 | Human β variant Des 1, 106–111 |
| 28 | 53 | Human β variant Des 1, 2, 106–111 |
| 29 | 54 | Human α variant Des $Ala^1$ |
| 30 | 55 | Human α variant $DesAla^1Pro^2$ |
| 31 | 56 | Human α variant $DesAla^1Pro^2Asp^3$ |

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size (e.g., electron microscopy, light scattering, and laser diffraction).

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

"Pharmaceutically acceptable excipient or carrier" refers to an excipient that can be taken into the lungs in association with FSH with no significant adverse toxicological effects to the subject, and particularly to the lungs of the subject.

"Pharmacologically effective amount" or "physiologically effective amount of FSP" is the amount of FSP present in a dry powder composition as described herein that is needed to provide a desired level of drug in the bloodstream of a subject to be treated to give an anticipated physiological response when such composition is administered by inhalation for deposition in and absorption from the lung. The precise amount will depend upon numerous factors, e.g., the source of FSP (urinary or recombinant), the specific activity of the composition, the delivery device employed, physical characteristics of the powder, its intended use, and patient considerations, and can readily be determined by one skilled in the art, based upon the information provided herein.

Before therapy, certain infertile female subjects will generally possess small follicles, i.e., follicles in each ovary's largest section which are less than 10 mm in diameter, typically determined by ultrasound performed using a vaginal probe. "Increased follicular growth," in the context of treatment for female infertility, is a level of follicular growth in a subject that is increased relative to its baseline level prior to administering an FSP dry powder composition of the invention. An increase in follicular growth is measured by an increase in the number of follicles having a mean diameter of 10 mm or greater. Preferably, increased follicular growth is indicated by 1 or more follicles demonstrating growth to a mean diameter of 10 mm or greater. In ovulation induction-type therapies, increased follicular growth is typically indicated by 1–2 follicles or more demonstrating growth to a mean diameter of 10 mm or greater. In super ovulation-type therapies (e.g., in-vitro fertilization), increased follicular growth is preferably indicated by 2 or more follicles demonstrating growth to a mean diameter of 10 mm or greater, more preferably 3 to 5 follicles having increased in size to a diameter of 10 mm or greater, and even more preferably 6 to 8 follicles or more exhibiting such size characteristics. Over the course of treatment (particularly super ovulation treatment), one indication of full follicular development in a subject is an average of 9 follicles or more having a diameter greater than 10 mm, where the largest growing follicle has matured to a mean diameter of greater than or equal to 16 mm. The efficacy of FSH therapy can also be evaluated by other methods, e.g., ultrasound and subject estradiol levels.

"Stabilized dry powder composition", particularly in reference to a dry powder for aerosolized delivery to the deep lung, is a powder which (i) contains FSH and an excipient material or materials, where the excipient is not melezitose, (ii) possesses a specific activity of at least 50 IU/mg FSH and more preferably a specific activity of at least 100 IU/mg FSH, and (iii) maintains at least about 70% of its initial bioactivity when stored for one month at room temperature under ambient conditions. That is to say, a stabilized dry powder in accordance with the invention is one that substantially maintains in vivo and/or in vitro FSH activity upon formulation and long term storage over a period of at least one month. Stabilized dry powder compositions containing a salt of a carboxylic acid having two or more ionizable protons (e.g. citrate, glutamate, tartrate, and the like) as a buffer are prepared by methods known in the art, but not by lyophilization.

"Polymeric macromolecule" is a high molecular weight polymeric compound that can be naturally occurring (e.g., proteins, carbohydrates, nucleic acids) or synthetically-produced (e.g., polyethylene glycols, polyvinylpyrrolidones, Ficolls, and the like, as known in the art.)

"Therapeutically effective amount" is the amount of FSP, which when delivered by inhalation for deposition in and absorption from the lung in the form of a dry powder composition as described herein, provides the desired biological effect.

"Cascade impactor efficiency" or "CI Eff" is the fraction of aerosolized powder recovered in the cascade impactor. CI Eff values are typically less than DDE values due to losses to the throat or walls of the cascade impactor.

"Percent left" means the percent of powder originally in a blister pack (BP) that remains in the BP after dispersion of the powder dose.

"Percent collected" means the percent of powder dispersed from a BP that deposits on a collection filter. "Percent collected" accounts for powder that may be lost to deposition in the device and chamber.

"Bulk density" refers to the density of a powder prior to compaction (i.e., density of an uncompressed powder), and is typically measured by a well-known USP method.

II. FSP Dry Powders

The present invention provides stable, dispersible dry powder compositions for pulmonary delivery of FSP. The compositions developed by the applicants overcome many of the problems often encountered heretofore in formulating proteins, particularly gonadotropin hormones, for delivery to the deep lung. The FSP dry powder compositions described herein are readily dispersed (i.e., demonstrate good aerosol performance), are stable against both physical and chemical degradation (i) in solution, before powder manufacture, (ii) during powder manufacture and processing, and (iii) upon storage, and exhibit good bioavailabilities when delivered by inhalation for deposition in and absorption from the lung. The dry powder compositions according to the present invention generally include FSP and a pharmaceutically acceptable excipient, although dry powders composed of neat FSP (i.e., respirable powders composed of FSP and essentially lacking any additional excipients or additives) are also envisioned. Components of FSP dry powders suitable for delivery to the deep lung will now be described.

A. Follicle Stimulating Proteins

1. Naturally occurring FSP. The FSP contained in the solid preparations may be at least partially purified from natural sources (i.e., may be highly purified and may optionally include LH or other co-purified proteins), such as human urinary FSH (uFSH). Urinary-derived FSH may be obtained from a commercial source (e.g., Vitro Diagnostics, Boulder, Colo.) or purified by immunopurification as described in Arpaia, G., et al., 1992. A number of naturally occurring FSP heterodimers are known and are suitable for use in the dry powder of the invention. Such exemplary FSP heterodimers, i.e., comprising one alpha subunit and one beta subunit, include but are not limited to SEQ ID NOS: 1 and 2 (bovine FSH); 3 and 4 (equine FSH); 5 and 6 (hFSH); 7 and 8 (porcine FSH); 9 and 10 (ovine FSH).

2. Synthetic or Recombinant FSP. Alternatively, FSP may be produced by chemical synthesis or may be biosynthesized in host cells appropriately engineered using conventional techniques of molecular biology (i.e., recombinant technology). Recombinant FSP, a preferred form of FSP for use in the dry powder compositions of the invention, may be prepared using conventional techniques such as those described in Keene, et al., 1989; Boime, et al., *Seminars in Reproductive Endocrinology,* 10:45–50 (1992); Chappel, et al., 1992; or Reddy, et al., 1992; Shome, B., et al., *J. Prot. Chem.,* 7:325–339 (1988); Saxena, B. B. and Rathnam, P., *J. Biol. Chem.,* 251:993–1005 (1976); Watkins, et al., DNA, 6:205–212 (1987); Shome, B. and Parlow, A. F., *J. Clin. Endocrizol. Metab.,* 39(1):203–205 (1974); Beck, et al., *DNA,* 4:76 (1985); Boime, et al., U.S. Pat. No. 5,405,945 (1995); and Reddy, V. B., et al., U.S. Pat. No. 5,639,640 (1997); Sambrook, et al. *Molecular Cloning: A Laboratory manual, 2nd Edition*, (1989); Ausubel, et al., Eds., *Current Protocols in Molecular Biology*, (1987–1998), Chapters 10, 12, 13, 16, 18 and 20, the contents of which are incorporated herein by reference. Exemplary preparations of FSH variants are provided in Examples 13,14,18 and 19.

More specifically, FSP products may be prepared by recombinant techniques in a prokaryotic or eucaryotic host, including, for example, bacterial, yeast, [Sherma, F., et al., *Methods in Yeast Genetics*, (1992)] higher plant, insect [Schneider, *J. Embryol. Exp. Morphol.,* 27:353–365 (1987)] and mammalian cells such as CHO, COS and Bowes melanoma cells. Depending upon the host employed in a recombinant production procedure, the rFSP molecules thus produced may be glycosylated or can be non-glycosylated. In addition, a rFSP subunit may also include an initiating methionine residue. Such methods are described in many standard laboratory manuals.

FSP may be expressed in modified forms, such as a fusion protein, and can include not only secretion signals, but also additional heterologous functional regions. For instance, a region of additional amino acids, particularly charged amino acids, can be added to the N-terminus to improve stability and persistence in the host cell, during purification, or during subsequent handling and storage. Also, peptide moieties can be added to an FSP molecule to facilitate purification. Such regions can be removed prior to final preparation of a polypeptide. Such methods are described in many standard laboratory manuals, such as Sambrook, supra, Chapters 17.29–17.42 and 18.1–18.74; Ausubel, supra, Chapters 16, 17 and 18.

Briefly, the expression of isolated nucleic acids encoding a FSP used in the present invention will typically be achieved by operably linking, for example, the DNA or cDNA to a promoter (which is either constitutive or inducible), followed by incorporation into an expression vector. The vectors can be suitable for replication and integration in either prokaryotes or eucaryotes. Typical expression vectors contain transcription and translation terminators, initiation sequences and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator.

Expression of a FSP in yeast cells is carried out by well-known methods [Sherma, et al., (1982)]. Two widely utilized yeast for production of eucaryotic proteins are *Saccharomyces cerevisiae* and *Pichia*. Vectors, strains, and protocols for expression in *Saccharomzyces* and *Pichia* are known in the art and available from commercial suppliers (e.g., Invitrogen, Inc.). Suitable vectors usually have expression control sequences, such as promoters, including 3-phosphoglycerate kinase or alcohol oxidase, and an origin of replication, termination sequences and the like.

Polynucleotide sequences encoding FSP can also be ligated to various expression vectors for use in transfecting mammalian cells. Mammalian cell systems often will be in the form of monolayers of cells although mammalian cell suspensions may also be used. A number of suitable host cell lines capable of expressing FSP include the HEK293, BHK21, AV12 and CHO cell lines. Expression vectors for these cells can include expression control sequences, such as an origin of replication, a promoter (e.g., CMV promoter, EF1 alpha promoter, or a HSV tk promoter or phosphoglycerate kinase promoter), an enhancer, and processing information sites, such as ribosome binding sites, RNA splice sites, polyadenylation sites (e.g., an SV40 large T Ag poly A addition site), and transcriptional terminator sequences. Other animal cells useful for production of FSP are available, for instance, from the American Type Culture Collection Catalogue of Cell Lines and Hybridomas (7th edition, 1992).

Appropriate vectors for expressing FSP in insect cells are usually derived from the SF9 baculovirus. Suitable insect cell lines include mosquito larvae, silkworm, armyworm, moth and *Drosophila* cell lines such as a Schneider cell line [Schneider, supra, 1987].

Introduction of a vector construct into a host cell can be effected by calcium phosphate transfection, DEAE-dextran mediated transfection, cationic lipid-mediated transfection, electroporation, transduction, infection or other methods. Such methods are described in many standard laboratory manuals, such as Sambrook, supra, Chapters 1–4 and 16–18; Ausubel, supra, Chapters 1, 9, 13, 15, 16, entirely incorporated herein by reference.

Alternatively, polynucleic acids encoding FSP can be expressed in host cells by introducing, by homologous recombination into the cellular genome at a preselected site, DNA which includes at least a regulatory sequence, an exon and a splice donor site. These components are introduced into the chromosomal (genomic) DNA in such a manner that this, in effect, results in production of a new transcription unit (in which the regulatory sequence, the exon and the splice donor site present in the DNA construct are operatively linked to the endogenous gene). As a result of introduction of these components into the chromosomal DNA, the expression of the desired endogenous gene is altered. Such methods are well known in the art, e.g., as described in U.S. Pat. Nos. 5,580,734, 5,641,670, 5,733,746, and 5,733,761, entirely incorporated herein by reference.

Recombinant FSP can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, reverse phase chromatography, dye chromatography and lectin chromatography. Monitoring of the purification process can be accomplished by using Western blot techniques or radioimmunoassay or other standard immunoassay techniques.

3. hFSH Variants. The dry powder composition of the invention may contain a hFSH variant. hFSH variants can be produced by a number of techniques well known to those skilled in the art such as by chemical synthesis, recombinant biosynthesis, and in vivo or in vitro processing of naturally occurring or recombinant FSH by amino- and/or carboxypeptidases to expose one or more internal amino acids.

B. Nucleic Acid Molecules Encoding FSP

Polynucleic acid molecules encoding FSP described herein are illustrative, not limiting, of sequences useful for preparing FSP by recombinant expression and they may be incorporated into the dry powder compositions of the invention, for expression of FSP in vivo, as described in greater detail below. Other polynucleic acids may be used to produce FSP without affecting the present invention. The polynucleic acid molecules can be in the form of RNA, such as mRNA, hnRNA, or any other form, or in the form of DNA, including, but not limited to, cDNA and genomic DNA obtained by cloning or produced synthetically, or any combination thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated polynucleic acid molecules for use in expressing a FSP comprise an open reading frame (ORF) shown in at least one of SEQ ID NOS: 32, 37, 54, 55, or 56, or a nucleic acid molecule having a sequence complementary thereto, for expressing an alpha subunit, or comprise an ORF in at least one of SEQ ID NO:33, 34, 35, 38, 39, 40, 41, 42, 43, 44, 45, 46, 47, 48, 49, 50, 51, 52, or 53, or a nucleic acid molecule having a sequence complementary thereto, for expressing a beta subunit.

The polynucleic acid sequences can be made using (a) standard recombinant methods, (b) synthetic techniques, (c) purification techniques, or combinations thereof, as well known in the art. The polynucleic acids may conveniently comprise sequences in addition to those exemplary sequences provided herein. For example, a multi-cloning site comprising one or more endonuclease restriction sites may be inserted into the nucleic acid to aid in isolation of the polynucleotide. Also, translatable sequences may be inserted to aid in the isolation of a translated FSH polynucleotide. Additional sequences may be added to such cloning and/or expression sequences to optimize their function in cloning and/or expression, to aid in isolation of an FSP polynucleotide, or to improve the introduction of the polynucleotide into a cell.

Polynucleic acids encoding FSP can be prepared by direct chemical synthesis methods such as the phosphotriester method of Narang, et al., *Meth. Enzymol.,* 68:90–99 (1979); the phosphodiester method of Brown et al., *Meth. Enzymol.,* 68:109–151 (1979); the diethylphosphoramidite method of Beaucage et al., *Tetra. Letts.,* 22:1859–1862 (1981); the solid phase phosphoramidite triester method described by Beaucage and Caruthers, *Tetra. Letts.,* 22(20):1859–1862 (1981), e.g., using an automated synthesizer, e.g., as described in Needham-VanDevanter, et al., *Nucleic Acids Res.,* 12:6159–6168 (1984); and the solid support method of U.S. Pat. No. 4,458,066. Chemical synthesis generally produces a single-stranded oligonucleotide, which may be converted into double-stranded DNA by hybridization with a complementary sequence, or by polymerization with a DNA polymerase using the single strand as a template. Although chemical synthesis of DNA is limited to sequences of about 100 bases, longer sequences may be obtained by the ligation of shorter sequences.

Representative polynucleotide sequences described in sequences 32–56 herein encode either an alpha or a beta subunit. The DNA of SEQ ID NO: 37 and 38 is designed and constructed from ligated oligonucleotides. The differences between SEQ ID NO: 32 and SEQ ID NO: 37 do not change the encoded amino acid sequence of the alpha subunit protein. Likewise, the differences between SEQ ID NO: 38 and SEQ ID NO: 33 do not change the encoded amino acid sequence of the beta variant subunit protein. The skilled person will know a multitude of sequences equivalent to the sequences described in SEQ ID NO: 32–56 exist because of the degeneracy of the genetic code.

The dry powder of the invention may contain a polynucleotide encoding FSP (e.g., genes encoding both the α- and β-subunits of FSP), a fragment thereof (e.g., the β-subunit, which confers biological specificity), and/or a variant as described herein, where the polynucleotide or FSP-coding region is operably linked to suitable transcriptional regulatory or control sequences (e.g., promoters, enhancers, and the like) to permit FSP transgene expression in target host cells of a subject, e.g., mammalian cells from the pulmonary regions of the lung (e.g., lung epithelial cells, alveolar type cells), or other suitable subject host cells. In addition to the sequences provided herein, representative gene sequences encoding FSP, its subunits, or precursor proteins, are found, for example, in the Entrez Nucleotide Database (as described above). Such exemplary coding sequences have the following Accession Nos.: J00152 V00487 (α subunit, bases 1–397), M54912 M38644 M21219 M18536 (β-subunit gene, exon 1), M54913 M21220 M18536 (β-subunit gene, exon 2), M54914 M38646 M21221 M18536 (β-subunit gene, exon 3).

In a preferred embodiment of this aspect of the invention, regulatory sequences operably linked to a polynucleotide coding sequence will function to express FSP in a pulsatile fashion. Polynucleotides encoding FSP may optionally be contained in a viral or other conventional gene therapy vector, or may comprise a lipid-FSP transgene complex, as described in Eljamal, M., et al., International Patent Publication WO 96/32116, Oct. 17, 1996; in McDonald, R. J., et al., *Pharm. Res.*, 15(5):671–9 (1998), and in Eastman, et. al., *Hum. Gene Ther.*, 8(6):765–73 (1997), the contents of which are expressly incorporated herein by reference. Generally, FSP expression levels in the target tissue will roughly correspond to the quantities of FSP described herein for direct incorporation into the dry powders of the invention; such expression levels will characteristically correspond to a therapeutically effective amount of FSP. Representative quantities of nucleic acid constructs for incorporation in the dry powders of the invention for achieving the desired expression levels are described in Eljamal, M., et al., ibid.

C. Excipients and Other Additives

In the powders of the invention, FSP is generally combined with one or more pharmaceutical excipients that are suitable for respiratory and pulmonary administration. Such excipients may serve simply as bulking agents when it is desired to reduce the active agent concentration in the powder that is being delivered to a patient. An excipient may also serve to improve the dispersibility of the powder within a powder dispersion device in order to provide more efficient and reproducible delivery of the active agent and to improve the handling characteristics of the active agent (e.g., flowability and consistency) to facilitate manufacturing and powder filling into unit dosage forms. In particular, the excipient materials can often function to improve the physical and chemical stability of FSP, to minimize the residual moisture content, hinder moisture uptake, and to regulate particle size, degree of aggregation, particle surface properties (i.e., rugosity), ease of inhalation, and targeting of the resultant particles to the deep lung.

Alternatively, FSP may be formulated in an essentially neat form, wherein the composition contains FSP particles within the requisite size range and substantially free from other biologically active components, pharmaceutical excipients, and the like.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers such as Ficolls), which may be present singly or in combination. Preferred are excipients that are soluble in either water (e.g., sugars, peptides, amino acids, and salts), alcohol (such as pectin, lecithin, povidone) or acetone (e.g., citric acid, PLGA). Also preferred are excipients having a glass transition temperature (Tg), above about 35° C., preferably above about 45° C., more preferably above about 55° C. Illustrative excipients suitable for use in the FSP dry powders of the invention include those disclosed in Inhale Therapeutic Systems' International Patent Application No. WO98/16207.

Exemplary protein excipients include but are not limited to serum albumin such as human serum albumin (HSA), recombinant human albumin (rHA), gelatin, casein, hemoglobin, and the like. Polypeptides and proteins suitable for use in the dry powder composition of the invention are provided in Inhale Therapeutic Systems' International Patent Publication No. WO96/32096. HSA is a preferred proteinaceous excipient, and has been shown to increase the dispensability of dry powders for aerosolized delivery to the lungs (WO 96/32096, ibid).

Representative amino acid/polypeptide components, which may optionally function in a buffering capacity, include alanine, glycine, arginine, betaine, histidine, glutamic acid, aspartic acid, cysteine, lysine, leucine, isoleucine, valine, methionine, phenylalanine, aspartame, threonine, tyrosine, tryptophan and the like. Preferred are amino acids and peptides that function as dispersing agents. Amino acids falling into this category include hydrophobic amino acids such as leucine (leu), valine (val), isoleucine (isoleu), norleucine (nie), tryptophan (try), alanine (ala), methionine (met), phenylalanine (phe), tyrosine (tyr), histidine (his), and proline (pro). Examplary FSP formulations containing a variety of amino acid excipients are provided in Example 23. Leucine is one particularly preferred amino acid excipient for the FSP compositions described herein. Leucine, when used in the formulations described herein includes D-leucine, L-leucine, and racemic leucine. Exemplary FSP dry powders containing leucine are described in Examples 11, 21, 22 and 23. Dispersibility enhancing peptides for use in the invention include dimers, trimers, tetramers, and pentamers composed of hydrophobic amino acid components such as those described above, e.g., dileucine, trileucine, and the like.

Carbohydrate excipients suitable for use in the invention exclude melezitose and include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, maltodextrins, dextrans, starches, and the like; and alditols, such as mannitol, xylitol, maltitol, lactitol, xylitol, sorbitol (glucitol), myoinositol and the like. Preferred carbohydrate excipients for use in the present invention are mannitol, trehalose, and raffinose. Preferred powder compositions in accordance with the invention are those that are stable in the absence of sucrose, and particularly those that are stable in the absence of combinations of sucrose and glycine.

The dry powder compositions may also include a buffer or a pH-adjusting agent. Typically, the buffer is a salt prepared from an organic acid or base. Representative buffers include salts of citric acid, ascorbic acid, gluconic acid, carbonic acid, tartaric acid, succinic acid, acetic acid, or phthalic acid and Tris, tromethamine hydrochloride, or phosphate buffers. Preferred buffers for use in the present compositions are organic acid salts such as citrate.

Additionally, the FSP dry powders of the invention may include polymeric excipients such as polyvinylpyrrolidones, Ficolls (a polymeric sugar), hydroxyethyl starch, dextrates, polyamino acids (e.g., polyleucine, polyglutamic acid), and/or polyethylene glycols, where such polymers are present as additives rather than as encapsulating agents. The dry powder may also optionally contain flavoring agents, antimicrobial agents, sweeteners, antioxidants, antistatic agents, steroids (e.g., cholesterol), and chelating agents (e.g., EDTA). Other pharmaceutical excipients and/or additives suitable for use in the FSP compositions according to the invention are listed in Remington, *The Science & Practice of Pharmacy*, $19^{th}$ *ed*., (1995), and in the *Physician's Desk Reference*, $52^{nd}$ *ed*., (1998), the disclosures of which are herein incorporated by reference.

In contrast to previously reported dry powders that are poorly absorbed into the pulmonary vasculature and into the systemic circulation when lacking one or more enhancer compounds [Backstrom, et al., U.S. Pat. No. 5,128,453, Jul. 7, 1992], the dry powder of the invention is surprisingly well-absorbed through the lung, and does not require the addition of absorption enhancers. This is evidenced by the bioavailability data provided herein, e.g., in Examples 10 and 17. Thus, the dry powders of the invention preferably lack typical enhancer compounds, such as surfactants (e.g., salts of a fatty acids), bile salts, alkyl glycosides, cyclodextrins, and phospholipids, or, if such compounds are present, they are typically present in very low concentrations—less than about 20% by weight relative to FSP, and more preferably less than about 15% to 10% by weight relative to FSP—such that they do not function to noticeably enhance absorption.

Preferred carrier or excipient materials are carbohydrates (e.g., saccharides and alditols) and buffers (e.g., citrate) or polymeric agents, optionally in combination with an amino acid or di- or tripeptide as described above.

In accordance with the invention, the solid state matrix formed by the excipient and the protein imparts a stabilizing environment to the FSP, and may optionally aid in dispersivity of the composition. The stabilizing matrix may be crystalline, an amorphous glass, or a mixture of both forms. Preferred are compositions that, irrespective of their percent crystallinity, are stable with respect to this percentage over time. Most suitable are dry powder formulations which are substantially amorphous (glasses) or substantially crystalline (i.e., are crystalline to the greatest extent possible, after adjusting for the amount of FSP contained in the powder, since FSH does not crystallize). More generally, preferred powders are substantially crystalline, such as FSP powder L2017 (Example 6.C.), i.e., 51 to 99% crystalline, 60% to 95% crystalline, 65% to 90% crystalline, or any range or value therein, or are substantially amorphous glasses, such as powders L2010 and L2018 (Example 6.C.), i.e., at least about 70% of the solid is an amorphous glass, preferably at least about 75% is an amorphous glass, and more preferably at least about 85% is an amorphous glass.

For FSP dry powder formulations which are substantially amorphous, preferred are those formulations exhibiting glass transition temperatures ($T_g$) above about 30° C., preferably above about 40° C., and more preferably above about 60° C. Glass transition temperatures for representative FSP dry powder compositions are presented in Table 6 (Example 6.B.) As can be seen from the values presented therein, for those compositions for which Tg values were determined, 22 formulations/lot numbers exhibited Tg values above 30° C., while 19 formulations/lot numbers possessed Tg values about 60° C. Formulations having Tg values at or above 60° C. included the following: L2001, L2004, L2006, L2008, L2009, L2010, L2012, L2013, L2014, L2016, L2020 and L2018. Preferred storage temperatures for substantially amorphous powders are at least about 10° C. lower than the $T_g$ of the composition, as set forth in Inhale Therapeutic Systems' International Patent Publication WO 98/16205.

FSP contained in the dry powder formulations is present in a quantity sufficient to form a pharmacologically effective amount when administered by inhalation to the lung. The dry powders of the invention will generally contain from about 0.1% by weight to about 99.9% by weight FSP, more typically from about 0.5 to 80% by weight FSP, and preferably from about 1 to 75% by weight FSP. Preferred compositions contain from about 1.5 to 70% FSP, and more preferably from about 12 to 60% by weight FSP, depending upon the specific activity of FSP contained in the formulation and the type of treatment (i.e., ovulation induction versus super ovulation therapy). In one preferred embodiment of the invention, the dry powder contains about 5% by weight FSP. In an alternate embodiment, the dry powder contains about 15% by weight FSP. Correspondingly, the amount of excipient material(s) will range from about 99.9 to 0.1% by weight, more typically from about 99.50% to 20% by weight, and preferably from about 99% to 25% by weight. Preferred compositions contain from about 98.5 to 30% by weight excipient material, and more preferably contain from about 88 to 40% by weight excipient material. Leucine-containing FSP powders will typically contain from about 15–85% by weight leucine, preferably from about 20–80% by weight leucine, and more preferably from about 40–60% by weight leucine.

The composition of representative FSP dry powders for pulmonary delivery is provided at least in Examples 2 and 11. As can be seen from the data provided in Example 2, Table 1, compositions containing various combinations and relative amounts of FSP and excipient(s) resulted in powders having good particle size characteristics (all powders possessed MMDs less than 3.5 microns, while 80 percent of powders possessed MMDs less than 1.5 microns) and which exhibited a minimal change in higher order aggregate formation of FSP upon powder manufacture (Example 3). The findings detailed in Example 3 provide evidence of another surprising feature of the FSP compositions of the invention, i.e., their ability to stabilize monomeric FSP against higher order aggregate formation during powder manufacture and processing. This is important, since the formation of higher order aggregates of FSP can adversely affect its bioactivity, due to impaired receptor binding, which will in turn reduce the potency of the resultant powders.

III. Preparing FSP Dry Powders

Dry powder FSP formulations are preferably prepared by spray drying under conditions that result in a substantially amorphous glassy or a substantially crystalline bioactive powder as described above. Spray drying of the FSP-solution formulations is carried out, for example, as described generally in the *Spray Drying Handbook, 5th ed.*, (1991), and in Platz, R., et al., International Patent Publication No. WO 97/41833, Nov. 13, 1997.

To prepare an FSP solution for spray drying, FSP is generally dissolved in a physiologically acceptable aqueous buffer, e.g., a citrate buffer or a citrate glycine buffer, typically having a pH range from about 2 to 9. The pH range of pre-dried solutions is generally maintained between about 4 and 10, with near neutral pH being preferred, since such pHs may aid in maintaining the bioactivity or physiological compatibility of the powder after dissolution of powder within the lung. The aqueous formulation may optionally contain additional water-miscible solvents, such as alcohols and the like. Representative alcohols include methanol, ethanol, propanol, isopropanol, and the like. FSP solutions will generally contain FSP dissolved at a concentration from 0.01% (weight/volume) to about 10% (weight/volume), usually from 0.1% to 1% (weight/volume).

In turning now to the results provided in Example 1, it can be seen that representative solution formulations of FSP prior to spray drying showed no appreciable decline in bioactivity upon storage for several days, and after repeated freeze-thaw cycles, indicating the relatively high stability of such solution formulations.

The FSP-containing solutions are then spray dried in a conventional spray drier, such as those available from commercial suppliers such as Niro A/S (Denmark), Buchi (Switzerland) and the like, resulting in a stable, FSP dry powder. Optimal conditions for spray drying the FSP solutions will vary depending upon the formulation components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause deactivation of FSP in the sprayed material. Such temperatures are typically determined experimentally, although generally, the inlet temperature will range from about 50° C. to about 200° C. while the outlet temperature will range from about 30° C. to about 150° C.

Alternatively, FSP dry powders may be prepared by first drying a solution containing FSP and exciptient(s) by lyophilization, vacuum drying, spray freeze drying, super critical fluid processing, or other forms of evaporative drying, and then further processing the dry material to obtain a FSP dry powder having aerosol properties suitable for administration into the deep lung and an acceptable ED, by blending, grinding or jet milling the dried formulation. In some instances, it is desirable to make FSP dry powder formulations possessing improved handling/processing characteristics, e.g., reduced static, better flowability, low caking, and the like, by preparing compositions composed of fine particle aggregates, that is, aggregates or agglomerates of the above-described FSP dry powder particles, where the aggregates are readily broken back down to the fine powder components for pulmonary delivery, as described, e.g., Johnson, et al., U.S. Pat. No. 5,654,007, Aug. 5, 1997, incorporated herein by reference. Alternatively, the FSP powders may be prepared by agglomerating the powder components, sieving the materials to obtain the agglomerates, spheronizing to provide a more spherical agglomerate, and sizing to obtain a uniformly-sized product, as described, e.g., and in Ahlneck, C.; et al., International PCT Publication No. WO95/09616, Apr. 13, 1995, incorporated herein by reference. The FSP dry powders of the invention may also be prepared by blending, grinding or jet milling formulation components directly in dry powder form. The FSP dry powders are preferably maintained under dry (i.e., relatively low humidity) conditions during manufacture, processing, and storage.

Irrespective of the drying process employed, the process will preferably result in particles composed of FSP in non-aggregated form, or having an extent of higher order aggregate formation that is substantially unchanged from that observed in the pre-dried material, as illustrated in Example 3. Moreover, processes suitable for preparing the FSP formulations of the invention are those in which the bioactivity of the FSP is not adversely affected, i.e., the bioactivity of the resulting powder is reduced by no more than about 40–50%, preferably by no more than about 30–40%, and more preferably by no more than about 15%–30% in comparison to the bioactivity of the FSP formulation prior to drying/sizing. Illustrative FSP dry powders which exhibited no significant loss in bioactivity upon drying are described in Example 8.

Provided in Example 2, and more specifically in Table 1, are exemplary FSP compositions in accordance with the invention. As can be seen, FSP dry powders were obtained in high yields, typically between about 70 and 80%, illustrating the ability to reproducibly prepare large quantities of FSP dry powders suitable for pulmonary delivery. Moreover, the extent of FSP sialylation was shown to be unaffected by spray drying (Example 5), illustrating the chemical stability of FSP under conventional spray drying conditions. This is important since the prolonged bioactive half-life of FSP is a result of its oligosaccharide content; FSP asialoglycoproteins (i.e., proteins stripped of sialic acid) are cleared rapidly by the liver.

IV. Features of FSP Dry Powders

The FSP powders of the invention are further characterized by several features, most notably, the ability of the powder to penetrate to the tissues of the lower respiratory tract (i.e., the alveoli) for subsequent entry into the bloodstream (see, e.g., Examples 10 and 18). It has been found that certain physical characteristics of the FSP dry powders, to be described more fully below, are important in maximizing the efficiency of aerosolized delivery of such powders to the deep lung. The FSP dry powders are composed of particles effective to penetrate into the alveoli of the lungs, that is, having a mass median diameter (MMD) from about 0.1 to 20 μm. Typically, the MMD of the particles is less than about 10 μm (e.g., ranging from about 0.1 to 10 μm), preferably less than 7.5 μm (e.g., ranging from about 0.5 to 7 microns), and most preferably less than 5 μm, and usually being in the range of 0.1 μm to 5 μm in diameter. Preferred powders are composed of particles having an MMD from about 1 to 3.5 μm. Numerous examples of respirable FSP powders of varying concentrations of active agent and excipients and composed of particles within this preferred size range have been prepared (e.g., Table 1, column 10; Example 2). In some cases, the FSP powder will also contain non-respirable carrier particles such as lactose, where the non-respirable particles are typically greater than about 40 microns in size.

The FSP powders of the invention are further characterized by an aerosol particle size distribution less than about 10 μm mass median aerodynamic diameter (MMAD), and preferably less than 5 μm, and more preferably less than about 3.5 μm. The mass median aerodynamic diameters of the powders will characteristically range from about 0.5–5.0 μm, preferably from about 1.0–4.0 μm MMAD, more preferably from about 1.5–3.5 μm MMAD, and even more preferably from about 1.5 to 3.0 μM. To further illustrate the ability to prepare FSP powders having an aerosol particle size distribution within a range suitable for pulmonary administration, exemplary FSP dry powders composed of particles having an aerosol particle size distribution less than about 5 μm MMAD, and more specifically, characterized by MMAD values less than 3.5 μm, are illustrated in Table 8 (Example 7), in Table 16 (Example 11), in Table 30 (Example 21) and in Table 31 (Example 22).

FSP dry powders of the invention are characterized, in another respect, by a relative pulmonary bioavailability between about 1% to 60%. The relative pulmonary bioavailability of a powder of the invention will typically fall between about: 1–60%, 1–30%, 5–30%, 10–30%, 15–30%, 15–25%, 20–25%, 1–20%, 2–20%, 3–20%, 4–20%, 1–15%, 1–10%, 2–10%, 3–10% and 4–10%. Preferably, an FSP powder will exhibit a relative pulmonary bioavailability between about 1–30% and more preferably between about 1–20%, as supported by the data provided herein.

The FSP dry powders generally have moisture content below about 10% by weight, usually below about 5% by weight, and preferably below about 3% by weight. Such low moisture-containing solids tend to exhibit a reduced tendency towards degradation of protein. The moisture content of representative FSP dry powders prepared as described herein is provided in Example 6.B., Table 6.

The delivered dose efficiency (DDE) of these powders is greater than 30% and usually greater than 40%. More preferably, the DDE of the FSP powders of the invention is greater than 50%, and is often greater than 55%. Even more preferably, the DDE of an FSP powder is greater than 60%. Highly preferred are powders having DDE values greater than 70%, and even more preferred are powders having DDE values greater than about 75%. In looking at Example 7, Table 7, and Example 11, Tables 14 and 15, it can be seen that the applicants have successfully prepared a large number of representative FSP dry powders with DDE values greater than or equal to 50%. Formulations which exhibited and maintained particularly good powder dispersibilities, as indicated by their DDE values, included L2001, L2005, L2006, L2008, L2010, L2012, L2014, L2016, L2017, L2018, and L2020, the compositions of which are provided in Table 6, and 99348, 99349, 99423, 99425, 99426, 99455, 99454, and 99457 (Tables 14, 15).

The FSP powders of the invention will typically possess a bulk density value ranging from about 0.10 to 10 gram/cubic centimeter, preferably from about 0.15 to 5 gram/cubic centimeter, more preferably from about 0.15 to 4.0 grams/cubic centimeter, even more preferably from about 0.17 to 1 gram/cubic centimeter, even more preferably from about 0.17–0.75 gram/cubic centimeter, and most preferably from about 0.2 to 0.75 gram/cubic centimeter.

Powders of the invention will possess a wide range of specific bioactivity values, depending upon the type of FSP (e.g., impure FSP mixtures containing FHP and other proteins versus highly purified forms of FSP) contained in the powder. Powders of the invention will generally possess a specific bioactivity greater than 100 IU per gram of powder. In most instances, the specific bioactivity of the FSP powder is: greater than 250 IU per gram of powder, greater than 500 IU per gram of powder, greater than 1,000 IU per gram of powder, greater than 2,000 IU per gram of powder, greater than 5,000 IU per gram of powder, greater than 10,000 IU per gram of powder, greater than 25,000 IU per gram of powder, greater than 50,000 IU per gram of powder, greater than 100,000 IU per gram of powder, greater than 250,000 IU per gram of powder, greater than 500,000 IU per gram of powder, greater than 1,000,000 per gram of powder, greater than 2,500,000 IU per gram of powder, greater than 5,000,000 IU per gram of powder, or greater than 10,000,000 IU per gram of powder.

An additional measure for characterizing the overall aerosol performance of a dry powder is the aerosol performance coefficient (APC). The APC value for FSP powders as described herein is greater than 0.10, typically greater than 0.15, and more preferably greater than 0.25. As can be seen from the APC values provided in Tables 8 and 14, FSP dry powders have been prepared which are particularly well suited for pulmonary delivery, as evidenced by APC values greater than 0.25. Such powders contain a large proportion of small aerosol particle sizes and are thus extremely effective when delivered aerosolized form, in (i) reaching the alveolar region of the lung, followed by (ii) diffusion to the interstitium and (iii) subsequent passage into the bloodstream through the endothelium.

V. Pulmonary Administration of FSP Compositions

The FSP dry powder formulations described herein may be delivered using any suitable dry powder inhaler (DPI), i.e., an inhaler device that utilizes the patient's inhaled breath as a vehicle to transport the dry powder drug to the lungs. Preferred are Inhale Therapeutic Systems' dry powder inhalation devices as described in Patton, J. S., et al., U.S. Pat. No. 5,458,135, Oct. 17, 1995; Smith, A. E., et al., U.S. Pat. No. 5,740,794, Apr. 21, 1998; and in Smith, A. E., et. al., U.S. Pat. No. 5,785,049, Jul. 28, 1998, herein incorporated by reference. When administered using a device of this type, the powdered medicament is contained in a receptacle having a puncturable lid or other access surface, preferably a blister package or cartridge, where the receptacle may contain a single dosage unit or multiple dosage units. Convenient methods for filling large numbers of cavities (i.e., unit dose packages) with metered doses of dry powder medicament are described, e.g., in Parks, D. J., et al., International Patent Publication WO 97/41031, Nov. 6, 1997, incorporated herein by reference.

Also suitable for delivering the FSP powders described herein are dry powder inhalers of the type described, for example, in Cocozza, S., et al., U.S. Pat. No. 3,906,950, Sep. 23, 1974, and in Cocozza, S., et al., U.S. Pat. No. 4,013,075, Mar. 22, 1977, incorporated herein by reference, wherein a pre-measured dose of FSP dry powder for delivery to a subject is contained within a hard gelatin capsule.

Other dry powder dispersion devices for pulmonary administration of FSP dry powders include those described, for example, in Newell, R. E., et al. European Patent No. EP 129985, Sep. 7, 1988); in Hodson, P. D., et al., European Patent No. EP472598, Jul. 3, 1996; in Cocozza, S., et al., European Patent No. EP 467172, Apr. 6, 1994, and in Lloyd, L. J. et al., U.S. Pat. No. 5,522,385, Jun. 4, 1996, incorporated herein by reference. Also suitable for delivering the FSP dry powders of the invention are inhalation devices such as the Astra-Draco "TURBUHALER". This type of device is described in detail in Virtanen, R., U.S. Pat. No. 4,668,218, May 26, 1987; in Wetterlin, K., et al. U.S. Pat. No. 4,667,668, May 26, 1987; and in Wetterlin, K., et al., U.S. Pat. No. 4,805,811, Feb. 21, 1989, all of which are incorporated herein by reference. Other suitable devices include dry powder inhalers such as Rotahaler® (Glaxo), Discus® (Glaxo), Spiros™ inhaler (Dura Pharmaceuticals), and the Spinhaler® (Fisons). Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in Mulhauser, P., et al., U.S. Pat. No. 5,388,572, Sep. 30, 1997, incorporated herein by reference.

The FSP dry powders may also be delivered using a pressurized, metered dose inhaler (MDI), e.g., the Ventolin® metered dose inhaler, containing a solution or suspension of drug in a pharmaceutically inert liquid propellant, e.g., a chlorofluorocarbon or fluorocarbon, as described in Laube, et al., U.S. Pat. No. 5,320,094, Jun. 14, 1994, and in Rubsamen, R. M., et al, U.S. Pat. No. 5,672,581 (1994), both incorporated herein by reference. When administered by a metered dose inhaler, the FSP composition is preferably absent a surfactant (e.g., fatty acids, bile salts, phospholipids, or alkyl saccharides) for enhancing the systemic absorption of FSP, since, when administering the compositions of the invention, such compounds are unnecessary for achieving therapeutic levels of FSP in the bloodstream.

Alternatively, the powders described herein may be dissolved or suspended in a solvent, e.g., water or saline, and administered by nebulization. Nebulizers for delivering an aerosolized solution include the AERx™ (Aradigm), the Ultravent® (Mallinkrodt), and the Acorn II® (Marquest Medical Products).

Prior to use, the FSP dry powders are generally stored under ambient conditions, and preferably are stored at a temperature at or below about 25° C., and relative humidity (RH) ranging from about 30 to 60%. More preferred relative humidity conditions, e.g., less than about 30%, may be achieved by the incorporation of a desiccating agent in the secondary packaging of the dosage form. The FSP powders of the invention demonstrate no significant loss of bioactivity upon storage; moreover, accelerated stability studies carried out on three representative dry powder formulations (Example 7.C., Table 9, and FIG. 1) illustrate the ability to prepare respirable FSP dry powders characterized not only by good aerosol performance, but having good stability, as well. Moreover, both preliminary in vitro results for intratracheally administered FSP solutions in rats (Example 9) and pulmonary administration of FSP powders to monkeys (Examples 10 and 17) revealed reasonably high bioavailability values, i.e., from about 5% to 20% and from 18% to 26%, relative to administered subcutaneously FSP, further indicating the operability of treating infertility by pulmonary administration of dry powders of the present invention.

VI. Therapeutic Applications

The FSP dry powder of the invention is useful, when administered by inhalation for deposition in and absorption from the lung in a therapeutically effective amount, for treating infertility in both male and female subjects. More specifically, the methods of the present invention are particularly useful in therapeutic applications for the treatment of patients who are deficient in, or could otherwise benefit from, levels of FSP that are augmented over those produced endogenously.

When inhaled into the deep lung in dry powder form, FSP is effective to stimulate ovarian follicular growth in women who are not suffering from primary ovarian failure. Following pulmonary delivery of FSP, measurement of plasma inhibin levels can be used to provide a pharmacodynamic marker of FSP activity. Levels of follicular growth (an increase in the number of follicles greater than about 10 mm in diameter, (e.g., determined by ultrasound) and estradiol secretion (i.e., serum estradiol levels) can also be used to assess the effects of FSP; in males, Serotoli cell production levels can also provide an additional indicator of the efficacy of treatment. Preferably, pulmonary delivery of an FSP dry powder formulation as described herein is effective to result in a level of one or more of the above markers (follicular growth, serum estradiol, inhibin, Serotoli cell production) that is increased relative to its baseline level measured prior to FSP treatment.

The FSP powders of the invention are also useful, when administered to the deep lung, for Assisted Reproductive Technologies (ART). In such instances, FSP is administered to ovulatory infertile females undergoing stimulation of multiple follicular development for In Vitro Fertilization (IVF), Embryo Transfer (ET), and other assisted reproductive technologies. Generally, for use in female infertility-related conditions, FSP is administered to the deep lung for one or more treatment cycles of a period of from about 7 to 21 days or more to stimulate follicular growth. In the case of infertile females, in order to effect final maturation of the follicle and ovulation in the absence of a LH (luteinizing hormone) surge, human chorionic gonadotropin (hCG) is administered after sufficient follicle development has occurred (as described above). When used for treating male infertility, the FSP dry powder is typically administered for at least about six months, and typically for at least about a year.

Typically, treatment of the above-described conditions is effected by administering therapeutically effective doses of FSP dry powder that, on average, range from at least about 0.5 to 35 micrograms FSP/kilogram of patient daily, and preferably at least about 1 to 20 micrograms FSP/kilogram of patient daily, depending upon the specific activity of FSP contained in the composition. Suitable dosages are known to medical practitioners and will, of course, depend upon the particular disease state, specific activity of the composition being administered, and the particular patient undergoing treatment. For example, the amount of FSP administered per unit dosage form will generally range from about 5 IU to about 12,000 IU FSP, preferably from 5 IU to about 1000 IU FSP more preferably from about 37 IU to 500 IU, and even more preferably from about 50 IU to 300 IU FSP. Preferably, a therapeutically effective amount will range, on average, from about: 10 to 1000 IU FSP per day, 50 to 3,000 IU FSP per day, 75 IU to about 600 IU of FSP per day, or from about 200 IU to 12,000 IU FSP per day, depending upon the dosing regimen followed by the subject (i.e., the number of aerosolized doses delivered over a period of 24-hours or greater) and the type of treatment. In some instances, to achieve the desired therapeutic amount, it may be necessary to provide for daily repeated administration, i.e., repeated individual inhalations of a particular metered dose per day, where the individual administrations are repeated until the desired daily dose is achieved.

The following examples illustrate, but in no way are intended to limit the scope of the present invention.

All articles, books, patents and other publications referenced herein are hereby incorporated by reference in their entirety.

EXAMPLES

Materials and Methods

Materials uFSH. FSH derived from human urine (uFSH) was used as a source of FSP in certain experiments. Lyophilized uFSH powder (Vitro Diagnostics, Inc., Boulder, Colo.) was typically reconstituted to 5 mg/ml prior to preparation of formulation solutions. Initial formulations (powder lots no. R98025 through R98054) were prepared directly from the vendor-supplied uFSH material. Formulations R98067 through R98112 were prepared from uFSH that was further purified by ultrafiltration (Centricon 10, 10 kD molecular weight cutoff) to remove residual ammonium bicarbonate present in the vendor-supplied material. Glycoprotein integrity after desalting was confirmed by SE-HPLC and the percent glycoprotein recovery was determined by UV. The remaining solution was tested for solution stability at 4° C. overnight and for 3- freeze-thaw cycles.

Excipients. Excipients were obtained from commercial sources as follows: mannitol (Mallinckrodt Specialty Chemical Co., Paris, Ky.; U.S.P; FW 180), sodium citrate•$2H_2O$ (J.T. Baker Inc., Phillipsburg, N.J.; U.S.P; FW 294.1), citric acid•$H_2O$ (J.T. Baker, Phillipsburg, N.J.; U.S.P; FW 210.14), sucrose (EM Science, Gibbstown, N.J.; FW 342.2), raffinose•$5H_2O$ (Pfanstiehl Lab., Inc., Waukegan, Ill.; FW 594.5), glycine (J.T. Baker, Inc., Phillipsburg, N.J.; FW 75.07), trehalose•$2H_2O$ (Pfanstiehl Lab., Inc., Waukegan, Ill.; FW 350.3), leucine (Sigma, St. Louis, Mo.)

Sterile water for Irrigation (USP) was used for preparation of formulation solutions and reconstituted uFSH drug substance.

Methods

Spectroscopy. The concentrations of stock uFSH solutions, pre-spray dried solutions, and reconstituted powders were determined by ultraviolet/visible (UV/Vis) spectrophotometry. Sample solutions were diluted to give absorbance values between 0.1–1.5 unit at 276 nm. Solution turbidity at 400 nm was used as a measure of insoluble particle/aggregate formation.

Particle size measurement. Mass median diameters (MMD) of the powders were measured using a Horiba CAPA-700 particle size analyzer (Horiba Instruments inc., Irvine, Calif.). Measurements were based upon centrifugal sedimentation of dispersed particles in suspending medium. Mass median diameter, which is based on the particle's Stokes' diameter, was calculated using the particle density and the density and viscosity of the suspending medium. The density of the powder was set as 1.5 $g/cm^3$ for all powders. (This nominal value was used for all powders analyzed and is within a range that is typical for spray dried powders). Particle size measurements were conducted with about 5–10 mg powder suspended in 5 ml Sedisperse A-11 (Micromeritics, Norcross, Ga.) and dispersed by sonication for 10 minutes. The range over which particle size data was gathered was set to 0.4 to 10.0 μm.

Differential Scanning Calorimetry (DSC). The thermal behavior of spray dried powders (2–10 mg in hermetically sealed aluminum pans) was analyzed by a TA modulated differential scanning calorimeter 2920. Typically, samples were equilibrated at −60° C. for 10 min and heated at 2° C./min to 200° C. under a $N_2$ stream. The modulation amplitude was ±1° C. or ±0.3° C. and the modulation period was 60 sec where at least four cycles during a transition were achieved. The instrument was calibrated by Indium for temperature and heat capacity. A baseline scanning was performed before sample running.

Andersen Cascade Impactor. An Andersen cascade impactor (a sieve-like apparatus with a series of stages that capture particles on plates by inertial impaction according to their size) was used to determine the MMAD and particle size distribution of aerosolized powder formulations in an air stream. The plates were weighed before and after testing and the mass of powder deposited on the plate of each stage was determined. Unless otherwise indicated, studies were undertaken using a traditional Andersen cascade impactor having eight stages (from top to bottom stages 0 to 7) with cut-off sizes ranging from 9.0 to 0.4 μm, and a final filter stage that traps particles <0.4 μm when operated at a flow rate of 28.3 L/min. The device test set-up was similar to the DDE test, except that the cascade impactor and a USP (United States Pharmacopoeia, USP 23, chapter <601>) were attached to the device mouthpiece rather than to a filter. Multiple dispersions were typically conducted for each cascade impaction run to achieve gravimetrically accurate data, e.g., 20 FSP-filled blister packs (2 mg fill weight per blister pack).

Andersen Short Stack (SS) Method. In the SS method (used to determine APCs), the order in which the stages were placed was altered from the conventional Andersen cascade impactor set-up as described above. From the top, stage 0 was utilized for inlet cone attachment to connect the throat. Stage 3 was positioned next, beneath stage 0, followed by the filter stage (stage F). The powder-containing stream of air passes only through stages 0 and 3; air (but not powder) flows through the other stages, which are placed under stage F to hold the remainder of the assembly in place. A pre-weighed filter was placed on stage F and captured particles <3.3 μm. A second filter was placed on an inverted plate under stage 3, and captured particles >3.3 μm. For the studies described herein, one BP (blister pack) containing 2 mg of FSP powder composition was dispersed in an aerosol delivery device and a vacuum was pulled at 28.3 L/min as per USP methodology. This process was then repeated two times for a target mass of 6 mg per run. The filters were then removed and weighed to determine the amount of powder deposited.

Example 1

Pre-Formulation Evaluation of uFSH: Characterization of Drug Properties

Pre-formulation activities were undertaken to evaluate drug properties and to evaluate the stability of solution samples stored prior to analysis. Pre-formulation activities included evaluating glycoprotein stability to freeze-thaw cycling, adsorption to surfaces, solubility, and solution stability of (i) reconstituted bulk uFSH material, (ii) formulated uFSH in solution (pre-spray drying), and (iii) reconstituted solutions of uFSH powders. The pH range of pre-spray dried solutions (as described in Table 1) was maintained between 5 and 8. This pH range was investigated in order to monitor the effects of pH on glycoprotein stability and solid state properties. Near neutral pH was selected to help maintain physiological compatibility after dissolution of powder within the lung. Preliminary results indicated that all formulated uFSH solutions were stable when stored at 4° C. for 4 to 7 days, or when stored at ambient temperature for 1 day, or after repeated freeze-thawing cycles. Preliminary data indicated that the adsorptive loss of glycoprotein to silicon tubing was minimal. The first 2 mL of 175 μg/mL uFSH formulation solution resulted in 10 μg of uFSH adsorption to the tubing (2 m×4.6 mm i.d.) used with the Buchi spray dryer. No further loss of uFSH was observed in subsequent aliquots.

Example 2

Preparation of Representative uFSH Solution Formulations and Preparation of Powders for Pulmonary Delivery Formulation solutions were prepared at a total solids content of 0.5% (w/v). The pH of each solution was determined, and solutions were then inspected for clarity prior to spray drying. Table 1 lists the compositions of all pre-spray dried solutions. Mannitol was the sugar unless otherwise noted. Powders were produced by spray drying an aqueous solution of uFSH and excipient(s) using a Buchi 190 mini spray dryer (Buchi Labortechnik AG, Meierseggstrasse, Switzerland) equipped with a customized nozzle (as described in Platz, et al., 1997) and cyclone. Typical formulations were prepared from solutions containing less than 300 mg of total solids. High collection efficiencies, usually between 70 to 80%, were attained, resulting in a satisfactory powder supply for subsequent powder characterizations.

TABLE 1

Description of spray dried solutions and powder processing results.

| Form. ID | Lot # | uFSH:Sugar:Citrate (wt:wt:wt) | pH bsd[2] | pH asd[3] | Yield (g) | Yield (%) | MMD[4] (μm) |
|---|---|---|---|---|---|---|---|
| — | R98023 | 0:15:85 | 6.7 | 6.7 | 0.15 | 15 | nd |
| — | R98024 | 0:15:85 | 6.7 | 6.7 | 0.17 | 17 | nd |
| L2001 | R98025 | 3.5:15:81 | 7.7 | 7.7 | 0.17 | 81 | 0.98 |
| L2002 | R98026[5] | 3.5:81:15 | 7.8 | 7.4 | 0.03 | 13 | nd |
| L2003 | R98027 | 3.5:48:48 | 7.9 | 7.4 | 0.16 | 77 | 1.20 |
| L2004 | R98028 | 3.5:32:64 | 7.8 | 7.4 | 0.16 | 76 | 1.00 |
| L2005 | R98029 | 3.5:95:0 | 7.8 | 7.3 | 0.11 | 50 | 1.44 |
| L2006 | R98030 | 3.5:15:81 | 7.0 | 6.9 | 0.16 | 74 | 1.04 |
| L2006 | R98037 | 3.5:15:81 | 6.9 | 6.8 | 0.17 | 80 | 1.38 |
| L2007 | R98038 | 3.5:95:0 (sucrose) | 7.9 | 7.7 | 0.18 | 79 | 1.10 |
| L2008 | R98039 | 3.5:95:0 (raffinose) | 7.8 | 7.6 | 0.17 | 74 | 1.00 |
| L2006 | R98040 | 3.5:15:81 | 6.8 | 6.9 | 0.18 | 77 | 1.31 |
| L2010 | R98046 A | 5:15:80 | 7.0 | 7.0 | 0.27 | 77 | 1.21 |
| L2010 | R98046 B | 5:15:80 | 7.0 | 7.0 | 0.29 | 79 | 0.96 |
| L2011 | R98047 | 5:80:15 | 7.7 | 7.4 | 0.16 | 45 | 3.16 |
| L2012 | R98048 | 5:15:80 | 5.3 | 5.3 | 0.27 | 78 | 1.20 |
| L2013 | R98049 | 10:14:76 | 7.4 | na | 0.27 | 82 | 1.08 |
| L2014 | R98050 | 5:31:64 | 7.1 | 7.0 | 0.27 | 78 | 0.94 |
| L2015 | R98051 | 5:80:15 | 6.3 | 5.8 | 0.10 | 29 | 3.38 |
| L2006 | R98052[5] | 3.5:15:81 | 6.9 | 6.9 | 0.26 | 75 | 1.27 |
| L2006 | R98053 | 3.5:15:81 | 6.9 | 6.9 | 0.35 | 81 | 1.06 |
| L2016 | R98054 | 5:15:80 | 7.7 | 7.4 | 0.25 | 81 | 1.06 |
| L2020 | R98067 | 10:14:76 | 7.1 | 7.1 | 0.19 | 77 | 1.10 |
| L2012 | R98068 | 5:15:80 | 5.1 | 5.1 | 0.18 | 71 | 1.20 |
| L2016 | R98069 | 5:15:80 | 7.6 | 7.5 | 0.17 | 69 | 1.07 |
| L2006 | R98070 | 3.5:15:81 | 7.0 | 7.0 | 0.17 | 68 | 1.18 |
| L2010 | R98084 | 5:15:80 | 7.1 | 7.1 | 0.33 | 77 | 1.07 |
| L2017 | R98085 | 5:95:0 | 7.5 | 7.1 | 0.25 | 59 | 1.59 |
| L2018 | R98086 | 5:95:0 (raffinose) | 7.4 | 7.2 | 0.33 | 77 | 0.99 |
| L2019 | R98087[5] | 5:64:31 (raffinose) | 7.4 | 7.1 | 0.07 | 16 | 2.66 |
| L2010 | R98110 | 5:15:80 | 6.9 | 6.9 | 0.98 | 81 | 1.03 |
| L2017 | R98111 | 5:95:0 | 7.0 | 6.7 | 0.80 | 65 | 1.44 |
| L2018 | R98112 | 5:95:0 (raffinose) | 7.2 | 7.0 | 0.97 | 80 | 0.83 |

[1]target uFSH content, error was approximately ± 0.2%;
[2]solution pH before spray drying;
[3]pH of reconstituted powder;
[4]determined by centrifugal sedimentation (Horiba);
[5]lot excluded from testing.

The pH of the reconstituted powders (after spray drying, Table 1) from early lots demonstrated an unexpected drop in pH after spray drying, especially in unbuffered (i.e., no citrate) formulations. This was attributed to the presence of ammonium bicarbonate in the drug substance material. The pH drop was minimized upon use of purified drug substance and was insignificant in formulations containing buffer.

Example 3

Chemical Stability Evaluation of Spray Dried Powders: Loss of Monomeric uFSH Via Formation of Higher Order Aggregates The chromatographic purity and content of formulated uFSH solutions were assessed using a SE-HPLC (size exclusion high performance liquid chromatography) methodology, as described below.

TABLE 2

| SE-HPLC Parameters | |
|---|---|
| Column: | Tosohaas GW3000XL or GW2000XL, 5 um, 7.8 × 30 mm |
| Mobile Phase: | 0.1M sodium phosphate/5% IPA, pH 7.5 |
| Column Temperature: | Ambient |
| Flow Rate: | 0.5 mL/min |
| Typical Sample: | 3.5–10.0 μg |
| Detection: | 214 nm |

The intact monomer unit, its dissociated subunits and higher order aggregates eluted at retention times of 18.6 minutes, 20.2 minutes and 16.2 minutes (GW3000XL column), respectively, under the SE-HPLC conditions specified above. Retention times were decreased on the GW2000XL column.

The precision of the SE-HPLC method with the GW3000XL column was evaluated by six replicate injections of a single concentration of uFSH drug substance (173 μg/mL). The relative standard deviation was 0.0% and 0.2% for purity and response factor, respectively. The linearity of the SE-HPLC method was evaluated in the range of 0.87 to 17.4 mg of uFSH. A single concentration of uFSH solution (173 μg/mL) was injected at various volumes onto the column; each injected volume was applied in duplicate. The response indicated linearity with $R^2$=0.99999.

Chromatographically, the α and β subunits co-eluted and were not well resolved from the monomeric form of uFSH. Resolution profiles were maintained between 1 μg and 10 μg loading. Thus, quantitation of uFSH was determined by integration of the combined peak areas of the monomer and subunit peaks. The higher order aggregates were better resolved from monomer and were integrated separately. In summary, this method was utilized only to indicate the loss of monomeric uFSH through the formation of higher order aggregates.

TABLE 3

SE-HPLC Analysis of Bulk Powder and After Spray Drying

| | | Higher order uFSH Aggregates (by area) | | |
|---|---|---|---|---|
| ID | Lot | % bsd[1] | % asd[2] | change in % |
| L2001 | 98025 | 0.34 | 1.98 | 1.64 |
| L2002 | 98026 | 0.35 | 0.65 | 0.30 |
| L2003 | 98027 | 0.32 | 1.07 | 0.75 |
| L2004 | 98028 | 0.30 | 1.11 | 0.81 |
| L2005 | 98029 | 0.30 | 1.50 | 1.20 |
| L2006 | 98030 | 0.28 | 0.83 | 0.55 |
| L2006 | 98037 | 0.35 | 0.49 | 0.14 |
| L2007 | 98038 | 0.31 | 0.36 | 0.05 |
| L2008 | 98039 | 0.18 | 0.23 | 0.05 |
| L2009 | 98040 | 0.20 | 0.37 | 0.17 |
| L2010 | 98046a | 0.61 | 2.20 | 1.59 |
| L2010 | 98046b | 0.61 | 6.72 | 6.11 |
| L2011 | 98047 | 0.56 | 0.98 | 0.42 |
| L2012 | 98048 | 0.64 | 1.88 | 1.24 |
| L2013 | 98049 | 0.69 | 1.03 | 0.34 |
| L2014 | 98050 | 0.54 | 1.07 | 0.53 |
| L2015 | 98051 | 0.60 | 1.77 | 1.17 |
| L2006 | 98052 | 0.48 | 1.22 | 0.74 |
| L2006 | 98053 | 0.55 | 1.13 | 0.58 |
| L2016 | 98054 | 0.55 | 1.88 | 1.33 |
| L2020 | 98067 | 0.70 | 1.23 | 0.53 |
| L2012 | 98068 | 0.58 | 1.08 | 0.50 |
| L2016 | 98069 | 0.70 | 1.25 | 0.55 |
| L2006 | 98070 | 0.68 | 1.50 | 0.82 |
| L2010 | 98084 | 0.43 | 1.02 | 0.59 |
| L2017 | 98085 | 0.49 | 0.51 | 0.02 |
| L2018 | 98086 | 0.37 | 0.52 | 0.15 |
| L2019 | 98087 | 0.44 | 0.54 | 0.10 |
| L2010 | 98110 | 0.82 | 1.68 | 0.86 |
| L2017 | 98111 | 0.78 | 1.01 | 0.23 |
| L2018 | 98112 | 0.80 | 0.78 | −0.02 |

[1]bsd = before spray drying;
[2]asd = after spray drying

Table 3 above summarizes the change in percent higher order aggregate that occurred due to spray drying. Higher order aggregates were present as impurities in bulk drug substance (<0.8% purity by SE-HPLC) and increased slightly after spray drying. Less than 2% increase in higher order aggregate was observed for all uFSH formulations after spray drying, except lot R98046b which showed >6% higher order aggregate (and was considered an outlier). No clear trend in higher order aggregate formation with pH, or citrate, or uFSH content was observed.

Example 4

One Month and Long Term Stability of Packaged, Spray Dried Powders

The real time and accelerated stability of packaged powders were determined on the basis of % change in higher order aggregates between initial and 1-month time points (Table 4). Powders were hand-filled to a total mass of 2 mg in blister packs (BPs). The blister packs were placed in Petri dishes (20–60 BPs/dish). The Petri dishes were then secondarily packaged in foil pouches with desiccant.

TABLE 4 uFSH Packaged Powder Stability Analyzed by SE-HPLC

| | | Higher order aggregate | | | |
|---|---|---|---|---|---|
| Form/Lot (Size) | Time point | % Total | (+/−) | % Change | (+/−) |
| L2010/R98084 | Pre-spray | 0.68 | 0.02 | na | na |
| (0.5 g) | Initial | 1.03 | 0.01 | na | na |
| | 1 month (40° C.) | 1.76 | 0.01 | 0.74 | 0.01 |

TABLE 4-continued uFSH Packaged Powder Stability Analyzed by SE-HPLC

| Form/Lot (Size) | Time point | Higher order aggregate % Total | (+/−) | % Change | (+/−) |
|---|---|---|---|---|---|
| L2017/R98085 | Pre-spray | 0.60 | 0.02 | na | na |
| (0.5 g) | Initial | 0.55 | na | na | na |
| | 1 month (40° C.) | 1.25 | 0.05 | 0.70 | 0.04 |
| L2018/R98086 | Pre-spray | 0.58 | 0.00 | na | na |
| (0.5 g) | Initial | 0.65 | 0.02 | na | na |
| | 1 month (40° C.) | 0.69 | 0.03 | 0.05 | 0.03 |
| L2010/R98110 | Pre-spray | 0.82 | 0.01 | na | na |
| (1.25 g) | Initial | 1.70 | 0.01 | na | na |
| | 1 month (30° C.) | 1.83 | 0.02 | 0.16 | 0.02 |
| | 1 month (40° C.) | 2.27 | 0.01 | 0.59 | 0.02 |
| L2017/R98111 | Pre-spray | 0.78 | 0.01 | na | na |
| (1.25 g) | Initial | 1.02 | 0.05 | na | na |
| | 1 month (30° C.) | 1.18 | 0.07 | 0.17 | 0.07 |
| | 1 month (40° C.) | 1.76 | 0.12 | 0.74 | 0.10 |
| L2018/R98112 | Pre-spray | 0.80 | 0.01 | na | na |
| (1.25 g) | Initial | 0.78 | 0.02 | na | na |
| | 1 month (30° C.) | 0.71 | 0.08 | −0.08 | 0.10 |
| | 1 month (40° C.) | 0.85 | 0.01 | 0.06 | 0.02 |

Several of the representative packaged formulations demonstrated good storage stability. Urinary FSH formulated with raffinose exhibited good stability under both sets of conditions. Mannitol/citrate and mannitol-based formulations were stable at 30° C. for 1-month as supported by the insignificant increase in higher order aggregate (<0.2%). The higher order aggregate further increased as temperature increased to 40° C. for both formulations with a total of percentage change <0.8% after 1-month storage, indicating that both the mannitol/citrate and the mannitol formulations have comparable stability.

Long term stability (48–52 weeks) was similarly measured by SE-HPLC for certain mannitol-citrate blister packaged uFSH powders (5% uFSH/15% mannitol/80% citrate: L2012/powder lot 98048; L2010/powder lot 98110) stored at ambient temperatures and ≦5% relative humidity. Powder L2012, which demonstrated an initial higher order aggregate level after spray drying of 1.8%, remained virtually unchanged after 52 weeks, with total higher order aggregates at 1.5%. Similarly, the higher order aggregate level for powder L2010, initially at 1.7% after spray-drying, increased to only 2.6 percent when measured after storage for 48 weeks in a sealed blister package.

Example 5

Extent of uFSH Sialylation After Spray Drying

Due to the presence of potentially labile terminal sialic acid residues in uFSH, a colorometric method was utilized to investigate the integrity of uFSH sialylation after spray drying. In carrying out the method, terminal sialic acid groups were cleaved at low pH, followed by a copper catalyzed reaction with resorcinol. The absorbance of the product was measured at 560 nm and subsequently converted to nmol sialic acid based on a calibration curve generated with N-acetylneuraminic acid (NANA). Triplicate measurements were carried out for both standards and glycoprotein samples. Prior to the color forming reaction, the intact sialylated glycoproteins were separated from any free sialic acid by passing the sample through a NICK column. An aliquot of each eluted fraction was used for the reaction.

The linear range for this method extended to 80 nmol. The lower limit of detection was found to be 2 nmol of sialic acid, which corresponds to the ability to detect a 1–2% loss for a 3.5% uFSH powder. The accuracy of the method was tested with fetuin as a control. The resulting sialic acid concentration was 380 nmol/mg protein, which compared well with the average value of 370±35 nmol/mg reported in a comprehensive inter-laboratory ABRF study on Fetuin (ACS National Meeting, April 1997).

The colorometric method was used to evaluate two uFSH powders (R98026, R98029). A 2 mM citrate solution was used to reconstitute the powders and to elute the sialylated glycoproteins from the NICK column. The resulting elution profiles for the two lots indicated the absence of free sialic acid in both of the formulations. A Bradford assay was conducted to confirm the presence of protein in fractions 1–3.

Since cleavage of sialic acid is more likely under acidic conditions, the same assay was employed to ascertain whether sialic acid cleavage would occur in formulations prepared at lower pH. For this assay, powders R98046 and R98048 were utilized. The profiles obtained were similar to those observed at higher pH.

The concentrations of the intact sialic acid for all four lots (Table 5) were similar to the sialic acid concentration for the initial stock solution of urinary FSH, indicating that the extent of uFSH sialylation was unaffected by spray drying. Thus, the results in Table 5 illustrate the chemical stability of uFSH towards desialylation under conventional spray drying conditions.

TABLE 5

Quantitative Results from Sialic Acid Assay

| Lot | Composition (%) uFSH | Mannitol | Citrate | Sialic Acid (nmol/mg protein) | pH |
|---|---|---|---|---|---|
| R98026 | 3.5 | 81 | 15 | 266 ± 24 | 7.7 |
| R98029 | 3.5 | 96 | 0 | 282 ± 33 | 7.8 |
| R98046 | 5 | 15 | 80 | 285 ± 26 | 7.0 |
| R98048 | 5 | 15 | 80 | 288 ± 12 | 5.3 |
| stock | 0.5 | — | — | 297 ± 15 | — |

The results in Table 5 demonstrate that at near neutral or slightly acidic pH values there is no loss of sialylation of uFSH in representative formulations as a result of spray drying. The average sialic acid content measured by this assay (8.8% by weight) is comparable to that for uFSH (8.96% by weight).

Example 6

Solid State Characterization of uFSH Powders for Pulmonary Delivery

Representative uFSH powder formulations were further characterized to explore the effects of various excipients and residual moisture on the solid state properties of the resulting powders, and their combined effect on protein stability.

Modulated differential scanning calorimetry (DSC). DSC was used to determine the heat flux profile of a given spray dried powder sample, to measure its glass transition temperatures (Tg), and to estimate the degree of crystallinity. Glass transition temperatures were also determined to provide an indication of the potential solid state stability of particular formulations, since high Tg values may indicate a greater potential for physical stability than low Tgs. DSC measurements were conducted as described under the Materials and Methods section above. Table 6 summarizes the DSC data and the glass transition temperatures obtained for representative uFSH powder formulations.

Looking at the data presented in Table 6, the amorphous raffinose formulations showed a distinct glass transition near 100° C. In addition, high Tgs (70 to 90° C.) were observed for the high-citrate content formulations (>80% citrate); the Tg was followed by an exotherm attributed to crystallization of an anhydrous polymorph of citrate. The mannitol/citrate formulations with less citrate (<60% citrate) exhibited lower Tgs (30 to 60° C.), an exotherm at ~90° C. due to crystallization of mannitol, and the subsequent melting of mannitol. Highly crystalline 95% mannitol formulations exhibited no observable Tg; only an endotherm at ~60° C. characteristic of the melting of crystalline mannitol. Looking more generally at the data, the effect of residual ammonium bicarbonate from impure uFSH appeared to depress Tg values. Although citric acid (low pH) is reported to depress the Tg of citrate glasses [Lu, Q., et al., *Pharm. Res.,* 15(8):1202–1206 (1998)], this was not readily apparent in the pH range investigated. These data demonstrate the ability to prepare stable uFSH powders of varied Tgs and degrees of crystallinity.

Thermogravimetric Analysis. Thermogravimetric analysis (TGA), a technique for monitoring the weight loss from a sample upon heating from room temperature to 200° C., was employed to determine the residual water content of the above-described uFSH dry powders. Weight loss observed upon heating from 25 to ~150° C. was ascribed to the loss of residual moisture. The moisture content of spray dried powder (2–10 mg in hermetically sealed aluminum pans packed in glove box) was analyzed with a TA 2950 thermogravimetric analyzer. The tops of the sealed pans were pierced immediately prior to loading into the TGA furnace to minimize water uptake from room air. Results are provided in Table 6. In looking at the results in Table 6, formulations prepared with impure uFSH exhibited a fairly high weight loss upon heating, which was later attributed to the presence of residual ammonium bicarbonate in the powder (ammonium bicarbonate begins to decompose at 60° C.). Moisture content was less than 2% for sodium citrate-free powders prepared with purified uFSH, while high-citrate content powders generally contained between 2 and 6% water.

TABLE 6

Solid state characteristics of uFSH Powders

| Form ID | Form Lot | Composition (wt/wt/wt) uFSH/mannitol/citrate | pH bsd[1] | pH asd[2] | TGA rate min | TGA H2O % | Karl Fisher H2O % | DSC Tg C |
|---|---|---|---|---|---|---|---|---|
| | 98023 | 0:15:85 | na | na | | | | |
| | 98024 | 0:85:15 | na | na | | | | |
| L2001 | 98025 | 3.5:15:81 | 7.7 | 7.7 | 6.7 | 6 | 69 | |
| L2002 | 98026 | 3.5:81:15 | 7.8 | 7.4 | 1.0 | na | 28 | |
| L2003 | 98027 | 3.5:48.5:48.5 | 7.9 | 7.4 | 3.8 | 4.1 | 51 | |
| L2004 | 98028 | 3.5:32:64 | 7.8 | 7.4 | 5.0 | na | 60 | |
| L2005 | 98029 | 3.5:96 | 7.8 | 7.3 | 6.5 | na | none | |
| L2006 | 98030 | 3.5:15:81 | 7.0 | 6.9 | 5.1 | na | 79 | |
| L2006 | 98037 | 3.5:15:81 | 6.9 | 6.8 | 4.5 | na | | |
| L2007 | 98038 | 3.5:96:0 sucrose | 7.9 | 7.7 | nd | na | | |
| L2008 | 98039 | 3.5:96:0 raffinose | 7.8 | 7.6 | 1.8 | na | 100 | |
| L2009 | 98040 | 3.5:15:81 | 6.8 | 6.9 | 4.5 | na | 83 | |
| L2010 | 98046a | 5:15:80 | 7.0 | 7.0 | 4.6 | na | | |
| L2010 | 98046b | 5:15:80 | 7.0 | 7.0 | 3.9 | na | 84 | |
| L2011 | 98047 | 5:80:15 | 7.7 | 7.4 | | na | 33 | |
| L2012 | 98048 | 5:15:80 | 5.3 | 5.3 | | 0.5 | na | 73 |
| L2013 | 98049 | 10:14:76 | 7.4 | 7.3 | | 5.1 | na | 88 |
| L2014 | 98050 | 5:31:64 | 7.1 | 7.0 | | 2.6 | na | 75 |
| L2015 | 98051 | 5:80:15 | 6.3 | 5.8 | | 1.4 | na | |
| L2006 | 98052 | 3.5:15:81 | 6.9 | 6.9 | | 4.1 | na | |
| L2006 | 98053 | 3.5:15:81 | 6.9 | 6.9 | | 4.0 | na | 82 |
| L2016 | 98054 | 5.0:15:80 | 7.7 | 7.4 | | 7.4 | na | 83 |
| L2020 | 98067 | 10:14:76 | 7.1 | 7.1 | | 3.5 | na | 82 |
| L2012 | 98068 | 5:15:80 | 5.1 | 5.1 | | 2.4 | na | 65 |
| L2016 | 98069 | 5:15:80 | 7.6 | 7.5 | | 3.6 | na | 84 |
| L2006 | 98070 | 3.5:15:81 | 7.0 | 7.0 | | 5.6 | na | 73 |
| L2010 | 98084 | 5:15:80 | 7.1 | 7.1 | 10 | 3.3 | na | 90 |
| L2017 | 98085 | 5:95:0 | 7.5 | 7.1 | 10 | 0.6 | na | nd |
| L2018 | 98086 | 5:95:0 raffinose | 7.4 | 7.2 | 10 | 1.4 | na | 99 |
| L2019 | 98087 cyclone | 5:64:31 raffinose | na | na | 10 | 1.2 | na | na |
| L2019 | 98087 collector | 5:64:31 raffinose | 7.4 | 7.1 | 10 | 0.3 | na | 43 |
| L2010 | 98110 | 5:15:80 | 6.9 | 6.9 | 10 | 2.8 | na | 83 |
| L2017 | 98111 | 5:95:0 | 7.0 | 6.7 | 10 | 0.5 | na | nd |

TABLE 6-continued

Solid state characteristics of uFSH Powders

| Form ID | Form Lot | Composition (wt/wt/wt) uFSH/mannitol/citrate | pH bsd[1] | pH asd[2] | TGA rate min | TGA H2O % | Karl Fisher H2O % | DSC Tg C |
|---|---|---|---|---|---|---|---|---|
| L2018 | 98112 | 5:95:0 raffinose | 7.2 | 7.0 | 10 | 0.7 | na | 98 |

[1]pH of formulation solution before spray drying,
[2]pH of reconstituted powder X-ray Diffraction. Powder X-ray diffraction studies were performed on a Shimadzu XRD6000 diffractormeter to characterize the extent of crystallinity of representative powder samples (L2010, L2017, L2018). The uFSH/mannitol/citrate formulation (L2010) was determined to be largely amorphous as indicated by the absence of distinct diffraction peaks. The uFSH/mannitol formulation (L2017) appears highly crystalline in light of a diffraction pattern characteristic of the α-polymorph of mannitol. The uFSH/raffinose formulation (L2018) was completely amorphous, as determined by the absence of distinct diffraction peaks. These data are consistent with the DSC results described above.

Moisture Sorption. Moisture sorption analyses were conducted to provide an indication of the hygroscopicity of certain uFSH powder samples. Specifically, the samples were held at constant temperature and exposed to an excursion of relative humidity, from 0% to 80%, then back to 0% RH. Each sample was positioned on a microbalance to monitor the equilibrium weight gain as a function of RH. The moisture sorption results of two illustrative uFSH powders were as follows. A high-citrate content powder (L2006, uFSH/mannitol/citrate) showed a sharp change in the moisture uptake profile between 30 and 40% RH, which was attributed to the formation of citrate dihydrate. A 95% mannitol formulation showed a small transition around 60% RH which was attributed to the crystallization of a small amount of remaining amorphous mannitol. (Small amounts of amorphous mannitol (<5%) associated with the protein are difficult to detect using DSC or X-ray diffraction). Isothermal microcalorimetry (TAM) data also depicted the presence of mannitol crystallization at 60% RH. Crystallization of mannitol was also detected in a mannitol/citrate formulation by isothermal microcalorimetry. The results of these moisture sorption studies reveal a preferred mode of handling the resultant powders, i.e., keeping the powders dry during manufacture, packaging, and on storage.

Example 7

Aerosol Performance of uFSH Dry Powders

The aerosol performance of representative uFSH powders was evaluated, using various measurable parameters, to determine their suitability for delivery to the lung.

Delivered Dose Efficiency Measurements (DDE). A single blister pack (BP) filled with 2 mg of uFSH powder was loaded into a dry powder inhaler as described in Smith, A. E., et al., U.S. Pat. No. 5,740,794, Apr. 21, 1998. The device was then fired, dispersing the powder into the device chamber. Particles forming the resultant aerosol cloud were then drawn from the device chamber by vacuum at a rate of 30 L/min for 2.5 seconds and were captured on a pre-weighed filter attached to the device mouthpiece. The particle-containing filter was weighed again to provide the mass of powder from the blister pack that reached the filter. The fired BP was also weighed after dispersion to determine the amount of powder that remained in the blister package following the event. For the data reported below, one test set was composed of 5 to 10 BP dispersions.

Aerodynamic Particle Size Measurement. A modified short stack (SS) method with the Andersen cascade impactor was utilized during the early screening phase of uFSH powder formulations. The SS method was utilized to provide the FPF, the APC and CI Eff values. The full-sized Andersen cascade impactor was utilized for analysis of the accelerated stability batches. Aerosol performance results carried out as described above are provided for representative uFSH-containing powder compositions in the Tables below.

TABLE 7

Percent emitted dose (mean, SD, and range), percent powder left in the BP, and percent powder collected that left the BP for each powder lot

| Form No. | Lot No. | n | Emitted Dose (%) (DDE) Mean | SD | min | max | % Left mean | SD | % Collected mean | SD |
|---|---|---|---|---|---|---|---|---|---|---|
| L2001 | 98025 | 5 | 68 | 10 | 57 | 82 | 8 | 4 | 73 | 9 |
| L2003 | 98027 | 5 | 9 | 5 | 2.5 | 16 | 44 | 17 | 15 | 6 |
| L2004 | 98028 | 5 | 25 | 17 | 7 | 45 | 18 | 24 | 29 | 15 |
| L2005 | 98029 | 5 | 66 | 5 | 58 | 71 | 11 | 4 | 74 | 4 |
| L2006 | 98030 | 5 | 71 | 10 | 60 | 83 | 19 | 5 | 88 | 11 |
| L2006 | 98037 | 5 | 58 | 3 | 55 | 64 | 16 | 3 | 69 | 4 |
| L2007 | 98038 | 5 | 15 | 8 | 7 | 24 | 23 | 14 | 19 | 9 |
| L2008 | 98039 | 5 | 50 | 4 | 45 | 54 | 26 | 6 | 68 | 7 |
| L2006 | 98040 | 5 | 64 | 6 | 58 | 74 | 19 | 7 | 79 | 5 |
| L2010 | 98046A | 5 | 54 | 2 | 53 | 57 | 12 | 3 | 62 | 2 |
| L2010 | 98046B | 6 | 50 | 3 | 46 | 56 | 22 | 5 | 65 | 5 |
| L2011 | 98047 | 5 | 29 | 4 | 24 | 33 | 4 | 4 | 30 | 5 |
| L2012 | 98048 | 5 | 69 | 7 | 63 | 79 | 8 | 3 | 75 | 7 |
| L2013 | 98049 | 5 | 41 | 5 | 36 | 48 | 19 | 3 | 51 | 4 |
| L2014 | 98050 | 5 | 52 | 5 | 44 | 58 | 9 | 2 | 57 | 6 |
| L2015 | 98051 | 5 | 46 | 6 | 41 | 55 | 9 | 5 | 51 | 5 |
| L2006 | 98053 | 4 | 53 | 6 | 48 | 61 | 18 | 3 | 64 | 5 |
| L2016 | 98054 | 5 | 42 | 3 | 39 | 45 | 26 | 7 | 57 | 3 |
| L2020 | 98067 | 5 | 71 | 2 | 68 | 74 | 12 | 2 | 81 | 2 |
| L2012 | 98068 | 5 | 68 | 2 | 65 | 70 | 9 | 3 | 75 | 1 |
| L2016 | 98069 | 5 | 69 | 2 | 67 | 72 | 17 | 4 | 84 | 3 |
| L2006 | 98070 | 5 | 63 | 10 | 46 | 70 | 12 | 6 | 71 | 8 |
| L2010 | 98084 | 6 | 62 | 3 | 55 | 66 | 28 | 3 | 84 | 5 |
| L2017 | 98085 | 6 | 64 | 11 | 47 | 75 | 18 | 5 | 77 | 10 |
| L2018 | 98086 | 6 | 60 | 5 | 55 | 69 | 27 | 7 | 83 | 6 |

In looking at the above data, formulations exhibiting superior aerosol performance were L2006, L2010, and L2020, each composed of mannitol:citrate (1:5, pH 7) containing 3.5, 5, and 10% uFSH, respectively. The first four screen sets all included L2006 (3.5% uFSH), and its DDE averaged 62±7% for the five lots prepared; the averages for individual lots varied from 53 to 71%. The DDE of the L2010 (5% uFSH) lots averaged 55±5% (n=5), and the DDE of individual lots ranged from 47 to 66%. The 10% uFSH-content powder had an average DDE of 71%, but upon re-testing showed an unexplained drop to 55%. Other powder formulations exhibiting particularly good powder dispersabilities, i.e., having DDE values of 60% or greater included L2001, L2005, L2006, L2012, L2016, L2006, L2010, L2017, and L2018. The DDE of the raffinose powders L2018 and L2008 averaged 50±10% (n=3 lots). Although the DDE of the raffinose formulations was lower than some of the other uFSH formulations, these powders were distinguished by the fine nature of their aerosol clouds. As an additional indicator of aerosol performance, Andersen short stack test results are provided in Table 8 below showing mean Fine Particle Fraction (FPF or %<3.3 μm), mean Aerosol Performance Coefficient (APC), mean cascade impactor (CI) efficiency and estimated MMAD for three measurements (three blister packs per measurement).

TABLE 8

Short Stack Andersen Particle Size Measurements

| Form No. | Lot No. | n[(1)] | Andersen Short Stack CI: FPF (% < 3.3 μm) mean | APC mean | CI % Efficiency mean | MMAD (μm) |
|---|---|---|---|---|---|---|
| L2001 | 98025 | 3 | 81 | 0.44 | 54 | 2.2 |
| L2005 | 98029 | 3 | 58 | 0.33 | 57 | 3.0 |
| L2006 | 98030 | 3 | 83 | 0.43 | 52 | 2.1 |
| L2006 | 98037 | 3 | 81 | 0.42 | 52 | 2.2 |
| L2008 | 98039 | 3 | 91 | 0.49 | 53 | 1.8 |
| L2006 | 98040 | 3 | 79 | 0.42 | 53 | 2.2 |
| L2012 | 98048 | 3 | 59 | 0.34 | 57 | 2.9 |
| L2020 | 98067 | 3 | 61 | 0.37 | 60 | 2.9 |
| L2012 | 98068 | 3 | 51 | 0.33 | 64 | 3.2 |
| L2016 | 98069 | 3 | 64 | 0.39 | 61 | 2.8 |
| L2006 | 98070 | 4 | 74 | 0.37 | 51 | 2.4 |
| L2010 | 98084 | 2 | 80 | 0.38 | 47 | 2.2 |
| L2017 | 98085 | 2 | 50 | 0.30 | 59 | 3.3 |
| L2018 | 98086 | 2 | 89 | 0.44 | 50 | 1.9 |

[(1)]3 blister packs were used per measurement (n)

The Andersen short stack data indicated good powder performance characteristics for the powders tested. All formulations exhibited FPF values equal to or greater than 50%, indicating that 50% or greater of the particles have sizes below 3.3 microns. Such powders are desirable for delivery to the deep lung for subsequent systemic uptake. Half of the formulations tested exhibited FPF values of 75% or more, indicating the high percentage of small sized particles present in the formulations. These formulations included L2001, L2006, L2008, L2010, and L2018. Nearly all powders also exhibited particularly good APC values, preferably 0.36 or greater. These formulations included L2001, L2006, L2008, L2020, L2016, L2010, and L2018. The APC of L2006 consistently exceeded 0.36 and ranged from 0.37 to 0.42, with corresponding values for FPF (%<3.3 μm) between 74 to 83%. The APC values for L2010 were very similar and ranged from 0.34 to 0.38, with 70 to 80% FPF.

The raffinose formulations gave very high values for APC, from 0.37 to 0.49, with corresponding FPF values of 90%. Mannitol formulations demonstrated slightly lower APCs (0.26 to 0.33). Thus, mannitol formulations appeared to produce the largest aerosol particle sizes, while the mannitol/citrate formulations were mid-sized, and the raffinose formulations were of the smallest aerosol particle size.

Accelerated Stability Study. Three powder formulations, L2010, L2017, L2018 were set up for one month at 30° C. and 40° C. and a stress cycling condition of 2–40° C. Previously generated short stack data was confirmed when the stability batches were tested for particle size distribution with the full stack set-up. Table 9 contains the data from the accelerated stability study.

TABLE 9

Accelerated Stability Summary of Data

| Form/ Lot | Con- dition | n | Emitted Dose (%) mean | SD | min | max | % Left mean | SD | % Collected mean | SD |
|---|---|---|---|---|---|---|---|---|---|---|
| L2010 | 2–40 | 10 | 52.2 | 4.8 | 41 | 57 | 29 | 2 | 74 | 6 |
| 98110 | 30 | 10 | 55.7 | 3.7 | 49 | 60 | 27 | 3 | 76 | 3 |
| | 40 | 11 | 51.4 | 5.0 | 43 | 84 | 28 | 10 | 75 | 6 |
| | t = 0 | 10 | 50.5 | 5.1 | 40 | 59 | 28 | 8 | 71 | 7 |
| L2017 | 2–40 | 11 | 48.2 | 3.9 | 39 | 52 | 20 | 5 | 60 | 3 |
| 98111 | 30 | 11 | 50.9 | 3.2 | 46 | 57 | 14 | 3 | 59 | 4 |
| | 40 | 10 | 49.9 | 3.3 | 44 | 54 | 14 | 4 | 58 | 4 |
| | t = 0 | 11 | 47.2 | 2.8 | 41 | 52 | 15 | 4 | 56 | 3 |
| L2018 | 2-40 | 10 | 45.1 | 4.0 | 37 | 54 | 23 | 9 | 60 | 5 |
| 98112 | 30 | 11 | 47.0 | 6.0 | 35 | 54 | 24 | 6 | 62 | 4 |
| | 40 | 9 | 49.8 | 5.3 | 41 | 59 | 23 | 5 | 64 | 3 |
| | t = 0 | 10 | 41.1 | 4.8 | 34 | 50 | 30 | 5 | 59 | 3 |

| Form/Lot | Condition | n | Andersen Short Stack CI: FPF (% < 3.3 μm) mean | APC mean | CI % Efficiency mean |
|---|---|---|---|---|---|
| L2010 | 2–40 | 3 | 68 | 0.32 | 47 |
| 98110 | 30 | 3 | 72 | 0.32 | 45 |
| | 40 | 3 | 75 | 0.35 | 47 |
| | t = 0 | 3 | 70 | 0.34 | 49 |
| L2017 | 2–40 | 3 | 53 | 0.25 | 47 |
| 98111 | 30 | 3 | 53 | 0.24 | 46 |
| | 40 | 3 | 50 | 0.25 | 50 |
| | t = 0 | 3 | 53 | 0.26 | 50 |
| L2018 | 2-40 | 3 | 87 | 0.35 | 41 |
| 98112 | 30 | 3 | 86 | 0.34 | 40 |
| | 40 | 3 | 87 | 0.35 | 40 |
| | t = 0 | 3 | 89 | 0.37 | 41 |

In the accelerated stability study, initial DDE values were lower than for previous batches. On testing at one month, however, there was no decline in DDE for any of the powder formulations held at any of the stability conditions. FIG. 1 shows the relationship between FPF and MMAD for three uFSH powder formulations employed in this one-month stability study (L2010, L2017, L2018). Looking at the clusters of data points presented in FIG. 1 and proceeding from left to right along the x-axis, the data clusters correspond to samples L2017, L2010, and L2018, respectively. The APC values for both the initial and one month measurements were quite consistent within each powder formulation and were consistent with the APC values of earlier batches. Thus, the exemplary powder formulations described herein exhibit good aerosol performance and stability.

Example 8

Bioactivity of uFSH Dry Powders

The bioactivity of four representative dry powder uFSH formulations, L2013 (10% uFSH, 14% raffinose, 76% citrate), L2010 (5% uFSH, 15% raffinose, 80% citrate), L2006 (3.5% uFSH, 15% mannitol, 81% citrate), and L2008 (3.5% uFSH, 95% raffinose) was determined by a β-lactamase sensitive reporter cell assay. The four uFSH powder formulations retained significant bioactivity comparable to a uFSH standard. Other suitable in vitro assays are mentioned herein.

Figure 2A:
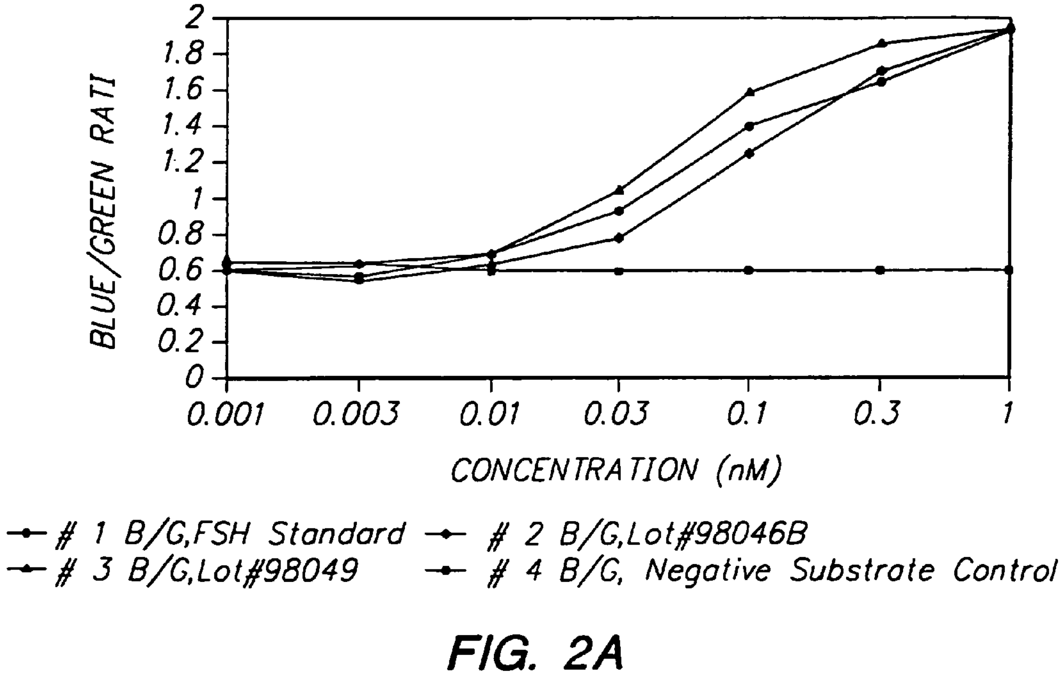
FIGS. 2A and 2B are graphs demonstrating the results of an in vitro bioassay to determine the bioactivity of representative uFSH dry powder formulations compared to an FSH standard (Example 8).
Figure 2B:
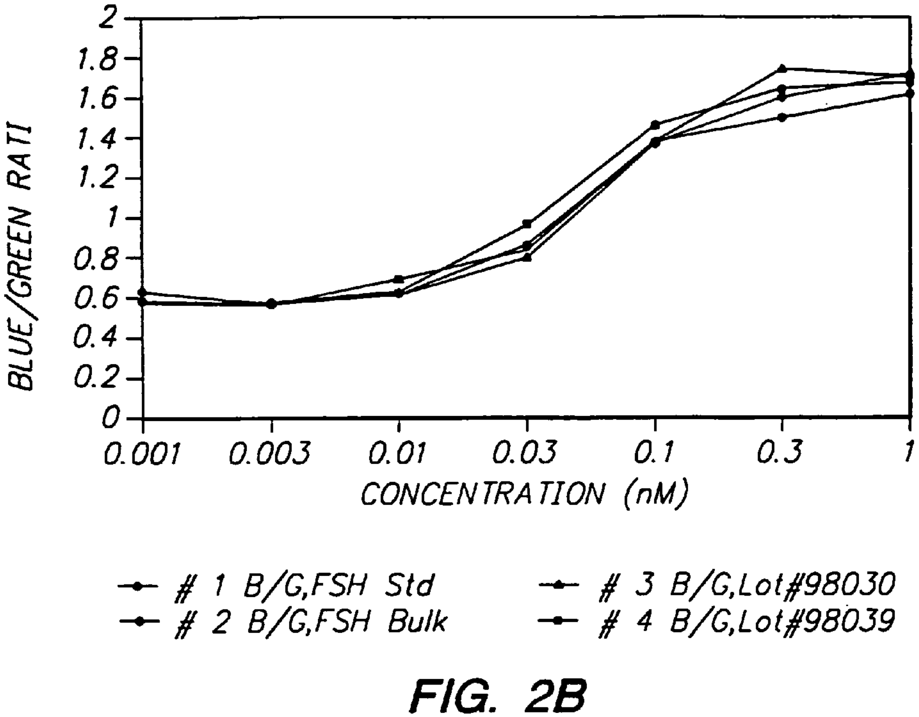

These results are depicted graphically in FIGS. 2A and 2B.

Example 9

Bioavailability of Subcutaneous (SC) and Intratracheally (IT) Administered FSP in Rats The following studies were undertaken to provide an indication of the bioavailability of intratracheally administered FSP in rats relative to SC-administered FSP.

Protocol 1 (FSP-SC). Human FSH from pituitary was obtained from Sigma (St. Louis, Mo., USA, lot #34H0069 product # F 4021). The diluent was PBS (phosphate-buffered saline) containing 1% albumin. Male Sprague-Dawley rats weighing between 280–300 grams were used for the single exposure study. Two animals were used per data collection time point for a total of 6 time points. Animals were administered either 0.9 units/200 µL or 9.0 units/200 µL, killed at the appropriate times and a total blood sample was obtained. Individual rats were used for each time point. Blood samples were collected at 0, 4, 8, 24, 48, and 96 hours. Samples were centrifuged and the supernatants were frozen at −80° C. until analyses using RIA kits from ICN Pharmaceuticals (Costa Mesa, Calif. USA).

Protocol 2 (uFSH-SC and IT). Active agent administered to the animals was "FERTINORM HP" 75IU (Urofollitropin IFSH) im/sc, obtained from Serono Laboratories (Norwell, Mass., USA). Active agent (ten vials of uFSH each containing 10 mg of lactose) was reconstituted by addition of 1 ml of NaCl solution supplied by the vendor, to which was added sufficient PBS (phosphate-buffered saline) to prepare solutions having a concentration of 9.0 units/200 µL FSH. Male Sprague-Dawley rats weighing 280–300 grams were used for the single exposure study. Each group was composed of thirty six animals, with a control group of 4 animals for each day. Drug solutions containing 9.0 units/200 µL uFSH were administered to the animals at given time points for both the IT and SC studies. Two animals were used per data collection time point for a total of 6 time points.

Example 10

Pharmacokinetics of uFSH following Pulmonary and Subcutaneous Administration in Cynomolgus Monkeys The following in vivo pharmacokinetic (PK) study was conducted to examine the bioavailability of follicle stimulating protein (uFSH) in cynomolgus monkeys when administered by the pulmonary route as an alternative to subcutaneous or intramuscular injection.

Each of five female cynomolgus monkeys was administered uFSH by a subcutaneous injection followed by three separate pulmonary doses of aerosolized uFSH powder composition 2010 (2 mg dose; 5% FSH/15% mannitol/80% citrate)). For pulmonary administration of the powder, the monkeys were placed within a helmet-type exposure apparatus and the FSH dry powder was dispersed directly into the helmet using a dry powder inhaler device of the type described in Smith, A. E., et al., U.S. Pat. No. 5,740,794, Apr. 21, 1998. Inhaled doses of increasing concentrations of FSH were administered over 5 or 15 minute exposure periods. The actual averages of inhaled doses were 3.8±1.7 µg/kg, 18.4±1.3 µg/kg and 37.2±3.9 µg/kg, which were calculated post-treatment based on the aerosol concentration, the mean minute volume, and the exposure duration for each monkey during each inhalation. Dose administrations were separated by at least one week.

Whole blood samples were collected at 0 hours (predose), 0.08, 0.25, 0.5, 1, 3, 6, 9, 12, 24, 48 and 72 hours post-dose. Serum concentrations of immunoreactive uFSH were determined by a validated, modified immunoradiometric assay ((IRMA), 906DM-052-01), employing a commercial FSH kit, (Coat-A-Count® FSH IRMA, DPC® Ltd., Los Angeles, Calif.). Percent relative bioavailability was calculated by Microsoft Excel using the following relationship [Wagner, J., *Pharmacokinetics for the Pharmaceutical Scientist*, 188–189 (1993)]:

$$\left| \frac{(AUC_{pulmonary} \times DOSE_{sc})}{(AUC_{sc} \times DOSE_{pulmonary})} \right| \times 100$$

Figure 4:
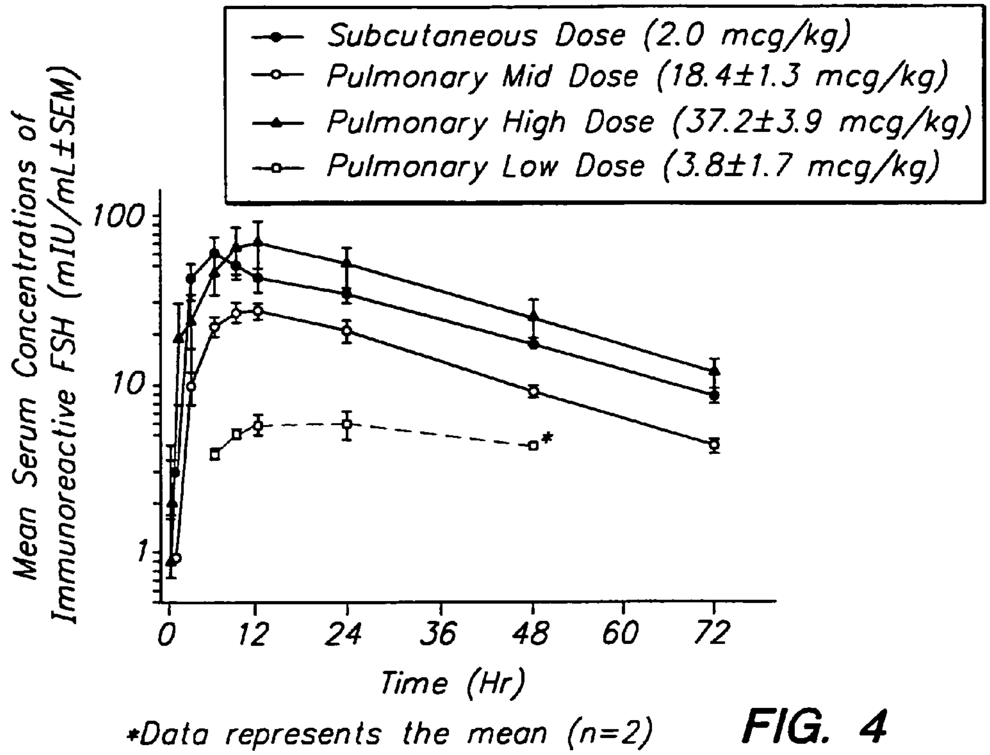
FIG. 4 provides a graphical representation of mean serum concentrations (±SEM) of immunoreactive FSH in cynomolgus monkeys following pulmonary and subcutaneous administration of human uFSH (Example 10).
Figure 5:
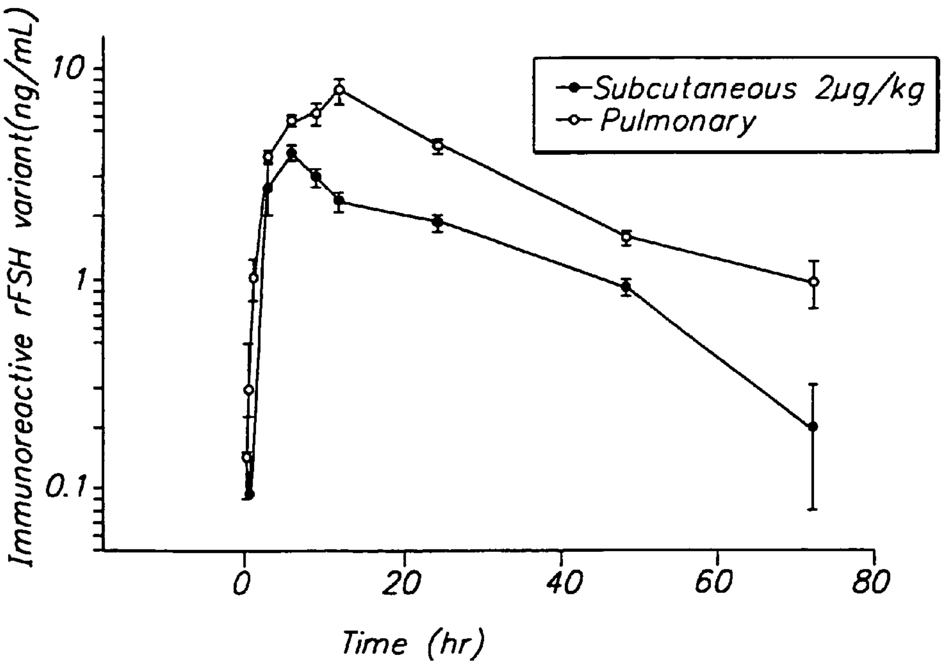
FIG. 5 provides a graphical representation of mean serum concentrations (±SEM) of an immunoreactive a hFSH variant in cynomolgus monkeys following pulmonary and subcutaneous administration (Example 17).
Figure 6:
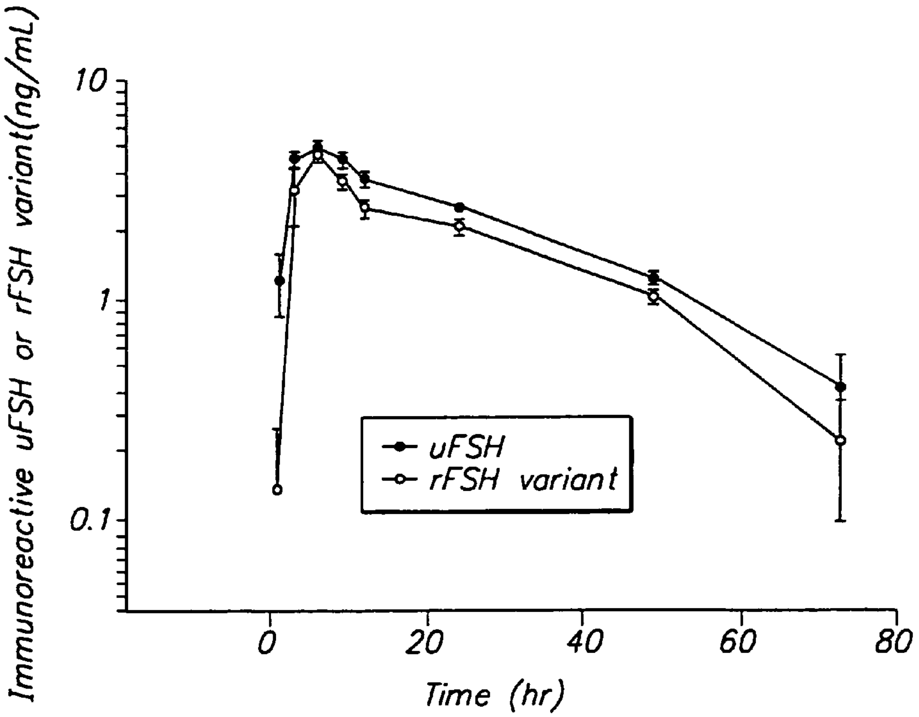
FIG. 6 provides a graphical comparison of the mean serum concentrations (±SEM) of an immunoreactive a hFSH variant or uFSH following subcutaneous administration (Example 17).

$AUC_{0-\infty}$ was used in this calculation. Individual concentrations of immunoreactive uFSH in monkey serum are reported in Table 11. The results of the pharmacokinetic analysis are reported in Table 12. Mean serum concentrations (±SEM) are depicted graphically in FIG. 4.

Figure 3:
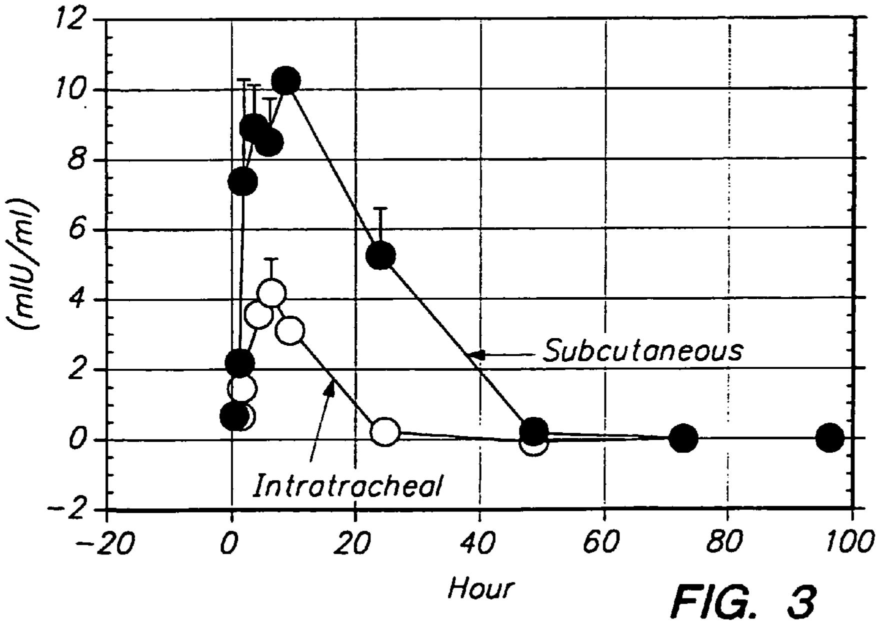
FIG. 3 provides a graphical comparison of the in vivo bioavailability in rats of uFSH administered intratracheally (IT) and subcutaneously (SC) (Example 9).

On the day of the experiment, rats were anaesthetized for IT dosing and were then allowed to recover. Animals were then sacrificed at the given times and a total blood sample was obtained. Individual rats were used for each time point. Blood samples were collected at 0, 1, 2, 4, 6, 9, 24 hours (day 1), and at 48 (day 2), 72 (day 3), and 96 (day 4) hours. Samples were centrifuged and the supernatants were frozen at −80° C. until analyses using RIA kits from ICN Biomedicals (Costa Mesa, Calif.). The results are summarized in Table 10 below and graphically in FIG. 3.

TABLE 10

Bioavailabiity of SC and IT Administered FSP in Rats

| Dose/Source | Route | Tmax, hour | Cmax mIU/ml | AUC mIU/ml.hr | f (%) |
|---|---|---|---|---|---|
| 0.9 U/* | SC | 8 | 6.6 | 94.05 | |
| 9.0 U/* | SC | 4 | 13.1 | 420.37 | |
| 9.0 U/** | SC | 9 | 10.25 | 251.3 | |
| 9.0 U/** | IT | 6 | 4.14 | 53.63 | 21.4 |

Source: * = human pituitary-derived; ** = human urinary-derived
FSP Dose = Units/200 µL/rat
Tmax: time at which maximum drug concentration in plasma is reached
Cmax: maximum drug concentration reached (at Tmax)
AUC: total area under the drug level-time curve for elimination of drug
f: bioavailability in % = $AUC_{IT}/AUC_{SC}$.

The above results provide an indication of the bioavailability of intratracheally-delivered FSP, and reveal a relative IT bioavailability of about 20 percent in comparison to SC-delivered FSP. The results of this preliminary study indicate that FSP has a reasonable bioavailability when instilled in liquid form into the rat trachea. This data further suggests that FSP can be administered to the lung, and absorbed through the lower respiratory tract and into systemic circulation.

TABLE 11

Serum Concentrations of Immunoreactive FSH in Cynomolgus Monkeys Following Pulmonary and Subcutaneous Administration of uFSH and Pharmacokinetic Statistics

| | Animal Number/Concentration (mIU/mL) | | | | | | |
|---|---|---|---|---|---|---|---|
| Time (h) | 82841 | 82861 | 83871 | 83921 | 84761 | Mean | SEM |
| SC - 2 μg/kg | | | | | | | |
| 0 | BQL[1] | BQL | BQL | BQL | BQL | 0 | |
| 1 | 5.3 | 4.6 | BQL | 5.3 | BQL | 3.0 | 1.3 |
| 3 | 20.9 | 63.7 | 28.2 | 65.5 | 36.3 | 42.9 | 9.2 |
| 6 | 25.4 | 75.7 | 28.9 | 97.1 | 68.5 | 59.1 | 13.9 |
| 9 | 20.2 | 58.3 | 31.5 | 71.3 | 76.0 | 51.5 | 11.0 |
| 12 | 18.7[2] | 46.8[2] | 33.4[2] | 55.0[2] | 54.3[2] | 41.6 | 6.9 |
| 24 | 20.7[2] | 36.8[2] | 29.1[2] | 38.0[2] | 40.5[2] | 33.0 | 3.6 |
| 48 | 15.7[2] | 20.8[2] | 17.4[2] | 17.4[2] | 14.5[2] | 17.2 | 1.1 |
| 72 | 9.2[2] | 9.8[2] | 8.4[2] | 8.6[2] | 5.8[2] | 8.4 | 0.7 |
| $AUC_{0-t}$ (mIU*h/mL) | 1197.1 | 2198.4 | 1544.4 | 2294.2 | 2078.1 | 1862.4 | 210.9 |
| $AUC_{0-\infty}$ (mIU*h/mL) | 2013.4 | 2594.5 | 1932.5 | 2566.8 | 2231.3 | 2267.7 | 136.9 |
| Half-Life (h) | 55.5 | 26.6 | 29.8 | 22.3 | 18.1 | 26.4 | 4.3 |
| $C_{Max}$ (mIU/mL) | 25.4 | 75.7 | 33.4 | 97.1 | 76.0 | 61.5 | 13.7 |
| $T_{Max}$ (h) | 6.0 | 6.0 | 12.0 | 6.0 | 9.0 | 7.8 | 1.2 |
| Dose (μg/kg) | 2 | 2 | 2 | 2 | 2 | 2 | |
| PUL - 18.4 ± 1.3 μg/kg | | | | | | | |
| 0 | BQL | BQL | BQL | BQL | BQL | 0 | |
| 0.08 | BQL | BQL | BQL | BQL | BQL | 0 | |
| 0.25 | BQL | BQL | BQL | BQL | BQL | 0 | |
| 0.5 | BQL | BQL | BQL | BQL | BQL | 0 | |
| 1 | BQL | BQL | BQL | BQL | 4.4 | 0.9 | 0.9 |
| 3 | 6.9 | 13.1 | 6.4 | 5.5 | 16.6 | 9.7 | 2.2 |
| 6 | 20.0 | 21.0 | 16.6 | 18.8 | 33.0 | 21.9 | 2.9 |
| 9 | 29.1 | 24.3 | 19.4 | 17.2 | 40.1 | 26.0 | 4.1 |
| 12 | 26.6[2] | 25.2[2] | 24.4[2] | 20.4[2] | 40.0[2] | 27.3 | 3.3 |
| 24 | 19.6[2] | 20.4[2] | 13.7[2] | 16.3[2] | 31.3[2] | 20.3 | 3.0 |
| 48 | 7.4[2] | 9.3[2] | 6.9[2] | 9.0[2] | 10.7[2] | 8.7 | 0.7 |
| 72 | 3.9[2] | 4.5[2] | 3.0[2] | 5.3[2] | 4.2[2] | 4.2 | 0.4 |
| $AUC_{0-t}$ (mIU*h/mL) | 941.3 | 1001.8 | 755.2 | 847.8 | 1436.9 | 996.6 | 117.8 |
| $AUC_{0-\infty}$ (mIU*h/mL) | 1053.5 | 1157.9 | 843.4 | 1079.3 | 1546.8 | 1136.0 | 115.1 |
| Half-Life (h) | 20.9 | 23.5 | 20.5 | 30.4 | 17.83 | 21.9 | 1.8 |
| $C_{Max}$ (mIU/mL) | 29.1 | 25.2 | 24.4 | 20.4 | 40.1 | 27.8 | 3.4 |
| $T_{Max}$ (h) | 9.0 | 12.0 | 12.0 | 12.0 | 9.0 | 10.8 | 0.7 |
| Dose (μg/kg) | 19 | 19 | 22 | 14 | 18 | 18.4 | 1.3 |
| Percent Bioavailability | 5.5 | 4.7 | 4.0 | 6.0 | 7.7 | 5.6 | 0.6 |
| PUL - 37.2 ± 3.9 μg/kg | | | | | | | |
| 0 | BQL | BQL | BQL | BQL | BQL | 0 | |
| 0.33 | BQL | BQL | BQL | BQL | BQL | 0 | |
| 0.5 | BQL | BQL | 4.3 | BQL | BQL | 0.86 | 0.86 |
| 0.75 | 3.8 | BQL | 6.6 | BQL | BQL | 2.1 | 1.4 |
| 1.25 | 57.6 | BQL | 31.0 | 4.7 | BQL | 18.7 | 11.3 |
| 3.25 | 32.7 | 10.4 | 50.1 | 12.2 | 13.4 | 23.8 | 7.7 |
| 6.25 | 69.3 | 22.7 | 85.2 | 23.7 | 29.0 | 46.0 | 13.1 |
| 9.25 | 82.4 | 30.6 | 132.8 | 33.8 | 36.8 | 63.3 | 19.8 |
| 12.25 | 72.5[2] | 36.0[2] | 155.0[2] | 36.7[2] | 39.8[2] | 68.0 | 22.8 |
| 24.25 | 55.4[2] | 32.7[2] | 94.6[2] | 30.4[2] | 36.6[2] | 49.9 | 12.0 |
| 48.25 | 29.3[2] | 17.5[2] | 47.8[2] | 15.5[2] | 14.2[2] | 24.9 | 6.4 |
| 72.25 | 14.1[2] | 9.2[2] | 19.4[2] | 8.6[2] | 6.0[2] | 11.5 | 2.4 |
| $AUC_{0-t}$ (mIU*h/mL) | 3023.6 | 1574.9 | 5069.1 | 1506.5 | 1601 | 2555.0 | 689.6 |
| $AUC_{0-\infty}$ (mIU*h/mL) | 3554.7 | 1981.5 | 5659.1 | 1845.2 | 1790.4 | 2968.0 | 747.9 |
| Half-Life (h) | 25.3 | 29.4 | 20.52 | 27.9 | 20.9 | 24.3 | 1.8 |
| $C_{Max}$ (mIU/mL) | 82.4 | 36.0 | 155.0 | 36.7 | 39.8 | 70.0 | 23.0 |
| $T_{Max}$ (h) | 9.3 | 12.3 | 12.3 | 12.3 | 12.3 | 11.7 | 0.6 |
| Dose (μg/kg) | 38 | 47 | 43 | 33 | 25 | 37.2 | 3.9 |
| Percent Bioavailability | 9.3 | 3.2 | 13.6 | 4.4 | 6.4 | 7.4 | 1.9 |
| PUL - 3.8 ± 1.7 μg/kg | | | | | | | |
| 0 | BQL | BQL | BQL | BQL | BQL | 0 | |
| 0.08 | BQL | BQL | BQL | BQL | BQL | 0 | |
| 0.25 | BQL | BQL | BQL | BQL | BQL | 0 | |
| 0.5 | BQL | BQL | BQL | BQL | BQL | 0 | |
| 1 | BQL | BQL | BQL | BQL | BQL | 0 | |
| 3 | BQL | BQL | BQL | BQL | BQL | 0 | |

TABLE 11-continued

Serum Concentrations of Immunoreactive FSH in Cynomolgus Monkeys Following Pulmonary and Subcutaneous Administration of uFSH and Pharmacokinetic Statistics

| | Animal Number/Concentration (mIU/mL) | | | | | | |
|---|---|---|---|---|---|---|---|
| Time (h) | 82841 | 82861 | 83871 | 83921 | 84761 | Mean | SEM |
| 6 | BQL | 3.1 | 4.5 | 3.7 | 3.7 | 3.8 | 0.3 |
| 9 | BQL | 4.5 | 6.1 | 4.9 | 4.3 | 5.0 | 0.4 |
| 12 | BQL | 4.6 | 8.1 | 5.2 | 4.7 | 5.7 | 0.8 |
| 24 | BQL | 4.2 | 8.5 | 5.6 | 3.9 | 5.6 | 1.1 |
| 48 | BQL | BQL | 4.9 | 3.0 | BQL | 4.0 | NC[(3)] |
| 72 | BQL | BQL | BQL | BQL | BQL | 0 | |
| $AUC_{0-t}$ (mIU*h/mL) | 0 | 132.9 | 363.2 | 237.6 | 129.5 | 172.6 | 60.7 |
| $AUC_{0-\infty}$ (mIU*h/mL) | NC | NC | NC | NC | NC | NC | NC |
| Half-Life (h) | NC | NC | NC | NC | NC | NC | |
| $C_{Max}$ (mIU/mL) | 0 | 4.6 | 8.5 | 5.6 | 4.7 | 4.7 | 1.4 |
| $T_{Max}$ (h) | 0 | 12 | 24 | 24 | 12 | 14.4 | 4.5 |
| Dose (μg/kg) | 6 | 2 | 3 | 5 | 3 | 3.8 | 1.7 |
| Percent Bioavailability | NC | NC | NC | NC | NC | NC | |

h = hour; MIU = milli-International Units; mL = milliliter; SEM = standard error of mean; μg = microgram; kg = killogram; $C_{max}$ = maximum concentration; $AUC_{0-t}$ = area under the curve extrapolated from time 0 to tau; $AUC_{0-\infty}$ = area under the curve extrapolated from time 0 to infinity; $T_{max}$ = time to maximum plasma concentration.
(1)BQL means below the limit of quantitation, which is, defined as 3.0 ng/mL and for calculations, BQL values were assigned a value of zero.
(2)Time points used for calculating the half-life.
(3)NC means not calculated.

TABLE 12

Pharmacokinetic Parameters for Cynomolgus Monkeys after Pulmonary and Subcutaneous Administration of uFSH

| | SC | | Pulmonary Mid Dose | | Pulmonary High Dose | | Pulmonary Low Dose | |
|---|---|---|---|---|---|---|---|---|
| | Mean | SEM | Mean | SEM | Mean | SEM | Mean | SEM |
| $AUC_{0-t}$ (mIU*h/mL) | 1862 | 211 | 997 | 118 | 2555 | 690 | 173 | 61 |
| $AUC_{0-\infty}$ (mIU*h/mL) | 2268 | 137 | 1136 | 115 | 2968 | 748 | NC | NC |
| Half-Life (h) | 26.4 | 4.3 | 21.9 | 1.8 | 24.3 | 1.8 | NC | |
| $C_{Max}$ (mIU/mL) | 61.5 | 13.7 | 27.8 | 3.4 | 70.0 | 23.0 | 4.7 | 1.4 |
| $T_{Max}$ (h) | 7.8 | 1.2 | 10.8 | 0.7 | 11.7 | 0.6 | 14.4 | 4.5 |
| Dose (μg/kg) | 2 | — | 18.4 | 1.3 | 37.2 | 3.9 | 3.8 | 1.7 |
| Bioavailability (%) | 100 | | 5.6 | 0.6 | 7.4 | 1.9 | NC | |

The serum pharmacokinetic results demonstrated that the serum concentration time profiles following pulmonary delivery were similar to subcutaneous administration. The terminal half-life following pulmonary delivery was similar to that obtained with subcutaneous administration (approximately 24 hours). Within the pulmonary dose groups (mid and high doses) the serum $AUC_{0-\infty}$ and $C_{max}$ increased in relation to increasing dose administered to the lung. Finally, the average percent bioavailability of aerosol formulated uFSH delivered by the pulmonary route compared to subcutaneous administration averaged approximately 6.5% based on the inhaled dose. The corresponding in-lung bioavailability, or relative pulmonary bioavailability, is estimated to be 26% based on the measurements of pulmonary deposition of 2 μm MMAD particles in monkeys using gamma scintography. The low dose pulmonary PK was not used in these calculations because there were too few samples taken when the FSH blood levels were measurable. These findings indicate that dry powders of FSP can be successfully administered by the pulmonary route to cynomolgus monkeys, to other mammals, and particularly to other primates such as humans, resulting in serum concentrations and profiles similar to those obtained by the widely practiced subcutaneous route.

Example 11

Respirable FSH Dry Powders Containing Leucine

Powder lots 99348 and 99349 were spray dried under conditions as described in Example 2 for the L2010 powders. These formulations each incorporated leucine at 40% (w/w); the remainder of the formulation matrix was mannitol and sodium citrate in a similar relative ratio as is present in L2010. The uFSH content in the powders was 5% and 2%, for lots 99348 and 99349, respectively. For the composition containing 2% FSH, the fill mass in the blister pack was 5 mg, while for the 5% FSH dry powder composition, the fill mass in the blister pack was 2 mg. Each of the two spray-dried leucine formulations possessed good uFSH stability, comparable to those of non-leucine containing formulations as determined by SEC-HPLC (data for non-leucine-containing formulations can be found in Table 3).

TABLE 13

Effect of Spray Drying on Higher Order Aggregate (HOA) content in uFSH Powders Formulated with L-Leucine

| uFSH:citrate:mannitol:leucine (wt:wt:wt:wt) | Lot # | Form. # | % total HOA Before spray drying | After spray drying |
|---|---|---|---|---|
| 5:48:7:40 | 99348 | L2029 | 0.6 | 1.8 |
| 2:50:8:40 | 99349 | L2030 | 0.6 | 1.8 |
| 2:83:15:0 | 99347 | L2028 | 0.4 | 2.3 |

The two leucine formulations showed superior aerosol performance compared to all other formulations tested. A 14 to 30% absolute increase in DDE was observed and was accompanied by a decrease in the "% Left" in the blister pack. The aerosol performance coefficient (APC) increased significantly, to more than 0.60.

TABLE 14

Aerosol performance of L-Leucine-containing powders

| Lot | BP fill mass | Description | DDE (%) | SD | % Left | SD | APC |
|---|---|---|---|---|---|---|---|
| 99348 | 2 mg | 5% uFSH w/leucine | 71.1 | 5.7 | 15.2 | 3.7 | 0.64 |
| 99349 | 5 mg | 2% uFSH w/leucine | 74.2 | 5.0 | 13.3 | 4.2 | 0.60 |
| 99295 | 2 mg | 5% uFSH | 56.9 | 10.7 | 24.2 | 10.8 | 0.37 |
| 99347 | 5 mg | 2% rFSH | 44.5 | 2.7 | 17.1 | 3.3 | 0.32 |

Additionally, the morphology of the particles, as viewed by SEM, was altered by the addition of the amino acid. The particles seem more "collapsed" and thus the surface folding was more pronounced. In the limited fields of view available with these micrographs, the particle size distribution seemed more homogenous with few very fine particles evident. Additional FSP-leucine formulations were prepared as above, to further examine their aerosol and stability properties.

TABLE 15

Comparison of ED values for leucine and non-leucine powders.

| Lot # | Composition (wt %) FSP | citrate | mannitol | raffinose | leucine | ED (%)[1] mean (n = 10) initial | 4 months |
|---|---|---|---|---|---|---|---|
| 99420 | 5 | 80 | 15 | 0 | 0 | 60.8 | n.d. |
| 99421 | 5 | 42.5 | 10 | 42.5 | 0 | 62.9 | n.d. |
| 99422 | 5 | 20 | 0 | 75 | 0 | 53.2 | n.d. |
| 99423 | 5 | 0 | 0 | 55 | 40 | 70.9 | 65.3 |
| 99425 | 5 | 0 | 0 | 35 | 60 | 74.4 | 75.8 |
| 99426 | 5 | 55 | 0 | 0 | 40 | 65.3 | 67.1 |
| 99455 | 5 | 47.7 | 7.3 | 0 | 40 | 71.6 | 66.3 |
| 99454[2] | 5 | 47.7 | 7.3 | 0 | 40 | 72.7 | n.d. |
| 99457 | 5 | 25 | 0 | 10 | 60 | 70.4 | 71.5 |

[1]all powders evaluated with 2 mg fill weight.
[2]lot 99454 made with uFSH.
n.d. indicates ED testing not performed at 4 months.

Each of the six leucine-containing formulations demonstrated a higher DDE from the mouthpiece of the device than the three formulations that did not contain leucine. No significant changes in DDE were observed after 4 months of storage at 40° C., indicating that these leucine containing formulations retain their highly dispersible nature, even under accelerated stability testing conditions. The properties of additional similarly prepared FSP leucine-containing dry powders are provided in the tables below.

TABLE 16

Initial and one month aerosol performance of four exemplary FSP Dry Powder Formulations containing 15% FSH and placed on accelerated stability (40° C./75% RH in foil pouch)

| Lot # | Composition (wt %) FSH | citrate | mannitol | raffinose | leucine | ED (%) initial, 1 month[1] | MMAD (μm) |
|---|---|---|---|---|---|---|---|
| 99513 | 15 | 42.5 | 0 | 42.5 | 0 | 55.7, 56.3 | 2.8, 3.0 |
| 99514 | 15 | 45 | 0 | 0 | 40 | 63.9, 65.1 | 2.2, 2.3 |
| 99515 | 15 | 2 | 0 | 43 | 40 | 68.7, 66.1 | 2.3, 2.3 |
| 99516 | 15 | 72 | 13 | 0 | 0 | 58.6, 59.9 | 2.8, 2.9 |

[1]all powders evaluated with 3 mg fill weights.

TABLE 17

Physical Characterization of Leucine-Containing Dry Powders

| ID | Lot | FSP | Leucine | Citrate | Yield (%) | MMD (μm) | $H_2O$ (%) | $T_g$ (° C.) | L.C. (%) |
|---|---|---|---|---|---|---|---|---|---|
| L2041 | 99598 | 2 | 40 | 58 | 79 | 1.2, 1.6 | 2.7 | 106 | 35 |
| L2042 | 99599 | 2 | 80 | 18 | 72 | 1.3 | 1.3 | 100 | 62 |
| L2043 | 99600 | 2 | 95 | 3 | 71 | 1.1 | 0.5 | n.o. | 80 |
| L2044 | 99601 | 8 | 60 | 32 | 78 | 1.2 | 1.7 | 112 | 45 |

TABLE 17-continued

| Physical Characterization of Leucine-Containing Dry Powders | | | | | | | | | |
|---|---|---|---|---|---|---|---|---|---|
| ID | Lot | FSP | Leucine | Citrate | Yield (%) | MMD (μm) | $H_2O$ (%) | $T_g$ (° C.) | L.C. (%) |
| L2032 | 99602 | 15 | 40 | 45 | 83 | 1.4 | 2.4 | t.b.d. | 32[2] |
| L2045 | 99603 | 15 | 80 | 5 | 79 | 1.4 | 1.0 | n.o. | 54[1] |

L.C. = leucine crystallinity

TABLE 18

ED and Percent Fine Particle as a Function of BP Fill Weight and Formulation for Leucine Containing Dry Powders of FSP

| Lot No. | Formulation FSP:citrate:leucine | BP fill wt. (mg) | % ED mean (RSD) (n = 16) | % Fine Particle (n = 3) |
|---|---|---|---|---|
| 99598 | 2:58:40 | 2 | 76 (6) | 53 |
| | | 3 | 74 (4) | |
| | | 4 | 76 (5) | 53 |
| | | 5 | 76 (5) | |
| 99599 | 2:18:80 | 2 | 80 (7) | 51 |
| | | 3 | 81 (4) | |
| | | 4 | 81 (4) | 41 |
| | | 5 | 81 (3) | |
| 99600 | 2:3:95 | 2 | 83 (7) | 50 |
| 99601 | 8:32:60 | 2 | 75 (6) | 55 |
| | | 4 | 78 (4) | 52 |
| 99602 | 15:45:40 | 2 | 77 (8) | 53 |
| | | 3 | 73 (8) | |
| | | 4 | 74 (5) | 51 |
| 99603 | (15:5:80 | 2 | 78 (5) | 57 |
| | | 4 | 80 (4) | 54 |

Example 12

Expression of an FSH Variant in AV12 Cells

An expression cassette vector pGTH was used for expression of the FSH alpha subunit in AV12. Briefly, pGTH contains several elements in sequence: the SV40 early promoter/ori, *E. coli* hygromicin resistance, SV40 small "t" antigen splice site/poly-A site, pBR322 cloning remnant, BK virus (strain P2) cloning remnant, Poly-$CA_{20}$/$GT_{20}$ element (synthetic oligonucleotide), BK virus (strain P2) enhancer, AD2 major late promoter/spliced tripatite leader, BclI insertion site for the FSH alpha subunit coding sequence (including stop codon), SV40 small "t" antigen splice site/poly-A site; and pBR322 ampicillin resistance/ori.

The plasmid construct pGTH-alpha was generated to express the encoded the human alpha subunit sequence (SEQ ID NO: 5) by cloning a 362-bp BclI FSH variant cDNA fragment into the unique BclI site of the vector. The FSH variant alpha cDNA fragment DNA was generated by PCR amplification using the shuttle plasmid pLGD637 as template (pLGD637 contains a synthetic/oligonuclotide-assembled FSH variant alpha cDNA sequence (SEQ ID NO: 37). The integrity of BclI insert was confirmed by sequencing followed by comparison to the GenPept database (Accession Number 31869).

An expression cassette vector pGTD was used to express a human beta subunit FSH variant sequence encoding SEQ ID NO: 11 (i.e., nucleotide SEQ ID NO: 38). pGTD contains several elements for expression in AV12 cells: sequentially, the BK virus (strain P2) cloning remnant, Poly-$CA_2O$/$GT_{20}$ element (synthetic oligonucleotide), BK virus (strain P2) enhancer, AD2 major late promoter/spliced tripartite leader, BclI insertion site for the FSH variant beta subunit coding sequence (including stop codon), SV40 small "t" antigen splice site/poly-A site; SV40 early promoter ori, Murine dihydrofolate reductase cDNA, SV40 small "t" antigen splice site/poly-A site, and pBR322 ampicillin resistance/ori.

The plasmid construct pGTD-bCD3 was generated by cloning a 393-bp BclI FSH variant beta-bCD3 cDNA fragment into the unique BclI site of the pGTD vector (see SEQ ID NO: 38). The FSH variant beta-CD3 cDNA fragment DNA was generated by PCR amplification, using the shuttle plasmid pLGD638 as template (pLGD638 contains a synthetic/oligonucleotide-assembled FSH variant beta cDNA sequence). The integrity of the construct was confirmed by sequencing and compared with the human beta subunit sequence deposited in the GenPept database (Accession Number 476441).

In brief, the pGTH-alpha and pGTD-bCD3 plasmids were linearized, repurified, and then co-transfected into adherent AV23-RGT18 cells. Following selection with medium containing 0.25 uM methotrexate and 100 μg/ml hygromicin-B, along with 200 μg/ml G418 to maintain the glutamate transporter genotype of the AV12-RGT18 cells, individual stable clones were isolated either manually or via flow-assisted cell sorting. Highest producing clones were identified by analysis of conditioned medium with a commercial FSH ELISA kit to measure FSH variant production. Several clones were adapted to serum-free suspension and further amplified to obtain isolatable quantities of the FSH variant heterodimer.

Example 13

N-Terminal Truncated FSH Variant Forms

Analysis of Protein Sequence by N-terminal Sequencing. Multiple lots of recombinant hFSH variant were produced in fermentation in the laboratory and quantified using a variety of assays. The host (CHO cells) was designed to express an alpha subunit encoded by SEQ ID NO:37 and a beta subunit encoded by SEQ ID NO:38. All the N-terminal sequencing was done using either solutions or blotted samples. Only relative ratios of intact and N-2 alpha and beta subunits can be obtained from N-terminal sequence data. For example, the presence of Cys is not quantifiable by N-terminal sequencing and Ser exhibits a lower than average recovery, which makes it more difficult to accurately estimate relative ratios of intact and N-2 beta-subunits by this method (beta-subunits have Ser and Cys at positions 2 and 3 respectively). Relative amounts of amino termini are estimate using the second cycle recoveries, e.g., Ser and Glu. Some representative results are summarized in Table 19 below.

TABLE 19

| Truncation at N-terminus of CHO-derived FSH | | |
|---|---|---|
| Protein | α-subunit[a] (% N-2) | β-subunit (% N-2)[b] |
| WUJ-38 | 7.9 | 58 |
| WUQ-90 | 11 | 60 |
| WUQ-115 | 10 | 59 |
| WWG-15 | 9.5 | 59 |
| WWG-30 | 9.2 | 59 |
| WWG-50 | 8.7 | 57 |
| FSH | 8.6 | 66 |

[a]Estimates based on recoveries in the first cycle. Examination of tryptic peptides for WUJ-38 and WUQ-115 by LC/MS indicates 94 and 92.7% respectively of intact N-2 alpha subunit.

[b]Estimates. Examination of tryptic peptides for WUJ-38 and WUQ-115 by LC/MS indicates a 1:1 ratio of intact and N-2 variant beta subunits.

Example 14

C-Terminal Truncated FSH Variant Forms Quantitated by Tryptic Mapping and LC/MS Six lots of Chinese Hamster Ovary cells modified to biosynthesize hFSH variant having an alpha subunit encoded by DNA of SEQ ID NO:37 and having a beta subunit encoded by DNA of SEQ ID NO:38 (coding for 108 amino acids) were grown at laboratory scale. The expressed FSH variant proteins were purified and were analyzed for heterogeneity of the beta subunit C-terminus. C-terminus sequence data from three independent LC/MS runs on FSH variant preparations are shown below in Table 20.

TABLE 20

| Truncation of the C-terminus of FSH variant beta subunit | | | |
|---|---|---|---|
| Lot No. | 108 amino acids | 107 amino acids | 106 amino acids |
| WUJ-38[a,b] | 84.2 | 1.5 | 14.2 |
| WUQ-90 | 96 | 2.2 | 1.7 |
| WUQ-115[c] | 3.8 | 7.8 | 88.4 |
| WWG-15 | 62 | 15 | 22 |
| WWG-30 | 94 | 2 | 4 |
| WWG-50 | 63.3 | 12.1 | 24.6 |

[a]separate run for WUJ-38, 73.5, 7, and 20% was obtained for the three forms, respectively.

[b]In a separate run for WUJ-38, 83% and 17% for 108 and 106 amino acid were obtained, respectively.

[c]In a separate run for WUQ-115, 25 and 75% were obtained for CD3 and CD5, respectively.

Example 15

Biological Activity of FSH Variants

In vivo activity data obtained on the different lots of the FSH variant showed similar potency of the hormone in a rat ovarian weight gain assay and are shown in Table 21. In vivo activity of FSH variants compared to urinary FHS (uFSH) was measured by the Steelman/Pohley rat ovarian weight gain assay (Steelman and Pohley, 1953, Endocrinology, 53, 604–616). Hypophysectomized immature female rats (23–25 days) were housed with controlled lighting. The rats were given daily subcutaneous treatment with hFSH variant or vehicle (PBS with 0.1% BSA, ~0.25 mL). A dose of 0.1, 0.3, 1.0 or 3.0 μg/day was used. The treatment was repeated at 24 hour intervals for 4 days. The rats were weighed and sacrificed 24 hr after 4th dose, the ovaries and uterus were trimmed of fat and weighed. Six rats were used for each dose. FSH variant samples were prepared as follows: samples were dialyzed in PBS buffer (GIBCOBRL) for 3 hrs with 10,000 MWCO dialysis cassettes from Pierce. The concentration of the sample was determined with an AVIV UV spectrometer using an extinction coefficient of 1.06 at 278 nm for 1 mg/ml solution in 1-cm path length cell.

TABLE 21

In vivo activity of FSP (FSH variants) as measured by rat ovarian weight (Ov wt) and uterine weight (Ut wt) gain as a function of FSH dose

| Dose | uFSH | | WUJ-38 | | WUQ-090 | | WUQ-115 | |
|---|---|---|---|---|---|---|---|---|
| (μg/day) | Ov wt (mg) | Ut wt (mg) | Ov wt (mg) | Ut wt (mg) | Ov wt (mg) | Ut wt (mg) | Ov wt (mg) | Ut wt (mg) |
| 0 | 11.2 | 15.0 | 11.2 | 15.0 | 11.7 | 13.2 | 11.7 | 13.2 |
| 0.1 | 31.5 | 33.0 | 26.8 | 33.7 | 22.0 | 26.7 | 22.4 | 17.0 |
| 0.3 | 35.0 | 62.0 | 40.2 | 66.2 | 33.0 | 49.3 | 44.5 | 63.3 |
| 1 | 49.2 | 78.8 | 38.2 | 77.2 | 36.5 | 72.5 | 39.7 | 70.2 |
| 3 | 41.2 | 82.7 | 42.8 | 77.5 | 40.7 | 87.0 | 42.0 | 75.7 |

Example 16

Pharmacokinetics of uFSH Compared to an FSH Variant in Female Fisher Rats

The following studies measure the pharmacokinetics (PK) of a hFSH variant compared with uFSH in Fisher Rats following intravenous (IV) and subcutaneous (SC) administration. Female Fisher Rats were administered uFSH or a hFSH variant (15 μg/kg) by SC and IV routes. The hFSH variant was recombinantly produced in cells expressing an alpha subunit having the amino acid sequence of SEQ ID NO:5 and a beta subunit having the amino acid sequence of SEQ ID NO:11. Whole blood samples were collected at 0.08, 0.25, 0.5, 1, 3, 6, 9, 12, and 24 hrs post-dose. Serum concentrations of immunoreactive uFSH or hFSH variant were determined by immunoradiometric assay employing a modified commercial FSH kit, FSH IRMA, DPC® Ltd. (Los Angeles, Calif.). RIASYS, a software program that employs a weighted 4-parameter logistic model algorithm, was used to analyze IRMA binding data. Serum concentrations of immunoreactive uFSH or hFSH variant were estimated from a standard curve. Standards in rat serum ranged between 3.5 and 3500 mIU/mL. The lower limit of quantitation was 5 mIU/mL. The upper limit of quantitation was 750 mIU/mL. A pharmacokinetic analysis of the serum concentration data was conducted using a statistical package. Individual concentrations of immunoreactive uFSH and hFSH variant in rat serum following SC and IV administration are reported in Table 23 and Table 24, respectively. Pharmacokinetic (PK) values are reported in Table 25.

TABLE 23

Serum Concentrations (mIU/mL) of Immunoreactive uFSH in Female Fisher Rats Following Subcutaneous or Intravenous Administration of 15.0 μg/kg of uFSH

| | Time (h) | | | | | | | | |
|---|---|---|---|---|---|---|---|---|---|
| uFSH IV | 0.08 | 0.25 | 0.5 | 1 | 3 | 6 | 9 | 12 | 24 |
| Rat | | | | | | | | | |
| 1 | 1894 | | | 645 | | | 109 | | |
| 2 | 2435 | | | 856 | | | 78 | | |
| 3 | 2447 | | | 920 | | | 85 | | |
| 4 | | 2992 | | | 477 | | | 84 | |
| 5 | | 103 | | | 308 | | | 145 | |
| 6 | | 1223 | | | 351 | | | 131 | |
| 7 | | | 1604 | | | 224 | | | 38 |
| 8 | | | 2031 | | | 198 | | | 24 |
| 9 | | | 1888 | | | 200 | | | 23 |
| Mean | 2258 | 1439 | 1841 | 807 | 379 | 207 | 91 | 120 | 28 |
| SEM | 182 | 841 | 125 | 83 | 51 | 8.4 | 9.5 | 18.5 | 4.7 |
| uFSH SC | 0.08 | 0.25 | 0.5 | 1 | 3 | 6 | 9 | 12 | 24 |
| Rat | | | | | | | | | |
| 10 | 5.5 | | | 37.9 | | | 143 | | |
| 11 | BQL | | | 23.8 | | | 165 | | |
| 12 | BQL | | | 34.8 | | | 117 | | |
| 13 | | BQL | | | 95 | | | 126 | |
| 14 | | 15.8 | | | 139 | | | 144 | |
| 15 | | 9.3 | | | 170 | | | 153 | |
| 16 | | | 15.4 | | | 138 | | | 75.4 |
| 17 | | | 37.2 | | | 168.1 | | | 70.1 |
| 18 | | | 15.2 | | | 150.4 | | | 74.5 |
| Mean | 1.8 | 8.4 | 22.6 | 32.2 | 135 | 152 | 142 | 141 | 73.3 |
| SEM | 1.8 | 4.6 | 7.3 | 4.3 | 21.7 | 8.7 | 13.9 | 7.9 | 1.6 |

TABLE 24

Serum Concentrations (mIU/mL) of Immunoreactive FSH variant in Female Fisher Rats Following Subcutaneous or Intravenous Administration of 15.0 μg/kg of FSH variant

| | Time (h) | | | | | | | | |
|---|---|---|---|---|---|---|---|---|---|
| | 0.08 | 0.25 | 0.5 | 1 | 3 | 6 | 9 | 12 | 24 |
| FSH variant IV Rat | | | | | | | | | |
| 1 | 3689 | | | 1150 | | | 79 | | |
| 2 | 3994 | | | 1348 | | | 90 | | |
| 3 | 3816 | | | 1248 | | | 85 | | |
| 4 | | 2671 | | | 407 | | | 54 | |
| 5 | | 2743 | | | 432 | | | 56 | |
| 6 | | 2399 | | | 316 | | | 36 | |
| 7 | | | 2047 | | | 150 | | | 19 |
| 8 | | | 1937 | | | 145 | | | 20 |
| 9 | | | 1947 | | | 166 | | | 17 |
| Mean | 3833 | 2604 | 1977 | 1249 | 385 | 154 | 84 | 49 | 18.7 |
| SEM | 88 | 105 | 35 | 57 | 35 | 6.1 | 3.0 | 6.3 | 1.0 |
| FSH variant SC Rat | | | | | | | | | |
| 10 | BQL | | | 36.5 | | | 152 | | |
| 11 | BQL | | | 36.7 | | | 172 | | |
| 12 | BQL | | | 28.1 | | | 139 | | |
| 13 | | 10.2 | | | 112 | | | 111 | |
| 14 | | 12.2 | | | 215 | | | 123 | |
| 15 | | 5.8 | | | 116 | | | 100 | |
| 16 | | | 17.9 | | | 162 | | | 53.8 |
| 17 | | | 23.0 | | | 175 | | | 62.4 |
| 18 | | | 28.1 | | | 183 | | | 62.9 |

TABLE 24-continued

Serum Concentrations (mIU/mL) of Immunoreactive FSH variant in Female Fisher Rats Following Subcutaneous or Intravenous Administration of 15.0 μg/kg of FSH variant

| | Time (h) | | | | | | | | |
|---|---|---|---|---|---|---|---|---|---|
| | 0.08 | 0.25 | 0.5 | 1 | 3 | 6 | 9 | 12 | 24 |
| Mean | 0 | 9.4 | 23.0 | 33.8 | 148 | 173 | 154 | 111 | 59.7 |
| SEM | 0 | 1.9 | 2.9 | 2.8 | 34 | 6.1 | 9.5 | 6.8 | 3.0 |

TABLE 25

Pharmacokinetic Parameters for Female Fisher Rats after Intravenous and Subcutaneous Administration of uFSH or FSH variant

| Treatment | Dose (μg/kg) | $C_{max}$ (mIU/mL) | $AUC_{0-t}$ (mIU · h/mL) | $AUC_{0-\infty}$ (mIU · h/mL) | $T_{max}$ (h) | $T_{1/2}$ (h) |
|---|---|---|---|---|---|---|
| UFSH IV | 15 | 2258 | 5093 | 5373 | 0.1 | 6.8 |
| UFSH SC | 15 | 152 | 2767 | 4566 | 6.0 | 16.4 |
| FSH variant IV | 15 | 3833 | 5318 | 5472 | 0.1 | 6.3 |
| FSH variant SC | 15 | 173 | 2598 | 3575 | 6.0 | 11.5 |

Abbreviations: ng, nanograms; h, hour; mL, milliliter; μg, microgram; kg, kilogram; $C_{max}$, maximum concentration; $AUC_{0-t}$, Area under the curve extrapolated from time 0 to 24 h; $AUC_{0-\infty}$, Area under the curve extrapolated from time 0 to infinity; $T_{max}$, time to maximum serum concentration; $T_{1/2}$, terminal elimination half-life.

Serum concentration time profiles demonstrate similar profiles for SC and IV administration for the FSH variant and uFSH. AUC, terminal half life, and Tmax were also similar.

Example 17

Pharmacokinetics of Subcutaneous (SC) Delivery of uFSH Compared to Pulmonary (P) and Subcutaneous (SC) FSH Variant in Cynomolgus Monkeys The following studies were undertaken to measure the bioavailability and pharmacokinetics of subcutaneous and pulmonary administration of a hFSH variant relative to subcutaneous administration of uFSH in Cynomolgus monkeys. Protocol 1 (Subcutaneous uFSH). Cynomolgus monkeys were administered uFSH (2 μg/kg) by the SC route. The solution contained uFSH, PBS, and 0.1% human serum albumin. Whole blood samples were collected at 0.08, 0.25, 0.5, 1, 3, 6, 9, 12, 24, 48, and 72 hrs post-dose. Samples were collected from the femoral vein or artery and placed in collection tubes without anticoagulants. The serum from the whole blood samples was obtained by centrifugation. Serum concentrations of immunoreactive uFSH were determined by a modified immunoradiometric assay employing a modified commercial FSH kit, FSH IRMA, DPC® Ltd. (Los Angeles, Calif.). IRMA binding data were analyzed by using a validated data reduction software that employs a 4 or 5 parameter logistic algorithm (StatLIA®, Brendan Scientific Corporation). Serum concentrations of immunoreactive uFSH were estimated from a standard curve with uFSH for monkeys administered uFSH. The standards were prepared in cynomolgus monkey serum with concentrations ranging from 0.5 ng/mL–75 ng/mL. The lower limit of quantitation was 0.5 ng/mL. The upper limit of quantitation was 75 ng/mL. A pharmacokinetic analysis of the serum concentration data was conducted using conventional techniques. Means and SEM were sometimes calculated using Microsoft Excel.

Protocol 2 (Subcutaneous and Pulmonary rFSH variant). Cynomolgus Monkeys were administered a recombinantly produced hFSH variant (2 μg/kg) by SC and by pulmonary routes. The recombinant host was designed to express the alpha subunit of SEQ ID NO:5 and the beta subunit of SEQ ID NO:11 and active variant was purified from the fermentation broth. The powder formulation was comprised of FSP, leucine, and sodium citrate in weight ratio of 12.5:80:7.5. Pulmonary delivery was carried out using an Inhale dry powder inhalation device (as described in Example 10 above) to disperse powder from blister packs into the monkey head dome for a 2-minute exposure, as described by Allen, D. L., et al., *J. Appl. Toxicol,* 15(1):13–17 (1995). Serum levels of rFSH variant were then measured after the 2-minute exposure. The inhaled doses each monkey received were calculated post-treatment based on the aerosol concentration and the mean minute volume of each monkey during the 2 minutes of inhalation. These calculated pulmonary doses vary between monkeys (see Table 26). A subcutaneous administration of rFSH variant was also administered to obtain relative pulmonary bioavailability following calculations of pharmacokinetic parameters. The formulation for subcutaneous administration contained FSP, PBS, and 0.1% human serum albumin.

Whole blood samples were collected at 0.08, 0.25, 0.5, 1, 3, 6, 9, 12, 24, 48, and 72 hrs post-dose. Samples were collected from the femoral vein or artery and placed in collection tubes without anticoagulants. The serum from the whole blood samples was obtained by centrifugation. Serum concentrations of immunoreactive rFSH variant were determined by a modified immunoradiometric assay employing a modified commercial FSH kit, FSH IRMA, DPC® Ltd. (Los Angeles, Calif.). IRMA binding data were analyzed by using a valid data reduction software that employs a 4 or 5 parameter logistic algorithm (StatLIA®, Brendan Scientific Corporation). Serum concentrations of immunoreactive rFSH variant were estimated from a standard curve with rFSH variant for monkeys administered rFSH variant. The standards were prepared in cynomolgus monkey serum with concentrations ranging from 0.5 ng/mL-75 ng/mL. The lower limit of quantitation was 0.5 ng/mL. The upper limit of quantitation was 75 ng/mL.

The purpose of this study was to measure the percent bioavailability of an exemplary dry powder formulation (leucine/citrate) of a hFSH variant in cynomolgus monkeys following pulmonary administration, relative to the subcutaneous administration of FSH. In this study, each monkey received one pulmonary administration of rFSH variant and two separate subcutaneous injections [2 μg/kg of hFSH variant and uFSH]. The subcutaneous injection of uFSH was administered to compare to the rFSH variant. Blood samples were obtained at 0, 0.08, 0.25, 0.5, 1, 3, 6, 9, 12, 24, 48, and 72 hours following pulmonary administration. Blood samples for subcutaneous administration were taken at 0, 1, 3, 6, 9, 12, 24, 48, and 72 hours. A modified commercial IRMA kit was used to determine the serum concentrations of immunoreactive hFSH variant or uFSH. These concentrations are found in Tables 26 through 29.

The average percent bioavailability of hFSH variant in the exemplary pulmonary formulation (leucine/citrate) was approximately 4.6% relative to subcutaneous administration based on inhaled doses. The corresponding in-lung bioavailability, or relative pulmonary bioavailability, in this study with hFSH variant is estimated to be about 18.4% based on the measurements of pulmonary deposition of 2 μm MMAD particles in monkeys using gamma scintography. In a monkey study with uFSH in a mannitol/citrate formulation, the average relative bioavailability was 6.5% based on inhaled dose (26% relative pulmonary bioavailability). Pulmonary administration of rFSH variant produced peak concentrations of immunoreactive rFSH variant at an average of 10.8 hours compared to 5.4 hours following subcutaneous administration. Pulmonary delivery of uFSH in a mannitol/citrate formulation also reached peak serum concentrations at approximately 10 hours.

The pharmacokinetic parameters of hFSH variant following pulmonary and subcutaneous administration were similar (Tables 26, 27). The pharmacokinetic parameters for the two molecules (uFSH and hFSH variant) following subcutaneous administration were similar (Table 29). These parameters were also comparable to those found in the Example 10 herein following subcutaneous administration of 2 μg/kg of uFSH.

TABLE 26

Serum Concentrations (ng/mL) of Immunoreactive rFSH variant in Cynomolgus Monkeys Following Pulmonary Administration of rFSH variant.

| | Pulmonary rFSH variant Animal Number (sex) | | | | | | | |
|---|---|---|---|---|---|---|---|---|
| Time (hr) | 8717 (M) | 8720 (M) | 8791 (F) | 8794 (F) | 8795 (F) | Mean | SEM | N |
| 0 | BQL | BQL | BQL | BQL | BQL | 0 | 0 | 5 |
| 0.08 | BQL | BQL | BQL | BQL | BQL | 0 | 0 | 5 |
| 0.25 | BQL | BQL | BQL | BQL | 0.89 | 0.18 | 0.18 | 5 |
| 0.5 | BQL | BQL | BQL | 0.55 | 1.29 | 0.37 | 0.25 | 5 |
| 1 | 0.80 | 1.04 | 0.96 | 1.28 | 2.20 | 1.26 | 0.25 | 5 |
| 3 | 4.94 | 4.58 | 3.07 | 4.14 | 5.68 | 4.48 | 0.43 | 5 |
| 6 | 7.78 | 7.09 | 5.73 | 6.30 | 6.30 | 6.64 | 0.36 | 5 |
| 9 | 10.08 | 6.77 | 6.34 | 4.37 | 7.92 | 7.10 | 0.94 | 5 |
| 12 | 10.88[1] | 7.74[1] | 7.25[1] | 5.73[1] | 14.44[1] | 9.21 | 1.55 | 5 |
| 24 | 5.90[1] | 4.00[1] | 5.41[1] | 3.80[1] | 5.81[1] | 4.98 | 0.45 | 5 |

TABLE 26-continued

Serum Concentrations (ng/mL) of Immunoreactive rFSH variant in Cynomolgus Monkeys Following Pulmonary Administration of rFSH variant.

| | Pulmonary rFSH variant Animal Number (sex) | | | | | | | |
|---|---|---|---|---|---|---|---|---|
| Time (hr) | 8717 (M) | 8720 (M) | 8791 (F) | 8794 (F) | 8795 (F) | Mean | SEM | N |
| 48 | 1.92[1] | 2.01[1] | 1.94[1] | 2.32[1] | 1.28[1] | 1.89 | 0.17 | 5 |
| 72 | 0.72[1] | 0.86[1] | 0.86[1] | 1.11[1] | 2.28[1] | 1.17 | 0.29 | 5 |

TABLE 27

Serum Concentrations (ng/mL) of Immunoreactive rFSH variant in Cynomolgus Monkeys Following Subcutaneous Administration of rFSH variant.

| | Subcutaneous rFSH variant (2 μg/kg) Animal Number (sex) | | | | | | | |
|---|---|---|---|---|---|---|---|---|
| Time (hr) | 8717 (M) | 8720 (M) | 8791 (F) | 8794 (F) | 8795 (F) | Mean | SEM | N |
| 0 | BQL | BQL | BQL | BQL | BQL | 0 | 0 | 5 |
| 1 | 0.53 | BQL | BQL | BQL | NR | 0.13 | 0.13 | 4 |
| 3 | 2.76 | 1.32 | 2.66 | 2.66 | 7.03 | 3.29 | 0.97 | 5 |
| 6 | 5.53 | 3.65 | 3.80 | 4.32 | 6.14 | 4.69 | 0.49 | 5 |
| 9 | 4.39 | 2.74 | 3.46 | 3.29 | 4.42 | 3.66 | 0.33 | 5 |
| 12 | 2.74[1] | 2.04[1] | 2.64[1] | 2.68[1] | 3.81[1] | 2.78 | 0.29 | 5 |
| 24 | 2.59[1] | 1.86[1] | 1.57[1] | 2.57[1] | 2.64[1] | 2.25 | 0.22 | 5 |
| 48 | 0.80[1] | 1.29[1] | 1.19[1] | 1.06[1] | 1.26[1] | 1.12 | 0.09 | 5 |
| 72 | BQL | 0.57 | 0.61 | BQL | BQL | 0.24 | 0.14 | 5 |

Abbreviations: M = male; F = female; BQL = below the quantitation limit; NR = no result due to insufficient amount of sample; hr = hour; ng = nanogram; mL = milliliter; μg = microgram; kg = kilogram.
[1] Time point used for calculating the half-life.

TABLE 28

Serum Concentrations (ng/mL) of Immunoreactive FSH in Cynomolgus Monkeys Following Subcutaneous Administration of uFSH

| | Subcutaneous uFSH (2 μg/kg) Animal Number (sex) | | | | | | | |
|---|---|---|---|---|---|---|---|---|
| Time (hr) | 8717 (M) | 8720 (M) | 8791 (F) | 8794 (F) | 8795 (F) | Mean | SEM | N |
| 0 | BQL | BQL | BQL | BQL | BQL | 0 | 0 | 5 |
| 1 | 0.77 | 0.67 | 0.73 | 2.93 | 1.23 | 1.27 | 0.43 | 5 |
| 3 | 5.05 | 4.38 | 3.57 | 6.71 | 3.55 | 4.65 | 0.59 | 5 |
| 6 | 6.31 | 4.52 | 4.76 | 6.53 | 3.60 | 5.14 | 0.56 | 5 |
| 9 | 6.30 | 4.28 | 4.14 | 4.85 | 3.55 | 4.62 | 0.47 | 5 |
| 12 | 4.46[1] | 4.04[1] | 4.11[1] | 3.39[1] | 2.81[1] | 3.76 | 0.29 | 5 |
| 24 | 2.61[1] | 2.87[1] | 2.83[1] | 3.06[1] | 2.85[1] | 2.84 | 0.07 | 5 |
| 48 | 1.15[1] | 1.10[1] | 1.65[1] | 1.04[1] | 1.65[1] | 1.32 | 0.14 | 5 |
| 72 | BQL | BQL | 0.86 | 0.61 | 0.70 | 0.43 | 0.18 | 5 |

Abbreviations: M = male; F = female; BQL = below the quantitation limit; hr = hour; ng = nanogram; mL = milliliter; μg = microgram; kg = kilogram.
[1] Time point used for calculating the half-life

TABLE 29

Pharmacokinetic Parameters for Cynomolgus Monkeys after Pulmonary and Subcutaneous Administration of rFSH variant and Subcutaneous Administration of uFSH

| | rFSH variant Subcutaneous Dose | | | | | | | |
|---|---|---|---|---|---|---|---|---|
| Statistics\Subject ID | 8717 | 8720 | 8791 | 8794 | 8795 | Mean | SEM | N |
| $AUC_{0-72hr}$ (ng*hr/mL) | 123.8 | 109.1 | 112.4 | 121.3 | 159.1 | 125.1 | 8.92 | 5 |
| $AUC_{0-\infty}$ (ng*hr/mL) | 130.9 | 144.5 | 132.1 | 139.3 | 174.3 | 144.2 | 7.92 | 5 |
| Half-Life (hr) | 19.09 | 52.95 | 33.61 | 25.34 | 22.54 | 27.05 | 4.26 | 5 |
| $C_{Max}$ (ng/mL) | 5.53 | 3.65 | 3.80 | 4.32 | 7.03 | 4.87 | 0.63 | 5 |
| $T_{Max}$ (hr) | 6 | 6 | 6 | 6 | 3 | 5.40 | 0.60 | 5 |
| Dose (μg/kg) | 2 | 2 | 2 | 2 | 2 | 2 | | |
| | rFSH variant Pulmonary Dose | | | | | | | |
| Statistics\Subject ID | 8717 | 8720 | 8791 | 8794 | 8795 | Mean | SEM | N |
| $AUC_{0-72hr}$ (ng*hr/mL) | 309.5 | 242.9 | 253.7 | 224.5 | 331.2 | 272.4 | 20.42 | 5 |
| $AUC_{0-\infty}$ (ng*hr/mL) | 324.3 | 268.5 | 282.6 | 297.5 | 337.9 | 302.1 | 12.84 | 5 |
| Half-Life (hr) | 15.33 | 19.70 | 18.92 | 26.22 | 21.32 | 19.69 | 1.71 | 5 |
| $C_{Max}$ (ng/mL) | 10.88 | 7.74 | 7.25 | 6.30 | 14.44 | 9.32 | 1.49 | 5 |
| $T_{Max}$ (hr) | 12 | 12 | 12 | 6 | 12 | 10.8 | 1.20 | 5 |
| Ave. Minute Vol. (L) | 2.45 | 2.07 | 3.57 | 3.08 | 2.36 | | | |
| Dose (μg/kg) | 69 | 85 | 124 | 114 | 87 | 95.8 | 10.1 | 5 |
| Percent Bioavailability | 7.18 | 4.37 | 3.45 | 3.75 | 4.50 | 4.64 | 0.66 | 5 |
| | uFSH Subcutaneous Dose | | | | | | | |
| Statistics\Subject ID | 8717 | 8720 | 8791 | 8794 | 8795 | Mean | SEM | N |
| $AUC_{0-72hr}$ (ng*hr/mL) | 159.6 | 146.7 | 168.4 | 168.1 | 152.6 | 159.1 | 4.27 | 5 |
| $AUC_{0-\infty}$ (ng*hr/mL) | 169.3 | 161.6 | 204.3 | 178.4 | 215.1 | 185.7 | 10.3 | 5 |
| Half-Life (hr) | 18.66 | 18.90 | 27.79 | 20.06 | 43.51 | 23.22 | 3.21 | 5 |
| $C_{Max}$ (ng/mL) | 6.31 | 4.52 | 4.76 | 6.71 | 3.60 | 5.18 | 0.58 | 5 |
| $T_{Max}$ (hr) | 6 | 6 | 6 | 3 | 6 | 5.40 | 0.60 | 5 |
| Dose (μg/kg) | 2 | 2 | 2 | 2 | 2 | 2 | | 5 |

Abbreviations: hr = hour; mL = milliliter; SEM = standard error of the mean; ng = nanogram; μg = microgram; kg = kilogram; N = number of observations; $C_{max}$ = maximum concentration; $AUC_{0-t}$ = Area under the curve extrapolated from time 0 to tau (72 hr); $AUC_{0-\infty}$ = Area under the curve extrapolated from time 0 to infinity; $T_{max}$ = time to maximum serum concentration.

Example 18

Expression of hFSH Variant in CHO-K1 Cells

One skilled in the art will be aware of many ways to express FSP using suitable expression vectors and host cell lines. One way is to use a Chinese Hamster Ovary cell line, such as the CHO-K1 cell line (LONZA Biologics). These cells may be designed to express hFSH variant comprised of the alpha subunit having the sequence of SEQ ID NO: 5 and the beta subunit having the sequence of SEQ ID NO: 11.

An expression vector is constructed by standard techniques. Vector DNA to support the transfection may be prepared in Gibco/BRL ElectroMax DH10B cells (Cat. # 18290-015), using the Qiagen QiaFilter Maxi Prep kit (Cat. # 12263) and the vector confirmed by an appropriate diagnostic digest (e.g., Hind III/Xho I). Sequence analysis of both genes would confirm that the DNA sequences designed to express the alpha subunit of SEQ ID NO:5 and the variant beta subunit of SEQ ID NO:11 are those given in SEQ ID NOS:37 and 38 herein, respectively. The expression of each subunit can be controlled by a different promoter or by the same promoter. The sequences may also use a polyA tail. The vector may contain a selectable marker. The vector is used to transfect CHO-K1 cells using known techniques.

The cell line is grown in suitable medium, such as GibcoBRL's CD CHO media, under selective pressure. ELISA assays may be used to identify master wells expressing hFSH variant, which are cloned and amplified using standard procedures. These procedures will lead to clones that have suitable expression levels. For example, in shake flasks (20–60 mL), active hFSH variant at 30 mg/L is produced after 7 to 8 days.

Example 19

Purification of FSP

Purification of recombinant FSP, such as for example, the hFSH variant comprised of an alpha subunit of SEQ ID NO: 5 and a beta subunit of SEQ ID:11, can be accomplished by a number of methods described and known in the art from monolayer or suspension cultures of transformed host cells, such as CHO-K1 or AV12 cell lines or other production lines suitably available. One method for isolating FSP from the culture medium comprises subjecting the culture medium to cation or anion exchange chromatography, dye affinity chromatography, reverse phase chromatography, gel filtration chromatography, or to some combination of these methods. In the case of suspension cultures, which may contain detergents, additional purification steps may be needed, such as a ion exchange step. The chromatographic steps can be optimized for pH, conductivity, buffer composition and running conditions (column dimensions, flow rates, etc). Purity and yield can be analyzed by SDS-PAGE gels (both Coomassie staining and Western blotting), ELISA assays, exclusion chromatography and protein concentration by UV absorbance at 277 nm or other known techniques. Using standard purification steps, FSP having purity greater than 95% by Coomassie and silver-stained gels can be obtained.

Example 20

Subchronic Inhalation Study of Leucine as an Excipient for Pulmonary Administration The pharmaceutical acceptability of leucine in a powder for pulmonary delivery of FSP was studied in domestic-reared cynomolgus monkeys (*Macaca fascicularis*). The target inhaled dose of leucine:sodium citrate (90:10) was 1.66 mg/kg/day. The animals were exposed for 15 minutes per day, for 15 days. The monkeys were obtained from Charles River BRF, Inc—Mauritius. Monkeys were housed upon arrival and isolated for at least 6 weeks prior to being assigned to the study. Four monkeys (two of each sex) were arbitrarily assigned to treatment groups and were assigned to individual cages. Monkeys were housed in a room in which the thermostats were set to maintain a temperature of 72±8° F. The environmental control system was designed to maintain a minimum relative humidity of 20% and a maximum of 80%. The photo period was 12 hours light and 12 hours dark, changing at 0600 and 1800 hours. Monkeys were individually housed in aluminum cages with suspended floors. Feces and urine were manually washed away daily. Approximately 10 to 20 biscuits of Certified Primate Chow 5048 (PMI Nutrition International, Inc) were offered to the monkeys twice daily during the week, and a double ration was offered once daily on weekends. Each monkey received fresh fruit at least 3 times each week. City water was available ad libitum from an automatic watering system except during exposures. Each monkey was conditioned to sit in a restraint chair at least 9 times prior to beginning the exposures. The conditioning was accomplished with the use of food treats as positive reinforcement.

The monkeys were placed into restraint chairs prior to each exposure. Two sheets of latex (0.30 in. thick) were placed around the animals' necks to form a seal. An approximately 7.7-liter head-dome was placed over the animals' heads. Airflow of approximately 12 L/min was maintained through the head-dome via a calibrated transvector on the exhaust port. The leucine-citrate powder (90% leucine/10% sodium citrate) was generated using a Wright Dust Feed generator. Eight to ten liters/minute of air were run through the generator. The aerosol was passed through a cyclone then entered the head-dome for the monkey to breathe.

The concentration of leucine was determined with gravimetric samples taken from the head dome during exposure. These samples were collected by drawing 1 LPM of air through a 25-mm Gelman Type A/E glass fiber filter that was connected to the head dome. One particle size determination was completed. The particle size was determined from samples collected using a Sierra Model 218K Cascade Impactor fitted with Gelman Type A/E glass fiber filters. Airflow though the Cascade Impactor was 3 LPM for a duration of 5 minutes. Inhaled doses were calculated as follows: (average minute volume×exposure time)×(average gravimetric concentration)÷body weight.

Flow-derived parameters (tidal volume, minute volume, and breathing frequency) were monitored using a size '0' pneumotachograph connected to a port on the head-dome. The signals were collected on a personal computer using the XA software from Buxco Electronics, Inc. At least 15 minutes of pre-exposure data were collected before the exposures began, followed by data collection throughout the exposure period. All pulmonary function data were collected as 5-minute averages. These data were downloaded into a Microsoft Excel spreadsheet and graphed to look for trends in breathing patterns.

Each monkey was observed prior to, during, and after exposures. Any unusual behavior was noted. Body weights were recorded (initial body mass—males: 2.9 to 4.1 kg; females: 2.7 to 2.8 kg). These data were averaged and used to calculate the dose of leucine delivered to the monkeys' lungs. Blood samples were obtained from each monkey prior to initiation of dosing and on Day 15. These blood samples were obtained prior to feeding. In addition, bronchoalveolar lavage (BAL) was performed prior to initiation of dosing and on Day 15. The animals were dosed with glycopyrrolate 0.015 mg/kg IM, followed a few minutes later with ketamine HCl 10 mg/kg IM. A pediatric bronchoscope was then inserted into the right or left lower lobe and wedged into an airway. Two 10-mL aliquots of normal saline were put into the lung then gently hand-suctioned out with a 20-mL syringe. The recovered fluid was put on ice and sent to the clinical pathology laboratory for analysis.

Blood analyses included: erythrocyte count, hemoglobin, hematocrit (packed cell volume), mean corpuscular volume, mean corpuscular hemoglobin, mean corpuscular hemoglobin concentration, reticulocyte count, blood cell morphology, total leukocyte count, leukocyte differential, platelet (thrombocyte) count, total leukocyte count, leukocyte differential, prothrombin time, activated partial thromboplastin time, glucose, blood urea nitrogen, creatinine, total bilirubin, alkaline phosphatase, alanine transaminase, aspartate transaminase, gamma glutamyltransferase, creatine phosphokinase, calcium, inorganic phosphorus, sodium, potassium, chloride, cholesterol, triglycerides, total protein, albumin, globulin, microprotein. Urine was analyzed for specific gravity and protein.

The average gravimetric concentration across the 14 days of exposure was 425.83±232.90 μg/L (Mean±SD). The mass median equivalent aerodynamic diameter was 1.00 μm with a geometric standard deviation of 2.46. The average inhaled dose relative to body weight was 2.13±0.56 mg/kg/day.

There were no unusual behaviors noted in any animal during the study. There were no treatment-related increases in breathing frequency, tidal volume, or minute volume. An apparent increase in breathing frequency on the first day of exposure is most likely due to a non-specific response of the monkeys to the appearance of the dust cloud in the dome. By the next measurement day, the animals had acclimated to the dust in the dome and the difference in breathing frequency disappeared.

There were no compound-related effects on hematology parameters, clinical chemistry parameters, urinalysis parameters, or on bronchoalveolar lavage (BAL) parameters. One monkey had minimal elevation in protein level, total white blood cell count, neutrophil, lymphocyte and macrophage counts, and red blood cell count in the BAL fluid compared to other monkeys in the study and to historical reference values. These findings were considered unrelated to the compound and likely reflect a mild, undetermined, preexisting pulmonary condition in this monkey as evidenced by an elevated BAL fluid protein level in the pretreatment BAL.

Example 21

FSP Powders Made Using a Niro Spray Dryer

Powders containing leucine, sodium citrate, and recombinant FSP biosynthesized and purified essentially as described herein were prepared using a Niro mobile minor spray dryer fitted with a two-filled nozzle. Powder characteristics were measured as described elsewhere herein. Free subunit composition was measured essentially as described in Example 2. The composition of each of the FSP powders is provided in Table 30 below. Batch sizes were ten grams for the first six lots, and 5 grams for the last three lots in Table 30. Yields for the powders ranged from 62%–78%.

TABLE 30

| Niro FSP Powder Characteristics | | | | | | | | |
|---|---|---|---|---|---|---|---|---|
| | Powder Composition | | | MMD | MMAD | | $H_2O$ | ED |
| Lot # | FSP | L | C | (μm) | (μm) | Sub. | (%) | (%) |
| 2011 | 1.9 | 60 | 38 | 2.3 | 3.5 | 8.2 | 1.4 | |
| 2012 | 1.9 | 60 | 38 | 2.2 | 3.6 | 6.6 | 0.8 | |
| 2013 | 1.9 | 60 | 38 | 2.1 | 3.5 | 7.9 | 1.3 | |
| 2014 | 1.9 | 60 | 38 | 2.6 | 3.8 | 7.7 | 1.2 | |
| 2015 | 1.9 | 60 | 38 | 2.0 | 3.4 | 6.1 | 1.2 | |
| 2016 | 1.9 | 60 | 38 | 1.7 | 3.0 | 4.5 | 1.7 | |
| 2017 | 1.9 | 40 | 58 | 1.7 | 2.3 | 3.2 | | 82 |
| 2018 | 1.9 | 60 | 38 | 1.4 | 2.2 | 3.8 | | 77 |
| 2021 | 11 | 60 | 29 | 1.8 | 2.2 | 2.8 | | 78 |
| 2022 | 11 | 40 | 49 | 1.6 | 2.3 | 2.9 | | 82 |
| 2095 | 1.9 | 60 | 38 | 1.5 | 2.4 | 5.5 | | |
| 2096 | 1.9 | 40 | 58 | 1.5 | 2.1 | 4.0 | | |

FSP = follicle stimulating protein; L = leucine; C = sodium citrate; Sub. = subunit content

Example 22

Effects of Scale and Formulation Components on Characteristics of FSP Powders Lots 00023–00030 were produced using a Buchi spray dryer (Model 190) fitted with a modified two fluid nozzle. Analytical measurements were made after filling blister packs by hand. A hFSH variant (cell designed to express the alpha subunit having the sequence of SEQ ID NO:5 and the beta subunit having the sequence of SEQ ID NO: 11) was used for all lots. Lots 1952–1954 were produced using a Niro Mobile Minor spray dryer fitted with a modified two fluid nozzle.

TABLE 31

| Lot | FSP | L | C | Lot size (g) | [FSP] μg/mL | MMD (μm) | MMAD (μm) | APC (%) |
|---|---|---|---|---|---|---|---|---|
| 1952 | 1.75 | 40 | 58 | 5 | 170 | 1.9 | 2.2 | 56 |
| 1953 | 1.75 | 40 | 58 | 5 | 340 | 2.2 | 2.8 | 46 |
| 1954 | 8 | 80 | 12 | 3 | 800 | 1.8 | 3.6 | 39 |

TABLE 32

| | Powder Composition | | | ED (%) | | |
|---|---|---|---|---|---|---|
| Lot | FSP (%) | L (%) | C (%) | mean (SD) | Subunit (%) | HOA (%) |
| 00023 | 1.0 | 40 | 59.0 | 76.2 (8.5) | 6.5 | 0.16 |
| 00024 | 1.5 | 60 | 38.5 | 83.1 (4.0) | 5.6 | 0.18 |
| 00025 | 1.5 | 50 | 48.5 | | 4.8 | 0.24 |
| 00026 | 4.0 | 80 | 16.0 | 85.7 (2.5) | 5.4 | 0.12 |
| 00027 | 4.0 | 40 | 56.0 | 82.3 (5.0) | 3.6 | 0.07 |
| 00028 | 12.0 | 60 | 28.0 | | 3.3 | 0.03 |
| 00030 | 1.5 | 60 | 38.5 | 81.5 (3.2) | 5.6 | 0.08 |
| 1952 | 1.7 | 40 | 58.3 | 78.1 (6.6) | 4 | |
| 1953 | 1.7 | 40 | 58.3 | 75.6 (6.5) | 5 | |
| 1954 | 8.0 | 80 | 12.0 | 76.9 (3.5) | 9 | |

L = leucine; C = sodium citrate

Example 23

Effect of Various Amino Acid Excipients on FSP Powder Characteristics

FSP powders containing various amino acid excipients, optionally in combination with citrate, prepared essentially as described herein, with yields ranging from about 54% to 78%. Selected features of the resultant powders are provided in Table 33 below.

TABLE 33

| Lot | Powder Composition (%) | $H_2O$ (%) | Subunit (%) | HOA (%) | MMD (μm) |
|---|---|---|---|---|---|
| 000047 | FSP:alanine:citrate 2:80:18 | 1.3 | 36.4 | 0.18 | 1.32 |
| 000048 | FSP:leucine:citrate:methionine 2:80:13:5 | 0.6 | 33.1 | 0.05 | 1.89 |
| 000049 | FSP:leucine:citrate 2:80:18 | 0.6 | 15.1 | 0.12 | 1.72 |
| 000050 | FSP:leucine:citrate:mannitol 2:80:13:5 | 0.3 | 15.4 | 0.08 | 1.76 |
| 000051 | FSP:tri-leucine:citrate 2:40:58 | 2.3 | 4.5 | 0.03 | 1.43 |
| 000052 | FSP:leucine:citrate:isoleucine 2:80:13:5 | 0.5 | 11.1 | 0.05 | 1.78 |
| 000053 | FSP:leucine:citrate:arginine 2:80:13:5 | 0.7 | 6.9 | 0.05 | 1.40 |
| 00029 | FSP:valine:citrate 1.5:60:38:5 | — | 13.6 | 0.30 | — |

We claim:

1. A stabilized dry powder composition for delivery to the deep lung of a mammalian subject, comprising:

(i) a pharmacologically effective amount of follicle-stimulating hormone (FSH), FSH glycoform, or mixture thereof, wherein the FSH, FSH glycoform, or mixture thereof is selected from the group consisting of mammalian urinary-derived FSH, FSH glycoform, or mixture thereof and recombinantly derived FSH, FSH glycoform, or mixture thereof; and (ii) a pharmaceutically acceptable excipient, wherein the composition comprises particles having a bulk density from 0.1 to 10 grams per cubic centimeter, wherein the composition possesses a specific activity of at least 50 IU/mg FSH, wherein the composition comprises a solid state matrix that imparts a stabilizing environment for the FSH, FSH glycoform, or mixture thereof, wherein the solid state matrix is crystalline, an amorphous glass, or a mixture thereof, and wherein the composition maintains at least about 70% of its initial bioactivity when stored for one month at room temperature under ambient conditions.

2. The composition of claim 1, characterized by a relative pulmonary bioavailability between 1% to 60%.

3. The composition of claim 1, characterized by a relative pulmonary bioavailability between 1% and 30%.

4. The composition of claim 1, characterized by a relative pulmonary bioavailability between 1% and 20%.

5. The composition of claim 1, having a residual moisture content of less than about 10 percent by weight.

6. The composition of claim 1, wherein the specific bioactivity of FSH, FSH glycoform, or mixture thereof is greater than 100 IU per gram of powder.

7. The composition of claim 1, wherein the specific bioactivity of FSH, FSH glycoform, or mixture thereof is greater than 1,000 IU per gram of powder.

8. The composition of claim 1, wherein the specific bioactivity of FSH, FSH glycoform or mixture thereof is greater than 5,000 IU per gram of powder.

9. The composition of claim 1, wherein the specific bioactivity of FSH, FSH glycoform, or mixture thereof is greater than 25,000 IU per gram of powder.

10. The composition of claim 1, characterized by a distribution phase half-life between 1 and 50 hours when administered via inhalation to the lung or deep lung.

11. The composition of claim 1, wherein said FSH, FSH glycoform, or mixture thereof is recombinantly derived.

12. The composition of claim 11, wherein said recombinantly derived FSH, FSH glycoform, or mixture thereof is FSH, FSH glycoform, or mixture thereof comprising a heterodimer containing an alpha subunit and a beta subunit.

13. The composition of claim 12, wherein said heterodimer is free from contamination of beta subunits of SEQ ID NO:8.

14. The composition of claim 12, wherein said heterodimer comprises a beta subunit selected from the group consisting of SEQ ID NOS: 11, 12, 13, 14, 15, 16, 17, 18, 19, 20, 21, 22, 23, 24, 25, 26, 27, and 28.

15. The composition of claim 12, wherein said heterodimer comprises an alpha subunit selected from the group consisting of SEQ ID NOS.: 29, 30, and 31.

16. The composition of claim 12, comprising two or more different hFSH, hFSH glycoform, or mixture thereof polypeptides or heterodimers.

17. The composition of claim 1, wherein said FSH, FSH glycoform, or mixture thereof is human urinary-derived FSH.

18. The composition of claim 1, wherein said composition comprises particles having a mass median diameter (MMD) from about 0.1 to 20 microns.

19. The composition of claim 1, wherein said composition comprises particles having a mass median diameter (MMD) from about 0.1 to 10 microns.

20. The composition of claim 1, wherein said composition comprises particles having a mass median diameter (MMD) from about 0.5 to 7 microns.

21. The composition of claim 1, wherein said composition comprises particles having a mass median aerodynamic diameter (MMAD) less than about 10 microns.

22. The composition of claim 21, wherein said composition comprises particles having a mass median aerodynamic diameter (MMAD) from about 1.5 to about 3.5 microns.

23. The composition of claim 1, comprising particles having a bulk density from 0.15 to 4.0 grams per cubic centimeter.

24. The composition of claim 1, comprising particles having a bulk density from 0.17 to 0.75 grams per cubic centimeter.

25. The composition of claim 1, wherein said composition contains from about 0.1 to 99.9 percent by weight FSH, FSH glycoform, or mixture thereof.

26. The composition of claim 1, having an emitted dose greater than 30%.

27. The composition of claim 26, having an emitted dose greater than 50%.

28. The composition of claim 1, having an emitted dose greater than 55%.

29. The composition of claim 1, having an emitted dose greater than 60%.

30. A spray dried composition of claim 1.

31. The composition of claim 1, further comprising a buffer salt.

32. The composition of claim 31, which upon dissolution in water exhibits a pH between about 4 and 10.

33. The composition of claim 1, wherein said excipient is a carbohydrate.

34. The composition of claim 33, wherein said carbohydrate excipient is selected from the group consisting of mannitol, trehalose, and raffinose.

35. The composition of claim 1, wherein said excipient is selected from the group consisting of amino acids, polyamino acids, polypeptides, and proteins.

36. The composition of claim 35, wherein said excipient is an amino acid selected from the group consisting of leucine, isoleucine, and norleucine.

37. The composition of claim 36, wherein said excipient is leucine.

38. The composition of claim 37, comprising 20%–80% (w/w) leucine.

39. The composition of claim 38, comprising 40–60% (w/w) leucine.

40. The composition of claim 1, comprising FSH, FSH glycoform, or mixture thereof, mannitol and citrate.

41. The composition of claim 1, comprising FSH, FSH glycoform, or mixture thereof, leucine and citrate.

42. A method of preparing a stabilized dry powder FSH, FSH glycoform, or mixture thereof composition of claim 1, comprising:

(i) mixing the FSH, FSH glycoform, or mixture thereof and the excipient with a solvent to form a solution or a suspension, and (ii) drying the solution or suspension under conditions suitable to form a respirable, bioactive FSH, FSH, glycoform, or mixture thereof dry powder of claim 1.

43. The method of claim 42, where said drying comprises spray drying.

44. The method of claim 42, wherein said FSH, FSH glycoform, or mixture thereof is mixed in a solvent containing said excipient material to form a solution having a pH from about 4 to 10.

45. The method of claim 42, wherein the amount of FSH, FSH glycoform, or mixture thereof in said solvent comprises from about 0,01 to 10% of the total solids content of the solution or suspension.

46. The method of claim 42, wherein said solvent is water or an alcohol.

47. The method of claim 42, wherein the degree of sialylation of FSH, FSH glycoform, or mixture thereof in the dried powder is at least about 30% of the degree of sialylation of FSH, FSH glycoform or mixture thereof prior to said drying.

48. A method for delivery of FSH, FSH glycoform, or mixture thereof to the lungs of a mammalian patient, said method comprising administering by inhalation the dry powder composition of claim 1 in aerosolized form.

49. A method for delivering FSH, FSH glycoform or mixture thereof to a mammalian subject, comprising:

(i) aerosolizing the FSH, FSH glycoform, or mixture thereof dry powder composition of claim 1, and (ii) administering said aerosolized FSH, FSH glycoform, or mixture thereof dry powder composition by inhalation for deposition in and absorption from the lung of said subject.

50. The composition of claim 1, wherein absorption enhancer is not present in the composition.

51. The composition of claim 1, wherein the composition possesses a specific activity up to 13,500 IU/mg FSH.

52. The composition of claim 51, characterized by a relative pulmonary bioavailability between 1% to 60%.

53. The composition of claim 51, having a residual moisture content of less than about 10 percent by weight.

54. The composition of claim 51, wherein the specific bioactivity of FSH, FSH glycoform, or mixture thereof is greater than 100 IU per gram of powder.

55. The composition of claim 51, characterized by a distribution phase half-life between 1 and 50 hours when administered via inhalation to the lung or deep lung.

56. The composition of claim 51, wherein said composition comprises particles having a mass median diameter (MMAD) from about 0.1 to 20 microns.

57. The composition of claim 51, wherein said composition comprises particles having a mass median aerodynamic diameter (MMAD) less than about 10 microns.

58. The composition of claim 51, wherein said composition contains from about 0.1 to 99.9 percent by weight FSH, FSH glycoform, or mixture thereof.

59. The composition of claim 51, having an emitted dose greater than 30%.

60. A spray-dried composition of claim 51.

61. The composition of claim 51, further comprising a buffer salt.

62. The composition of claim 51, wherein said excipient is a carbohydrate.

63. The composition of claim 51, wherein said excipient is selected from the group consisting of amino acids, polyamino acids, polypeptides, and proteins.

64. The composition of claim 51, comprising FSH, FSH glycoform, or mixture thereof, mannitol and citrate.

65. The composition of claim 51, comprising FSH, FSH glycoform, or mixture thereof, leucine and citrate.

66. A method of preparing a stabilized dry powder FSH, FSH glycoform, or mixture thereof composition of claim 51, comprising:

(i) mixing the FSH, FSH glycoform, or mixture thereof and the excipient with a solvent to form a solution or a suspension, and (ii) drying the solution or suspension under conditions suitable to form a respirable, bioactive FSH, FSH glycoform, or mixture thereof dry powder of claim 51.

67. A method for delivery of FSH, FSH glycoform, or mixture thereof to the lungs of a mammalian patient, said method comprising administering by inhalation the dry powder composition of claim 51 in aerosolized form.

68. A method for delivering FSH, FSH glycoform, or mixture thereof to a mammalian subject, comprising:

(i) aerosolizing the FSH, FSH glycoform, or mixture thereof dry powder composition of claim 51, and (ii) administering said aerosolized FSH, FSH glycoform, or mixture thereof dry powder composition by inhalation for deposition in and absorption from the lung of said subject.

* * * * *

SEQUENCE LISTING

<160> NUMBER OF SEQ ID NOS: 56

<210> SEQ ID NO 1
<211> LENGTH: 96
<212> TYPE: PRT
<213> ORGANISM: mammalian

<400> SEQUENCE: 1

Phe Pro Asp Gly Glu Phe Thr Met Gln Gly Cys Pro Glu Cys Lys Leu
1 5 10 15

Lys Glu Asn Lys Tyr Phe Ser Lys Pro Asp Ala Pro Ile Tyr Gln Cys
20 25 30

Met Gly Cys Cys Phe Ser Arg Ala Tyr Pro Thr Pro Ala Arg Ser Lys
35 40 45

Lys Thr Met Leu Val Pro Lys Asn Ile Thr Ser Glu Ala Thr Cys Cys
50 55 60

Val Ala Lys Ala Phe Thr Lys Ala Thr Val Met Gly Asn Val Arg Val
65 70 75 80

Glu Asn His Thr Glu Cys His Cys Ser Thr Cys Tyr Tyr His Lys Ser
85 90 95

<210> SEQ ID NO 2
<211> LENGTH: 111
<212> TYPE: PRT
<213> ORGANISM: mammalian

<400> SEQUENCE: 2

Arg Ser Cys Glu Leu Thr Asn Ile Thr Ile Thr Val Glu Lys Glu Glu
1 5 10 15

Cys Gly Phe Cys Ile Ser Ile Asn Thr Thr Trp Cys Ala Gly Tyr Cys
20 25 30

Tyr Thr Arg Asp Leu Val Tyr Arg Asp Pro Ala Arg Pro Asn Ile Gln
35 40 45

Lys Thr Cys Thr Phe Lys Glu Leu Val Tyr Glu Thr Val Lys Val Pro
50 55 60

Gly Cys Ala His His Ala Asp Ser Leu Tyr Thr Tyr Pro Val Ala Thr
65 70 75 80

Glu Cys His Cys Ser Lys Cys Asp Ser Asp Ser Thr Asp Cys Thr Val
85 90 95

Arg Gly Leu Gly Pro Ser Tyr Cys Ser Phe Arg Glu Ile Lys Glu
100 105 110

<210> SEQ ID NO 3
<211> LENGTH: 96
<212> TYPE: PRT
<213> ORGANISM: mammalian

<400> SEQUENCE: 3

Phe Pro Asp Gly Glu Phe Thr Thr Gln Asp Cys Pro Glu Cys Lys Leu
1 5 10 15

Arg Glu Asn Lys Tyr Phe Phe Lys Leu Gly Val Pro Ile Tyr Gln Cys
20 25 30

Lys Gly Cys Cys Phe Ser Arg Ala Tyr Pro Thr Pro Ala Arg Ser Arg
35 40 45

Lys Thr Met Leu Val Pro Lys Asn Ile Thr Ser Glu Ser Thr Cys Cys
50 55 60

-continued

```
Val Ala Lys Ala Phe Ile Arg Val Thr Val Met Gly Asn Ile Lys Leu
 65                  70                  75                  80

Glu Asn His Thr Gln Cys Tyr Cys Ser Thr Cys Tyr His His Lys Ile
                 85                  90                  95


<210> SEQ ID NO 4
<211> LENGTH: 111
<212> TYPE: PRT
<213> ORGANISM: mammalian

<400> SEQUENCE: 4

Asn Ser Cys Glu Leu Thr Asn Ile Thr Ile Ala Val Glu Lys Glu Gly
  1               5                  10                  15

Cys Gly Phe Cys Ile Thr Ile Asn Thr Thr Trp Cys Ala Gly Tyr Cys
             20                  25                  30

Tyr Thr Arg Asp Leu Val Tyr Lys Asp Pro Ala Arg Pro Asn Ile Gln
         35                  40                  45

Lys Thr Cys Thr Phe Lys Glu Leu Val Tyr Glu Thr Val Lys Val Pro
     50                  55                  60

Gly Cys Ala His His Ala Asp Ser Leu Tyr Thr Tyr Pro Val Ala Thr
 65                  70                  75                  80

Ala Cys His Cys Gly Lys Cys Asn Ser Asp Ser Thr Asp Cys Thr Val
                 85                  90                  95

Arg Gly Leu Gly Pro Ser Tyr Cys Ser Phe Gly Asp Met Lys Glu
            100                 105                 110


<210> SEQ ID NO 5
<211> LENGTH: 92
<212> TYPE: PRT
<213> ORGANISM: Homo sapiens

<400> SEQUENCE: 5

Ala Pro Asp Val Gln Asp Cys Pro Glu Cys Thr Leu Gln Glu Asn Pro
  1               5                  10                  15

Phe Phe Ser Gln Pro Gly Ala Pro Ile Leu Gln Cys Met Gly Cys Cys
             20                  25                  30

Phe Ser Arg Ala Tyr Pro Thr Pro Leu Arg Ser Lys Lys Thr Met Leu
         35                  40                  45

Val Gln Lys Asn Val Thr Ser Glu Ser Thr Cys Cys Val Ala Lys Ser
     50                  55                  60

Tyr Asn Arg Val Thr Val Met Gly Gly Phe Lys Val Glu Asn His Thr
 65                  70                  75                  80

Ala Cys His Cys Ser Thr Cys Tyr Tyr His Lys Ser
                 85                  90


<210> SEQ ID NO 6
<211> LENGTH: 111
<212> TYPE: PRT
<213> ORGANISM: Homo sapiens

<400> SEQUENCE: 6

Asn Ser Cys Glu Leu Thr Asn Ile Thr Ile Ala Ile Glu Lys Glu Glu
  1               5                  10                  15

Cys Arg Phe Cys Ile Ser Ile Asn Thr Thr Trp Cys Ala Gly Tyr Cys
             20                  25                  30

Tyr Thr Arg Asp Leu Val Tyr Lys Asp Pro Ala Arg Pro Lys Ile Gln
         35                  40                  45

Lys Thr Cys Thr Phe Lys Glu Leu Val Tyr Glu Thr Val Arg Val Pro
```

-continued

```
     50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly Glu Met Lys Glu
            100                 105                 110


<210> SEQ ID NO 7
<211> LENGTH: 96
<212> TYPE: PRT
<213> ORGANISM: mammalian

<400> SEQUENCE: 7

Phe Pro Asp Gly Glu Phe Thr Met Gln Gly Cys Pro Glu Cys Lys Leu
  1               5                  10                  15

Lys Glu Asn Lys Tyr Phe Ser Lys Leu Gly Ala Pro Ile Tyr Gln Cys
             20                  25                  30

Met Gly Cys Cys Phe Ser Arg Ala Tyr Pro Thr Pro Ala Arg Ser Lys
         35                  40                  45

Lys Thr Met Leu Val Pro Lys Asn Ile Thr Ser Glu Ala Thr Cys Cys
     50                  55                  60

Val Ala Lys Ala Phe Thr Lys Ala Thr Val Met Gly Asn Ala Arg Val
 65                  70                  75                  80

Glu Asn His Thr Glu Cys His Cys Ser Thr Cys Tyr Tyr His Lys Ser
                 85                  90                  95


<210> SEQ ID NO 8
<211> LENGTH: 111
<212> TYPE: PRT
<213> ORGANISM: mammalian

<400> SEQUENCE: 8

Asn Ser Cys Glu Leu Thr Asn Ile Thr Ile Thr Val Glu Lys Glu Glu
  1               5                  10                  15

Cys Asn Phe Cys Ile Ser Ile Asn Thr Thr Trp Cys Ala Gly Tyr Cys
             20                  25                  30

Tyr Thr Arg Asp Leu Val Tyr Lys Asp Pro Ala Arg Pro Asn Ile Gln
         35                  40                  45

Lys Thr Cys Thr Phe Lys Glu Leu Val Tyr Glu Thr Val Lys Val Pro
     50                  55                  60

Gly Cys Ala His His Ala Asp Ser Leu Tyr Thr Tyr Pro Val Ala Thr
 65                  70                  75                  80

Glu Cys His Cys Gly Lys Cys Asp Ser Asp Ser Thr Asp Cys Thr Val
                 85                  90                  95

Arg Gly Leu Gly Pro Ser Tyr Cys Ser Phe Ser Glu Met Lys Glu
            100                 105                 110


<210> SEQ ID NO 9
<211> LENGTH: 96
<212> TYPE: PRT
<213> ORGANISM: mammalian

<400> SEQUENCE: 9

Phe Pro Asp Gly Glu Phe Thr Met Gln Gly Cys Pro Glu Cys Lys Leu
  1               5                  10                  15

Lys Glu Asn Lys Tyr Phe Ser Lys Pro Asp Ala Pro Ile Tyr Gln Cys
             20                  25                  30
```

-continued

```
Met Gly Cys Cys Phe Ser Arg Ala Tyr Pro Thr Pro Ala Arg Ser Lys
         35                  40                  45

Lys Thr Met Leu Val Pro Lys Asn Ile Thr Ser Glu Ala Thr Cys Cys
     50                  55                  60

Val Ala Lys Ala Phe Thr Lys Ala Thr Val Met Gly Asn Val Arg Val
 65                  70                  75                  80

Glu Asn His Thr Glu Cys His Cys Ser Thr Cys Tyr Tyr His Lys Ser
                 85                  90                  95


<210> SEQ ID NO 10
<211> LENGTH: 111
<212> TYPE: PRT
<213> ORGANISM: mammalian

<400> SEQUENCE: 10

Arg Ser Cys Glu Leu Thr Asn Ile Thr Ile Thr Val Glu Lys Glu Glu
  1               5                  10                  15

Cys Ser Phe Cys Ile Ser Ile Asn Thr Thr Trp Cys Ala Gly Tyr Cys
             20                  25                  30

Tyr Thr Arg Asp Leu Val Tyr Lys Asp Pro Ala Arg Pro Asn Ile Gln
         35                  40                  45

Lys Ala Cys Thr Phe Lys Glu Leu Val Tyr Glu Thr Val Lys Val Pro
     50                  55                  60

Gly Cys Ala His His Ala Asp Ser Leu Tyr Thr Tyr Pro Val Ala Thr
 65                  70                  75                  80

Glu Cys His Cys Gly Lys Cys Asp Arg Asp Ser Thr Asp Cys Thr Val
                 85                  90                  95

Arg Gly Leu Gly Pro Ser Tyr Cys Ser Phe Ser Asp Ile Arg Glu
            100                 105                 110


<210> SEQ ID NO 11
<211> LENGTH: 108
<212> TYPE: PRT
<213> ORGANISM: Homo sapiens

<400> SEQUENCE: 11

Asn Ser Cys Glu Leu Thr Asn Ile Thr Ile Ala Ile Glu Lys Glu Glu
  1               5                  10                  15

Cys Arg Phe Cys Ile Ser Ile Asn Thr Thr Trp Cys Ala Gly Tyr Cys
             20                  25                  30

Tyr Thr Arg Asp Leu Val Tyr Lys Asp Pro Ala Arg Pro Lys Ile Gln
         35                  40                  45

Lys Thr Cys Thr Phe Lys Glu Leu Val Tyr Glu Thr Val Arg Val Pro
     50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly Glu
            100                 105


<210> SEQ ID NO 12
<211> LENGTH: 109
<212> TYPE: PRT
<213> ORGANISM: Homo sapiens

<400> SEQUENCE: 12
```

-continued

```
Asn Ser Cys Glu Leu Thr Asn Ile Thr Ile Ala Ile Glu Lys Glu Glu
  1               5                  10                  15

Cys Arg Phe Cys Ile Ser Ile Asn Thr Thr Trp Cys Ala Gly Tyr Cys
             20                  25                  30

Tyr Thr Arg Asp Leu Val Tyr Lys Asp Pro Ala Arg Pro Lys Ile Gln
         35                  40                  45

Lys Thr Cys Thr Phe Lys Glu Leu Val Tyr Glu Thr Val Arg Val Pro
     50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly Glu Met
            100                 105


<210> SEQ ID NO 13
<211> LENGTH: 110
<212> TYPE: PRT
<213> ORGANISM: Homo sapiens

<400> SEQUENCE: 13

Asn Ser Cys Glu Leu Thr Asn Ile Thr Ile Ala Ile Glu Lys Glu Glu
  1               5                  10                  15

Cys Arg Phe Cys Ile Ser Ile Asn Thr Thr Trp Cys Ala Gly Tyr Cys
             20                  25                  30

Tyr Thr Arg Asp Leu Val Tyr Lys Asp Pro Ala Arg Pro Lys Ile Gln
         35                  40                  45

Lys Thr Cys Thr Phe Lys Glu Leu Val Tyr Glu Thr Val Arg Val Pro
     50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly Glu Met Lys
            100                 105                 110


<210> SEQ ID NO 14
<211> LENGTH: 107
<212> TYPE: PRT
<213> ORGANISM: Homo sapiens

<400> SEQUENCE: 14

Asn Ser Cys Glu Leu Thr Asn Ile Thr Ile Ala Ile Glu Lys Glu Glu
  1               5                  10                  15

Cys Arg Phe Cys Ile Ser Ile Asn Thr Thr Trp Cys Ala Gly Tyr Cys
             20                  25                  30

Tyr Thr Arg Asp Leu Val Tyr Lys Asp Pro Ala Arg Pro Lys Ile Gln
         35                  40                  45

Lys Thr Cys Thr Phe Lys Glu Leu Val Tyr Glu Thr Val Arg Val Pro
     50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly
            100                 105
```

-continued

<210> SEQ ID NO 15
<211> LENGTH: 106
<212> TYPE: PRT
<213> ORGANISM: Homo sapiens

<400> SEQUENCE: 15

```
Asn Ser Cys Glu Leu Thr Asn Ile Thr Ile Ala Ile Glu Lys Glu Glu
  1               5                  10                  15

Cys Arg Phe Cys Ile Ser Ile Asn Thr Thr Trp Cys Ala Gly Tyr Cys
             20                  25                  30

Tyr Thr Arg Asp Leu Val Tyr Lys Asp Pro Ala Arg Pro Lys Ile Gln
         35                  40                  45

Lys Thr Cys Thr Phe Lys Glu Leu Val Tyr Glu Thr Val Arg Val Pro
     50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe
            100                 105
```

<210> SEQ ID NO 16
<211> LENGTH: 105
<212> TYPE: PRT
<213> ORGANISM: Homo sapiens

<400> SEQUENCE: 16

```
Asn Ser Cys Glu Leu Thr Asn Ile Thr Ile Ala Ile Glu Lys Glu Glu
  1               5                  10                  15

Cys Arg Phe Cys Ile Ser Ile Asn Thr Thr Trp Cys Ala Gly Tyr Cys
             20                  25                  30

Tyr Thr Arg Asp Leu Val Tyr Lys Asp Pro Ala Arg Pro Lys Ile Gln
         35                  40                  45

Lys Thr Cys Thr Phe Lys Glu Leu Val Tyr Glu Thr Val Arg Val Pro
     50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser
            100                 105
```

<210> SEQ ID NO 17
<211> LENGTH: 109
<212> TYPE: PRT
<213> ORGANISM: Homo sapiens

<400> SEQUENCE: 17

```
Ser Cys Glu Leu Thr Asn Ile Thr Ile Ala Ile Glu Lys Glu Glu Cys
  1               5                  10                  15

Arg Phe Cys Ile Ser Ile Asn Thr Thr Trp Cys Ala Gly Tyr Cys Tyr
             20                  25                  30

Thr Arg Asp Leu Val Tyr Lys Asp Pro Ala Arg Pro Lys Ile Gln Lys
         35                  40                  45

Thr Cys Thr Phe Lys Glu Leu Val Tyr Glu Thr Val Arg Val Pro Gly
     50                  55                  60

Cys Ala His His Ala Asp Ser Leu Tyr Thr Tyr Pro Val Ala Thr Gln
```

-continued

```
 65                  70                  75                  80

Cys His Cys Gly Lys Cys Asp Ser Asp Ser Thr Asp Cys Thr Val Arg
                 85                  90                  95

Gly Leu Gly Pro Ser Tyr Cys Ser Phe Gly Glu Met Lys
            100                 105


<210> SEQ ID NO 18
<211> LENGTH: 108
<212> TYPE: PRT
<213> ORGANISM: Homo sapiens

<400> SEQUENCE: 18

Cys Glu Leu Thr Asn Ile Thr Ile Ala Ile Glu Lys Glu Glu Cys Arg
  1               5                  10                  15

Phe Cys Ile Ser Ile Asn Thr Thr Trp Cys Ala Gly Tyr Cys Tyr Thr
             20                  25                  30

Arg Asp Leu Val Tyr Lys Asp Pro Ala Arg Pro Lys Ile Gln Lys Thr
         35                  40                  45

Cys Thr Phe Lys Glu Leu Val Tyr Glu Thr Val Arg Val Pro Gly Cys
     50                  55                  60

Ala His His Ala Asp Ser Leu Tyr Thr Tyr Pro Val Ala Thr Gln Cys
 65                  70                  75                  80

His Cys Gly Lys Cys Asp Ser Asp Ser Thr Asp Cys Thr Val Arg Gly
                 85                  90                  95

Leu Gly Pro Ser Tyr Cys Ser Phe Gly Glu Met Lys
            100                 105


<210> SEQ ID NO 19
<211> LENGTH: 108
<212> TYPE: PRT
<213> ORGANISM: Homo sapiens

<400> SEQUENCE: 19

Ser Cys Glu Leu Thr Asn Ile Thr Ile Ala Ile Glu Lys Glu Glu Cys
  1               5                  10                  15

Arg Phe Cys Ile Ser Ile Asn Thr Thr Trp Cys Ala Gly Tyr Cys Tyr
             20                  25                  30

Thr Arg Asp Leu Val Tyr Lys Asp Pro Ala Arg Pro Lys Ile Gln Lys
         35                  40                  45

Thr Cys Thr Phe Lys Glu Leu Val Tyr Glu Thr Val Arg Val Pro Gly
     50                  55                  60

Cys Ala His His Ala Asp Ser Leu Tyr Thr Tyr Pro Val Ala Thr Gln
 65                  70                  75                  80

Cys His Cys Gly Lys Cys Asp Ser Asp Ser Thr Asp Cys Thr Val Arg
                 85                  90                  95

Gly Leu Gly Pro Ser Tyr Cys Ser Phe Gly Glu Met
            100                 105


<210> SEQ ID NO 20
<211> LENGTH: 107
<212> TYPE: PRT
<213> ORGANISM: Homo sapiens

<400> SEQUENCE: 20

Cys Glu Leu Thr Asn Ile Thr Ile Ala Ile Glu Lys Glu Glu Cys Arg
  1               5                  10                  15

Phe Cys Ile Ser Ile Asn Thr Thr Trp Cys Ala Gly Tyr Cys Tyr Thr
             20                  25                  30
```

-continued

```
Arg Asp Leu Val Tyr Lys Asp Pro Ala Arg Pro Lys Ile Gln Lys Thr
        35                  40                  45

Cys Thr Phe Lys Glu Leu Val Tyr Glu Thr Val Arg Val Pro Gly Cys
    50                  55                  60

Ala His His Ala Asp Ser Leu Tyr Thr Tyr Pro Val Ala Thr Gln Cys
65                  70                  75                  80

His Cys Gly Lys Cys Asp Ser Asp Ser Thr Asp Cys Thr Val Arg Gly
                85                  90                  95

Leu Gly Pro Ser Tyr Cys Ser Phe Gly Glu Met
            100                 105


<210> SEQ ID NO 21
<211> LENGTH: 107
<212> TYPE: PRT
<213> ORGANISM: Homo sapiens

<400> SEQUENCE: 21

Ser Cys Glu Leu Thr Asn Ile Thr Ile Ala Ile Glu Lys Glu Glu Cys
 1               5                  10                  15

Arg Phe Cys Ile Ser Ile Asn Thr Thr Trp Cys Ala Gly Tyr Cys Tyr
            20                  25                  30

Thr Arg Asp Leu Val Tyr Lys Asp Pro Ala Arg Pro Lys Ile Gln Lys
        35                  40                  45

Thr Cys Thr Phe Lys Glu Leu Val Tyr Glu Thr Val Arg Val Pro Gly
    50                  55                  60

Cys Ala His His Ala Asp Ser Leu Tyr Thr Tyr Pro Val Ala Thr Gln
65                  70                  75                  80

Cys His Cys Gly Lys Cys Asp Ser Asp Ser Thr Asp Cys Thr Val Arg
                85                  90                  95

Gly Leu Gly Pro Ser Tyr Cys Ser Phe Gly Glu
            100                 105


<210> SEQ ID NO 22
<211> LENGTH: 106
<212> TYPE: PRT
<213> ORGANISM: Homo sapiens

<400> SEQUENCE: 22

Cys Glu Leu Thr Asn Ile Thr Ile Ala Ile Glu Lys Glu Glu Cys Arg
 1               5                  10                  15

Phe Cys Ile Ser Ile Asn Thr Thr Trp Cys Ala Gly Tyr Cys Tyr Thr
            20                  25                  30

Arg Asp Leu Val Tyr Lys Asp Pro Ala Arg Pro Lys Ile Gln Lys Thr
        35                  40                  45

Cys Thr Phe Lys Glu Leu Val Tyr Glu Thr Val Arg Val Pro Gly Cys
    50                  55                  60

Ala His His Ala Asp Ser Leu Tyr Thr Tyr Pro Val Ala Thr Gln Cys
65                  70                  75                  80

His Cys Gly Lys Cys Asp Ser Asp Ser Thr Asp Cys Thr Val Arg Gly
                85                  90                  95

Leu Gly Pro Ser Tyr Cys Ser Phe Gly Glu
            100                 105


<210> SEQ ID NO 23
<211> LENGTH: 106
<212> TYPE: PRT
<213> ORGANISM: Homo sapiens
```

<400> SEQUENCE: 23

Ser Cys Glu Leu Thr Asn Ile Thr Ile Ala Ile Glu Lys Glu Glu Cys
1 5 10 15

Arg Phe Cys Ile Ser Ile Asn Thr Thr Trp Cys Ala Gly Tyr Cys Tyr
20 25 30

Thr Arg Asp Leu Val Tyr Lys Asp Pro Ala Arg Pro Lys Ile Gln Lys
35 40 45

Thr Cys Thr Phe Lys Glu Leu Val Tyr Glu Thr Val Arg Val Pro Gly
50 55 60

Cys Ala His His Ala Asp Ser Leu Tyr Thr Tyr Pro Val Ala Thr Gln
65 70 75 80

Cys His Cys Gly Lys Cys Asp Ser Asp Ser Thr Asp Cys Thr Val Arg
85 90 95

Gly Leu Gly Pro Ser Tyr Cys Ser Phe Gly
100 105

<210> SEQ ID NO 24
<211> LENGTH: 105
<212> TYPE: PRT
<213> ORGANISM: Homo sapiens

<400> SEQUENCE: 24

Cys Glu Leu Thr Asn Ile Thr Ile Ala Ile Glu Lys Glu Glu Cys Arg
1 5 10 15

Phe Cys Ile Ser Ile Asn Thr Thr Trp Cys Ala Gly Tyr Cys Tyr Thr
20 25 30

Arg Asp Leu Val Tyr Lys Asp Pro Ala Arg Pro Lys Ile Gln Lys Thr
35 40 45

Cys Thr Phe Lys Glu Leu Val Tyr Glu Thr Val Arg Val Pro Gly Cys
50 55 60

Ala His His Ala Asp Ser Leu Tyr Thr Tyr Pro Val Ala Thr Gln Cys
65 70 75 80

His Cys Gly Lys Cys Asp Ser Asp Ser Thr Asp Cys Thr Val Arg Gly
85 90 95

Leu Gly Pro Ser Tyr Cys Ser Phe Gly
100 105

<210> SEQ ID NO 25
<211> LENGTH: 105
<212> TYPE: PRT
<213> ORGANISM: Homo sapiens

<400> SEQUENCE: 25

Ser Cys Glu Leu Thr Asn Ile Thr Ile Ala Ile Glu Lys Glu Glu Cys
1 5 10 15

Arg Phe Cys Ile Ser Ile Asn Thr Thr Trp Cys Ala Gly Tyr Cys Tyr
20 25 30

Thr Arg Asp Leu Val Tyr Lys Asp Pro Ala Arg Pro Lys Ile Gln Lys
35 40 45

Thr Cys Thr Phe Lys Glu Leu Val Tyr Glu Thr Val Arg Val Pro Gly
50 55 60

Cys Ala His His Ala Asp Ser Leu Tyr Thr Tyr Pro Val Ala Thr Gln
65 70 75 80

Cys His Cys Gly Lys Cys Asp Ser Asp Ser Thr Asp Cys Thr Val Arg
85 90 95

-continued

Gly Leu Gly Pro Ser Tyr Cys Ser Phe
100 105

<210> SEQ ID NO 26
<211> LENGTH: 104
<212> TYPE: PRT
<213> ORGANISM: Homo sapiens

<400> SEQUENCE: 26

Cys Glu Leu Thr Asn Ile Thr Ile Ala Ile Glu Lys Glu Glu Cys Arg
1 5 10 15

Phe Cys Ile Ser Ile Asn Thr Thr Trp Cys Ala Gly Tyr Cys Tyr Thr
20 25 30

Arg Asp Leu Val Tyr Lys Asp Pro Ala Arg Pro Lys Ile Gln Lys Thr
35 40 45

Cys Thr Phe Lys Glu Leu Val Tyr Glu Thr Val Arg Val Pro Gly Cys
50 55 60

Ala His His Ala Asp Ser Leu Tyr Thr Tyr Pro Val Ala Thr Gln Cys
65 70 75 80

His Cys Gly Lys Cys Asp Ser Asp Ser Thr Asp Cys Thr Val Arg Gly
85 90 95

Leu Gly Pro Ser Tyr Cys Ser Phe
100

<210> SEQ ID NO 27
<211> LENGTH: 104
<212> TYPE: PRT
<213> ORGANISM: Homo sapiens

<400> SEQUENCE: 27

Ser Cys Glu Leu Thr Asn Ile Thr Ile Ala Ile Glu Lys Glu Glu Cys
1 5 10 15

Arg Phe Cys Ile Ser Ile Asn Thr Thr Trp Cys Ala Gly Tyr Cys Tyr
20 25 30

Thr Arg Asp Leu Val Tyr Lys Asp Pro Ala Arg Pro Lys Ile Gln Lys
35 40 45

Thr Cys Thr Phe Lys Glu Leu Val Tyr Glu Thr Val Arg Val Pro Gly
50 55 60

Cys Ala His His Ala Asp Ser Leu Tyr Thr Tyr Pro Val Ala Thr Gln
65 70 75 80

Cys His Cys Gly Lys Cys Asp Ser Asp Ser Thr Asp Cys Thr Val Arg
85 90 95

Gly Leu Gly Pro Ser Tyr Cys Ser
100

<210> SEQ ID NO 28
<211> LENGTH: 103
<212> TYPE: PRT
<213> ORGANISM: Homo sapiens

<400> SEQUENCE: 28

Cys Glu Leu Thr Asn Ile Thr Ile Ala Ile Glu Lys Glu Glu Cys Arg
1 5 10 15

Phe Cys Ile Ser Ile Asn Thr Thr Trp Cys Ala Gly Tyr Cys Tyr Thr
20 25 30

Arg Asp Leu Val Tyr Lys Asp Pro Ala Arg Pro Lys Ile Gln Lys Thr
35 40 45

Cys Thr Phe Lys Glu Leu Val Tyr Glu Thr Val Arg Val Pro Gly Cys

-continued

```
     50                  55                  60

Ala His His Ala Asp Ser Leu Tyr Thr Tyr Pro Val Ala Thr Gln Cys
 65                  70                  75                  80

His Cys Gly Lys Cys Asp Ser Asp Ser Thr Asp Cys Thr Val Arg Gly
                 85                  90                  95

Leu Gly Pro Ser Tyr Cys Ser
            100


<210> SEQ ID NO 29
<211> LENGTH: 91
<212> TYPE: PRT
<213> ORGANISM: Homo sapiens

<400> SEQUENCE: 29

Pro Asp Val Gln Asp Cys Pro Glu Cys Thr Leu Gln Glu Asn Pro Phe
  1               5                  10                  15

Phe Ser Gln Pro Gly Ala Pro Ile Leu Gln Cys Met Gly Cys Cys Phe
            20                  25                  30

Ser Arg Ala Tyr Pro Thr Pro Leu Arg Ser Lys Lys Thr Met Leu Val
        35                  40                  45

Gln Lys Asn Val Thr Ser Glu Ser Thr Cys Cys Val Ala Lys Ser Tyr
     50                  55                  60

Asn Arg Val Thr Val Met Gly Gly Phe Lys Val Glu Asn His Thr Ala
 65                  70                  75                  80

Cys His Cys Ser Thr Cys Tyr Tyr His Lys Ser
                 85                  90


<210> SEQ ID NO 30
<211> LENGTH: 90
<212> TYPE: PRT
<213> ORGANISM: Homo sapiens

<400> SEQUENCE: 30

Asp Val Gln Asp Cys Pro Glu Cys Thr Leu Gln Glu Asn Pro Phe Phe
  1               5                  10                  15

Ser Gln Pro Gly Ala Pro Ile Leu Gln Cys Met Gly Cys Cys Phe Ser
            20                  25                  30

Arg Ala Tyr Pro Thr Pro Leu Arg Ser Lys Lys Thr Met Leu Val Gln
        35                  40                  45

Lys Asn Val Thr Ser Glu Ser Thr Cys Cys Val Ala Lys Ser Tyr Asn
     50                  55                  60

Arg Val Thr Val Met Gly Gly Phe Lys Val Glu Asn His Thr Ala Cys
 65                  70                  75                  80

His Cys Ser Thr Cys Tyr Tyr His Lys Ser
                 85                  90


<210> SEQ ID NO 31
<211> LENGTH: 89
<212> TYPE: PRT
<213> ORGANISM: Homo sapiens

<400> SEQUENCE: 31

Val Gln Asp Cys Pro Glu Cys Thr Leu Gln Glu Asn Pro Phe Phe Ser
  1               5                  10                  15

Gln Pro Gly Ala Pro Ile Leu Gln Cys Met Gly Cys Cys Phe Ser Arg
            20                  25                  30

Ala Tyr Pro Thr Pro Leu Arg Ser Lys Lys Thr Met Leu Val Gln Lys
        35                  40                  45
```

-continued

```
Asn Val Thr Ser Glu Ser Thr Cys Cys Val Ala Lys Ser Tyr Asn Arg
     50                  55                  60

Val Thr Val Met Gly Gly Phe Lys Val Glu Asn His Thr Ala Cys His
 65                  70                  75                  80

Cys Ser Thr Cys Tyr Tyr His Lys Ser
                 85


<210> SEQ ID NO 32
<211> LENGTH: 276
<212> TYPE: DNA
<213> ORGANISM: Homo sapiens

<400> SEQUENCE: 32

gctcctgatg tgcaggattg cccagaatgc acgctacagg aaaacccatt cttctcccag     60

ccgggtgccc caatacttca gtgcatgggc tgctgcttct ctagagcata tcccactcca    120

ctaaggtcca agaagacgat gttggtccaa aagaacgtca cctcagagtc cacttgctgt    180

gtagctaaat catataacag ggtcacagta atggggggtt tcaaagtgga gaaccacacg    240

gcgtgccact gcagtacttg ttattatcac aaatct                              276


<210> SEQ ID NO 33
<211> LENGTH: 324
<212> TYPE: DNA
<213> ORGANISM: Homo sapiens

<400> SEQUENCE: 33

aatagctgtg agctgaccaa catcaccatt gcaatagaga aagaagaatg tcgtttctgc     60

ataagcatca acaccacttg gtgtgctggc tactgctaca ccagggatct ggtgtataag    120

gacccagcca ggcccaaaat ccagaaaaca tgtaccttca aggaactggt atatgaaaca    180

gtgagagtgc ccggctgtgc tcaccatgca gattccttgt atacataccc agtggccacc    240

cagtgtcact gtggcaagtg tgacagcgac agcactgatt gtactgtgcg aggcctgggg    300

cccagctact gctcctttgg tgaa                                           324


<210> SEQ ID NO 34
<211> LENGTH: 327
<212> TYPE: DNA
<213> ORGANISM: Homo sapiens

<400> SEQUENCE: 34

aatagctgtg agctgaccaa catcaccatt gcaatagaga aagaagaatg tcgtttctgc     60

ataagcatca acaccacttg gtgtgctggc tactgctaca ccagggatct ggtgtataag    120

gacccagcca ggcccaaaat ccagaaaaca tgtaccttca aggaactggt atatgaaaca    180

gtgagagtgc ccggctgtgc tcaccatgca gattccttgt atacataccc agtggccacc    240

cagtgtcact gtggcaagtg tgacagcgac agcactgatt gtactgtgcg aggcctgggg    300

cccagctact gctcctttgg tgaaatg                                        327


<210> SEQ ID NO 35
<211> LENGTH: 330
<212> TYPE: DNA
<213> ORGANISM: Homo sapiens

<400> SEQUENCE: 35

aatagctgtg agctgaccaa catcaccatt gcaatagaga aagaagaatg tcgtttctgc     60

ataagcatca acaccacttg gtgtgctggc tactgctaca ccagggatct ggtgtataag    120
```

-continued

```
gacccagcca ggcccaaaat ccagaaaaca tgtaccttca aggaactggt atatgaaaca    180

gtgagagtgc ccggctgtgc tcaccatgca gattccttgt atacataccc agtggccacc    240

cagtgtcact gtggcaagtg tgacagcgac agcactgatt gtactgtgcg aggcctgggg    300

cccagctact gctcctttgg tgaaatgaaa                                     330


<210> SEQ ID NO 36
<211> LENGTH: 333
<212> TYPE: DNA
<213> ORGANISM: Homo sapiens

<400> SEQUENCE: 36

aatagctgtg agctgaccaa catcaccatt gcaatagaga aagaagaatg tcgtttctgc     60

ataagcatca acaccacttg gtgtgctggc tactgctaca ccagggatct ggtgtataag    120

gacccagcca ggcccaaaat ccagaaaaca tgtaccttca aggaactggt atatgaaaca    180

gtgagagtgc ccggctgtgc tcaccatgca gattccttgt atacataccc agtggccacc    240

cagtgtcact gtggcaagtg tgacagcgac agcactgatt gtactgtgcg aggcctgggg    300

cccagctact gctcctttgg tgaaatgaaa gaa                                 333


<210> SEQ ID NO 37
<211> LENGTH: 276
<212> TYPE: DNA
<213> ORGANISM: Homo sapiens

<400> SEQUENCE: 37

gctcctgatg tgcaggattg cccagaatgc acgctacagg aaaacccatt cttctcccag     60

ccgggtgccc caatacttca gtgcatgggc tgctgcttct caagagcata tcccactcca    120

ctaaggtcca agaagacgat gttggtccaa aagaacgtca cctcagagtc cacttgctgt    180

gtagctaaat catataacag ggtcacagta atggggggtt tcaaagtgga gaaccacacg    240

gcgtgccact gcagtacttg ttattatcac aaatct                              276


<210> SEQ ID NO 38
<211> LENGTH: 324
<212> TYPE: DNA
<213> ORGANISM: Homo sapiens

<400> SEQUENCE: 38

aacagctgtg agctcaccaa catcaccatt gcaatagaga aagaagaatg tcgtttctgc     60

atatcgatca acaccacttg gtgtgctggc tactgctaca ccagggatct ggtgtataag    120

gacccggccc gtcccaaaat ccagaaaaca tgtaccttca aggaactggt atatgaaaca    180

gtacgcgtgc ccggctgtgc tcaccatgca gattccttgt atacataccc agtggccacc    240

cagtgtcact gtggcaagtg tgacagcgac agcactgatt gtactgtgcg aggcctgggg    300

cccagctact gctcctttgg tgaa                                           324


<210> SEQ ID NO 39
<211> LENGTH: 321
<212> TYPE: DNA
<213> ORGANISM: Homo sapiens

<400> SEQUENCE: 39

aatagctgtg agctgaccaa catcaccatt gcaatagaga aagaagaatg tcgtttctgc     60

ataagcatca acaccacttg gtgtgctggc tactgctaca ccagggatct ggtgtataag    120
```

```
gacccagcca ggcccaaaat ccagaaaaca tgtaccttca aggaactggt atatgaaaca    180

gtgagagtgc ccggctgtgc tcaccatgca gattccttgt atacataccc agtggccacc    240

cagtgtcact gtggcaagtg tgacagcgac agcactgatt gtactgtgcg aggcctgggg    300

cccagctact gctcctttgg t                                              321


<210> SEQ ID NO 40
<211> LENGTH: 318
<212> TYPE: DNA
<213> ORGANISM: Homo sapiens

<400> SEQUENCE: 40

aatagctgtg agctgaccaa catcaccatt gcaatagaga aagaagaatg tcgtttctgc     60

ataagcatca acaccacttg gtgtgctggc tactgctaca ccagggatct ggtgtataag    120

gacccagcca ggcccaaaat ccagaaaaca tgtaccttca aggaactggt atatgaaaca    180

gtgagagtgc ccggctgtgc tcaccatgca gattccttgt atacataccc agtggccacc    240

cagtgtcact gtggcaagtg tgacagcgac agcactgatt gtactgtgcg aggcctgggg    300

cccagctact gctccttt                                                  318


<210> SEQ ID NO 41
<211> LENGTH: 315
<212> TYPE: DNA
<213> ORGANISM: Homo sapiens

<400> SEQUENCE: 41

aatagctgtg agctgaccaa catcaccatt gcaatagaga aagaagaatg tcgtttctgc     60

ataagcatca acaccacttg gtgtgctggc tactgctaca ccagggatct ggtgtataag    120

gacccagcca ggcccaaaat ccagaaaaca tgtaccttca aggaactggt atatgaaaca    180

gtgagagtgc ccggctgtgc tcaccatgca gattccttgt atacataccc agtggccacc    240

cagtgtcact gtggcaagtg tgacagcgac agcactgatt gtactgtgcg aggcctgggg    300

cccagctact gctcc                                                     315


<210> SEQ ID NO 42
<211> LENGTH: 327
<212> TYPE: DNA
<213> ORGANISM: Homo sapiens

<400> SEQUENCE: 42

agctgtgagc tgaccaacat caccattgca atagagaaag aagaatgtcg tttctgcata     60

agcatcaaca ccacttggtg tgctggctac tgctacacca gggatctggt gtataaggac    120

ccagccaggc ccaaaatcca gaaaacatgt accttcaagg aactggtata tgaaacagtg    180

agagtgcccg gctgtgctca ccatgcagat tccttgtata catacccagt ggccacccag    240

tgtcactgtg gcaagtgtga cagcgacagc actgattgta ctgtgcgagg cctggggccc    300

agctactgct cctttggtga aatgaaa                                        327


<210> SEQ ID NO 43
<211> LENGTH: 324
<212> TYPE: DNA
<213> ORGANISM: Homo sapiens

<400> SEQUENCE: 43

tgtgagctga ccaacatcac cattgcaata gagaaagaag aatgtcgttt ctgcataagc     60

atcaacacca cttggtgtgc tggctactgc tacaccaggg atctggtgta taaggaccca    120
```

-continued

```
gccaggccca aaatccagaa aacatgtacc ttcaaggaac tggtatatga aacagtgaga    180

gtgcccggct gtgctcacca tgcagattcc ttgtatacat acccagtggc cacccagtgt    240

cactgtggca agtgtgacag cgacagcact gattgtactg tgcgaggcct ggggcccagc    300

tactgctcct ttggtgaaat gaaa                                           324


<210> SEQ ID NO 44
<211> LENGTH: 324
<212> TYPE: DNA
<213> ORGANISM: Homo sapiens

<400> SEQUENCE: 44

agctgtgagc tgaccaacat caccattgca atagagaaag aagaatgtcg tttctgcata     60

agcatcaaca ccacttggtg tgctggctac tgctacacca gggatctggt gtataaggac    120

ccagccaggc ccaaaatcca gaaaacatgt accttcaagg aactggtata tgaaacagtg    180

agagtgcccg gctgtgctca ccatgcagat tccttgtata catacccagt ggccacccag    240

tgtcactgtg gcaagtgtga cagcgacagc actgattgta ctgtgcgagg cctggggccc    300

agctactgct cctttggtga aatg                                           324


<210> SEQ ID NO 45
<211> LENGTH: 321
<212> TYPE: DNA
<213> ORGANISM: Homo sapiens

<400> SEQUENCE: 45

tgtgagctga ccaacatcac cattgcaata gagaaagaag aatgtcgttt ctgcataagc     60

atcaacacca cttggtgtgc tggctactgc tacaccaggg atctggtgta taaggaccca    120

gccaggccca aaatccagaa aacatgtacc ttcaaggaac tggtatatga aacagtgaga    180

gtgcccggct gtgctcacca tgcagattcc ttgtatacat acccagtggc cacccagtgt    240

cactgtggca agtgtgacag cgacagcact gattgtactg tgcgaggcct ggggcccagc    300

tactgctcct ttggtgaaat g                                              321


<210> SEQ ID NO 46
<211> LENGTH: 321
<212> TYPE: DNA
<213> ORGANISM: Homo sapiens

<400> SEQUENCE: 46

agctgtgagc tgaccaacat caccattgca atagagaaag aagaatgtcg tttctgcata     60

agcatcaaca ccacttggtg tgctggctac tgctacacca gggatctggt gtataaggac    120

ccagccaggc ccaaaatcca gaaaacatgt accttcaagg aactggtata tgaaacagtg    180

agagtgcccg gctgtgctca ccatgcagat tccttgtata catacccagt ggccacccag    240

tgtcactgtg gcaagtgtga cagcgacagc actgattgta ctgtgcgagg cctggggccc    300

agctactgct cctttggtga a                                              321


<210> SEQ ID NO 47
<211> LENGTH: 318
<212> TYPE: DNA
<213> ORGANISM: Homo sapiens

<400> SEQUENCE: 47

tgtgagctga ccaacatcac cattgcaata gagaaagaag aatgtcgttt ctgcataagc     60
```

-continued atcaacacca cttggtgtgc tggctactgc tacaccaggg atctggtgta taaggaccca 120
gccaggccca aaatccagaa aacatgtacc ttcaaggaac tggtatatga aacagtgaga 180
gtgcccggct gtgctcacca tgcagattcc ttgtatacat acccagtggc cacccagtgt 240
cactgtggca agtgtgacag cgacagcact gattgtactg tgcgaggcct ggggcccagc 300
tactgctcct ttggtgaa 318

<210> SEQ ID NO 48
<211> LENGTH: 318
<212> TYPE: DNA
<213> ORGANISM: Homo sapiens

<400> SEQUENCE: 48
agctgtgagc tgaccaacat caccattgca atagagaaag aagaatgtcg tttctgcata 60
agcatcaaca ccacttggtg tgctggctac tgctacacca gggatctggt gtataaggac 120
ccagccaggc ccaaaatcca gaaaacatgt accttcaagg aactggtata tgaaacagtg 180
agagtgcccg gctgtgctca ccatgcagat tccttgtata catacccagt ggccacccag 240
tgtcactgtg gcaagtgtga cagcgacagc actgattgta ctgtgcgagg cctggggccc 300
agctactgct cctttggt 318

<210> SEQ ID NO 49
<211> LENGTH: 315
<212> TYPE: DNA
<213> ORGANISM: Homo sapiens

<400> SEQUENCE: 49
tgtgagctga ccaacatcac cattgcaata gagaaagaag aatgtcgttt ctgcataagc 60
atcaacacca cttggtgtgc tggctactgc tacaccaggg atctggtgta taaggaccca 120
gccaggccca aaatccagaa aacatgtacc ttcaaggaac tggtatatga aacagtgaga 180
gtgcccggct gtgctcacca tgcagattcc ttgtatacat acccagtggc cacccagtgt 240
cactgtggca agtgtgacag cgacagcact gattgtactg tgcgaggcct ggggcccagc 300
tactgctcct ttggt 315

<210> SEQ ID NO 50
<211> LENGTH: 315
<212> TYPE: DNA
<213> ORGANISM: Homo sapiens

<400> SEQUENCE: 50
agctgtgagc tgaccaacat caccattgca atagagaaag aagaatgtcg tttctgcata 60
agcatcaaca ccacttggtg tgctggctac tgctacacca gggatctggt gtataaggac 120
ccagccaggc ccaaaatcca gaaaacatgt accttcaagg aactggtata tgaaacagtg 180
agagtgcccg gctgtgctca ccatgcagat tccttgtata catacccagt ggccacccag 240
tgtcactgtg gcaagtgtga cagcgacagc actgattgta ctgtgcgagg cctggggccc 300
agctactgct ccttt 315

<210> SEQ ID NO 51
<211> LENGTH: 312
<212> TYPE: DNA
<213> ORGANISM: Homo sapiens

<400> SEQUENCE: 51
tgtgagctga ccaacatcac cattgcaata gagaaagaag aatgtcgttt ctgcataagc 60

-continued atcaacacca cttggtgtgc tggctactgc tacaccaggg atctggtgta taaggaccca 120
gccaggccca aaatccagaa aacatgtacc ttcaaggaac tggtatatga aacagtgaga 180
gtgcccggct gtgctcacca tgcagattcc ttgtatacat acccagtggc cacccagtgt 240
cactgtggca agtgtgacag cgacagcact gattgtactg tgcgaggcct ggggcccagc 300
tactgctcct tt 312

<210> SEQ ID NO 52
<211> LENGTH: 312
<212> TYPE: DNA
<213> ORGANISM: Homo sapiens

<400> SEQUENCE: 52
agctgtgagc tgaccaacat caccattgca atagagaaag aagaatgtcg tttctgcata 60
agcatcaaca ccacttggtg tgctggctac tgctacacca gggatctggt gtataaggac 120
ccagccaggc ccaaaatcca gaaaacatgt accttcaagg aactggtata tgaaacagtg 180
agagtgcccg gctgtgctca ccatgcagat tccttgtata catacccagt ggccacccag 240
tgtcactgtg gcaagtgtga cagcgacagc actgattgta ctgtgcgagg cctggggccc 300
agctactgct cc 312

<210> SEQ ID NO 53
<211> LENGTH: 309
<212> TYPE: DNA
<213> ORGANISM: Homo sapiens

<400> SEQUENCE: 53
tgtgagctga ccaacatcac cattgcaata gagaaagaag aatgtcgttt ctgcataagc 60
atcaacacca cttggtgtgc tggctactgc tacaccaggg atctggtgta taaggaccca 120
gccaggccca aaatccagaa aacatgtacc ttcaaggaac tggtatatga aacagtgaga 180
gtgcccggct gtgctcacca tgcagattcc ttgtatacat acccagtggc cacccagtgt 240
cactgtggca agtgtgacag cgacagcact gattgtactg tgcgaggcct ggggcccagc 300
tactgctcc 309

<210> SEQ ID NO 54
<211> LENGTH: 273
<212> TYPE: DNA
<213> ORGANISM: Homo sapiens

<400> SEQUENCE: 54
cctgatgtgc aggattgccc agaatgcacg ctacaggaaa acccattctt ctcccagccg 60
ggtgccccaa tacttcagtg catgggctgc tgcttctcta gagcatatcc cactccacta 120
aggtccaaga agacgatgtt ggtccaaaag aacgtcacct cagagtccac ttgctgtgta 180
gctaaatcat ataacagggt cacagtaatg gggggtttca aagtggagaa ccacacggcg 240
tgccactgca gtacttgtta ttatcacaaa tct 273

<210> SEQ ID NO 55
<211> LENGTH: 270
<212> TYPE: DNA
<213> ORGANISM: Homo sapiens

<400> SEQUENCE: 55
gatgtgcagg attgcccaga atgcacgcta caggaaaacc cattcttctc ccagccgggt 60

-continued

```
gccccaatac ttcagtgcat gggctgctgc ttctctagag catatcccac tccactaagg    120

tccaagaaga cgatgttggt ccaaaagaac gtcacctcag agtccacttg ctgtgtagct    180

aaatcatata acagggtcac agtaatgggg ggtttcaaag tggagaacca cacggcgtgc    240

cactgcagta cttgttatta tcacaaatct                                     270


<210> SEQ ID NO 56
<211> LENGTH: 267
<212> TYPE: DNA
<213> ORGANISM: Homo sapiens

<400> SEQUENCE: 56

gtgcaggatt gcccagaatg cacgctacag gaaaacccat tcttctccca gccgggtgcc     60

ccaatacttc agtgcatggg ctgctgcttc tctagagcat atcccactcc actaaggtcc    120

aagaagacga tgttggtcca aaagaacgtc acctcagagt ccacttgctg tgtagctaaa    180

tcatataaca gggtcacagt aatggggggt ttcaaagtgg agaaccacac ggcgtgccac    240

tgcagtactt gttattatca caaatct                                        267
```